Figure 2:
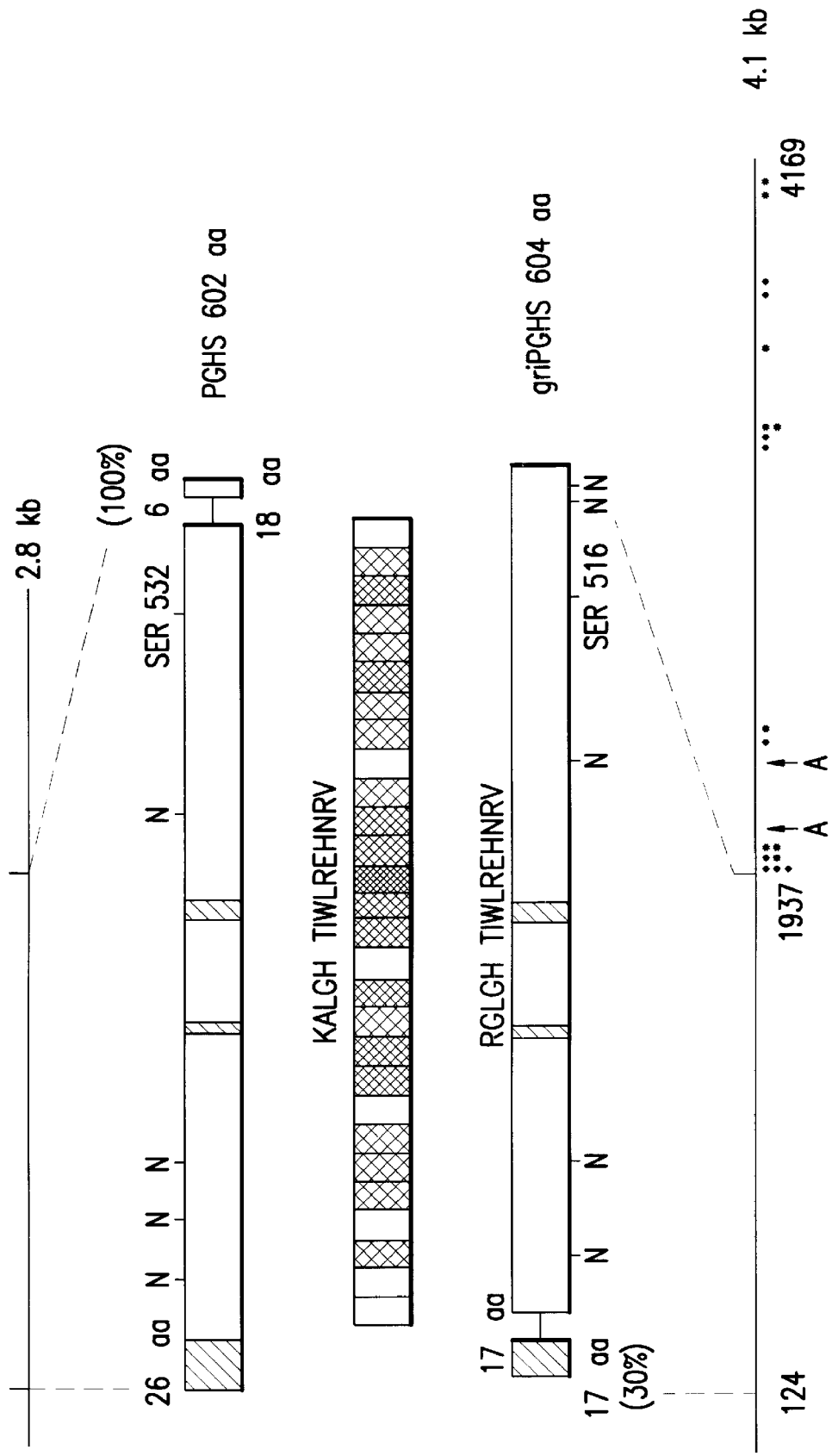

US005837479A

United States Patent [19]
Young et al.

[11] Patent Number: 5,837,479
[45] Date of Patent: Nov. 17, 1998

[54] SCREENING ASSAYS FOR INHIBITORS OF MAMMALIAN PROSTAGLANDIN H SYNTHASE-2

[76] Inventors: Donald A. Young, 540 Clover Hills Dr., Rochester, N.Y. 14618; Michael K. O'Banion, 3613 Clover St., Pittsford, N.Y. 14534; Virginia D. Winn, 139 Raleigh St., Rochester, N.Y. 14620

[21] Appl. No.: 480,065

[22] Filed: Jun. 7, 1995

Related U.S. Application Data

[60] Division of Ser. No. 487,752, Jun. 7, 1995, which is a continuation-in-part of Ser. No. 231,456, Apr. 20, 1994, abandoned, which is a continuation-in-part of Ser. No. 54,364, Apr. 28, 1993, abandoned, which is a continuation-in-part of Ser. No. 983,835, Dec. 1, 1992, abandoned, which is a continuation-in-part of Ser. No. 949,780, Sep. 22, 1992, abandoned, said Ser. No. 480,065, is a continuation-in-part of Ser. No. 34,143, Mar. 22, 1993, abandoned, which is a continuation of Ser. No. 949,780.

[51] Int. Cl.$^6$ .............................. C12Q 1/26; C12Q 1/28; C12Q 1/02
[52] U.S. Cl. ................................. 435/25; 435/28; 435/29
[58] Field of Search .................................. 435/25, 28, 29

[56] References Cited

U.S. PATENT DOCUMENTS

| | | | |
|---|---|---|---|
| 4,950,599 | 8/1990 | Bertling | 435/172.3 |
| 4,980,281 | 12/1990 | Housey | 435/29 |
| 5,087,572 | 2/1992 | Castellino et al. | 435/240.2 |
| 5,543,297 | 8/1996 | Cromlish et al. | 435/25 |

OTHER PUBLICATIONS

DeWitt et al., 1993, "PGH Synthase isoenzyme selectivity: The potential for safer nonsteroidal antiinflammatory drugs", Am J Med 95(2a):40S–44S.

DeWitt et al., 1990, "The aspirin and heme–binding sites of ovine and murine prostaglandin endoperoxide synthases", J Biol Chem 265:5192–5198.

Dickson et al., 1993, "Microglia and cytokines in neurological disease, with special reference to AIDS and Alzheimer's disease", Glia 7:75–83.

Espey, 1980, "Ovulation as an inflammatory reaction — A hypothesis", Biol Reproduct 22:73–106.

Espey, 1982, "Optimum time for administration of indomethacin to inhibit ovulation in the rabbit", Prostaglandin 23:329–335.

Funk et al., 1991, "Human platelet/erythroleukemia cell prostaglandin G/H synthase: cDNA cloning, expression and gene chromosomal assignment", FASEB J 5:2304–2312.

Futaki et al., 1993, "Selective inhibition of NS–398 on prostanoid production in inflamed tissue in rat carrageenan–air–pouch inflammation", J Pharm Pharmacol 45:753–755.

Griffin et al., 1989, "Brain interleukin 1 and S–100 immunoreactivity are elevated in Down syndrome and Alzheimer disease", Proc Natl Acad Sci 88:7611–7615.

Han et al., 1990, "Persistent induction of cyclooxygenase in p60$^{v-src}$–transformed 3T3 fibroblasts", Proc Natl Acad Sci 87:3373–3377.

Herschman et al., 1992, "Characterization of a gene encoding a second prostaglandin synthase/cyclooxygenase (PGS/COX), whose message and protein are induced by mitogens and inhibited by glucocorticoids", *8th International Conference on Prostaglandins and Related Compounds* on Jul. 26–31, 1992, Montreal, Canada, Abstract 302.

Herschmann, 1994, "Regulation of prostaglandin synthase–1 and prostaglandin synthase–2", Cancer and Metastasis Reviews 13:241–256.

Hla & Neilson, 1992, "Human cyclooxygenase–2 cDNA", Proc Natl Acad Sci 89:7384–7388.

Hla et al., 1986, "Isolation of the cDNA for human prostaglandin H synthase", Prostaglandins 32:829–845.

Johnson et al., 1992, "Complement mRNA in the mammalian brain: Responses to Alzheimer's disease and experimental brain lesioning", Neurobiol Aging 13:641–648.

Jones et al., 1993, "Molecular cloning of human prostaglandin endoperoxide synthase type II and demonstration of expression in response to cytokines", J Biol Chem 268:9049–9054.

Kelly, 1994, "Pregnancy maintenance and parturition: The role of prostaglandin in manipulating the immune and inflammatory response", Endocrine Reviews 15(5):684–706.

Kimura and Ikeda–Saito, 1988, "Human myeloperoxidase and thyroid peroxidase, two enzymes with separate and distinct physiological functions, are evolutionary related members of the same gene familly", Prot Struc Func Genetics 3:113–120.

Kitzler et al., 1992, "Two distinct forms of prostaglandin H synthase (PHS) are induced in rat tracheal epithelium cells by TPA and EGF treatment", *8th International Conference on Prostaglandins and Related Compounds* on Jul. 26–31, 1992, Montreal, Canada, Abstract 528.

Kujubu et al., "TIS10, a phorbol ester tumor promoter–inducible mRNA from Swiss 3T3 cells, encodes a novel prostaglandin synthase/cyclooxygenase homologue", J Biol Chem 266:12866–12872.

Kune et al., 1988, "Colorectal cancer risk, chronic illnesses, operations, and medications: Case control results from the Melbourne colorectal cancer study", Cancer Res 48:4399–4404.

(List continued on next page.)

*Primary Examiner*—Robert A. Wax
*Assistant Examiner*—Kawai Lau

[57] ABSTRACT

The invention relates to the gene encoding the mammalian prostaglandin H synthase-2 and its product. More specifically, the invention relates to the diagnosis of aberrant PGHS-2 gene or gene product; the identification, production, and use of compounds which modulate PGHS-2 gene expression or the activity of the PGHS-2 gene product including but not limited to nucleic acid encoding PGHS-12 and homologues, analogues, and deletions thereof, as well as antisense, ribozyme, triple helix, antibody, and polypeptide molecules as well as small inorganic molecules; and pharmaceutical formulations and routes of administration for such compounds.

7 Claims, 22 Drawing Sheets

OTHER PUBLICATIONS

Kosaka et al., 1994, "Characterization of the human gene (PTSG-2) encoding prostaglandin endoperoxide synthase 2", Eur J Biochem 221:889–897.

Lapchak and Araujo, 1993, "Hippocampal interleukin (IL)-1, IL-2 and IL-3 but not IL-6 levels are elevated in Alzheimer's but not Parkinson's disease", Soc Neurosci Abstr 19:191.

Lee et al., 1988, "Generation of cDNA probes directed by amino acid sequence: Cloning of urate oxidase", Science 239:1288–1291.

Levenson et al., 1985, "Growth factor–and dexamethasone–induced proteins in Swiss 3T3 cells", J Biol Chem 260:8056–8063.

Lim et al., 1987, "Cloning of tetradecanoyl phorbol ester–induced 'primary response' sequences and their expression in density–arrested Swiss 3T3 cells and a TPA non–proliferative variant", Oncogene 1:263–270.

Marnet, 1992, "Aspirin and the potential role of prostaglandins in colon cancer", Cancer Res 52:5575–5589.

Masferrer et al., 1994, "Selective inhibition of inducible cyclooxygenase 2 in vivo is antiinflammatory and nonulcerogenic", Proc Natl Acad Sci 91:3228–3232.

McGeer & Rogers, 1992, "Anti–inflammatory agents as a therapeutic approach to Alzheimer's disease", Neurology 42:447–449.

McGeer et al., 1989, "Activation of the classical complement pathway in brain tissue of Alzheimer patient", Neurosci Lett 107:341–346.

Meade et al., 1993, "Expression of the murine prostaglandin (PGH) synthase–1 and PGH synthase–2 isozymes in cos–1 cells", J Lipid Mediators 6:119–129.

Meade et al., 1993, "Differential inhibition of prostaglandin endoperoxide synthase (Cyclooxygenase) isozymes by aspirin and other non–steroidal anti–inflammatory drugs", J Biol Chem 268(9):6610–6614.

Meade et al., 1992, "Pharmacological profiles of the PGH synthase–1 and PGH synthase–2", *8th International Conference on Prostaglandins and Related Compounds* on Jul. 26–31, 1992, Montreal, Canada, Abstract 304.

Mitchell et al, 1992, "An interleukin–1β–inducible cyclooxygenase in human amnion", *8th International Conference on Prostaglandins and Related Compounds* on Jul. 26–31, 1992, Montreal, Canada, Abstract 299.

O'Banion et al., 1992, "cDNA cloning and functional activity of a glucocorticoid–regulated inflammatory cyclooxygenase", Proc Natl Acad Sci 89:4888–4892.

O'Banion et al., 1992, "Regulation of a novel cyclooxygenase (prostaglandin G/H synthase) gene by dexamethasone and calcium ionophore in astrocytes", Soc Neurosci Abstr. 18:1449.

O'Banion et al., 1991, "Bovine papillomavirus type 1 alters the processing of host glucose–and calcium–modulated endoplasmic reticulum proteins", J Virol 65:3481–3488.

O'Banion et al., 1991, "A serum–and glucocorticoid–regulated 4–kilobase mRNA encodes a cyclooxygenase–related protein", J Biol Chem 266:23261–23267.

O'Sullivan et al., 1992, "Induction of a novel cyclooxygenase (cyclooxygenase–2) is responsible for endotoxin priming for rabbit alveolar macrophages for amplified synthesis of prostanoids", *8th International Conference on Prostaglandins and Related Compounds* on Jul. 26–31, 1992, Montreal, Canada, Abstract 311.

Otto et al., 1992, "Structure/function relationships of PGH synthases–1 and –2", *8th International Conference on Prostaglandins and Related Compounds* on Jul. 26–31, 1992, Montreal, Canada, Abstract 301.

Peters–Golden et al., 1992, "Upregulation of prostaglandin H synthase (PGHS) activity in differentiating alveolar epithelial cells (AEC): Possible expression of a constitutive form of the enzyme", *8th International Conference on Prostaglandins and Related Compounds* on Jul. 26–31, 1992, Montreal, Canada, Abstract 540.

Pritchard et al., 1994, "Induction of cyclooxygenase–2 in rat vascular smooth muscle cells in vitro and in vivo", J Biol Chem 269:8504–8509.

Raz et al., 1988, "Regulation of fibroblast cyclooxygenase synthesis by interleukin–1", J Biol Chem 263(6):3022–3028.

Raz, et al., 1989, "Temporal and pharmacological division of fibroblast cyclooxygenase expression into transcriptional and translational phases", Proc Natl Acad Sci 86:1657–1661.

Rogers et al., 1993, "Clinical trial of indomethacin in Alzheimer's disease", Neurology 43:1609–1611.

Ryseck et al., 1992, "Identification of an immediate early gene, *pghs*–B, whose protein product has prostaglandin synthase/cyclooxygenase activity", Cell Growth & Differ 3:443–450.

Simmons et al., 1992, "Genetic regulation and drug inhibition of prostaglandin G/H synthase isozyme–2", *8th International Conference on Prostaglandins and Related Compounds* on Jul. 26–31, 1992, Montreal, Canada, Abstract 305.

Simmons et al., 1992, "Multiple cyclooxygenases: Cloning of a mitogen–inducible form", ** 67–78.

Sirois et al., 1992, "Purification and characterization of a novel, distinct isoform of prostaglandin endoperoxidase synthase induced by human chorionic gonadotropin in granulosa cells of rat preovulatory follicles", J Biol Chem 267(9):6382–6388.

Smith and Marnett, 1992, "Differential expression of the two forms of the prostaglandin endoperoxide synthase gene in lewis lung carcinoma", *8th International Conference on Prostaglandins and Related Compounds* on Jul. 26–31, 1992, Montreal, Canada, Abstract 532.

Vane et al., 1994, "Inducible isoforms of cyclooxygenase and nitric–oxide synthase in inflammation", Proc Natl Acad Sci 91:2046–2050.

Waddell & Loughry, 1983, "Sulindac for polyposis of the colon", J Surg Oncol 24:83–87.

Winn et al., 1992, "Genetic basis for two pools of cyclooxygenase activity: Cloning of griPGHS, a second cyclooxygenase", *8th International Conference on Prostaglandins and Related Compounds* on Jul. 26–31, 1992, Montreal, Canada, Abstract 310.

Winn et al., 1993, "Anti–inflammatory glucocorticoid action: Inhibition of griPGHS, a new cycloxygenase", J Lipid Mediat 6:101–111.

Xie et al., 1991, "Expression of a mitogen–responsive gene encoding prostaglandin synthase is regulated by mRNA splicing", Proc Natl Acad Sci 2692–2696.

Yamagata et al., 1993, "Expression of a mitogen–inducible cyclooxygenase in brain neurons: Regulation by synaptic activity and glucocorticoids", Neuron 11:371–386.

Yokahama and Tanabe, 1984, "Cloning of human gene encoding prostaglandin endoperoxide synthase and primary structure of the enzyme", Biochem Biophys Res Commun 165:888–894.

```
  25  CTTCAGGAGTCAGTCAGGACTCTGCTCACGAAGGAACTCAGCACTGCATCCTGCCAGCTC   84
  85  CACCGCCACCACTACTGCCACCTCCGCTGCCACCTCTGCGATGCTCTTCCGAGCTGTGCT  144
                                                  M  L  F  R  A  V  L    7
 145  GCTCTGCGCTGCCCTGGGGCTCAGCCAGGCAGCAAATCCTTGCTGTTCCAATCCATGTCA  204
   8   L  C  A  A  L  G  L  S  Q  A  A  N  P  C  C  S  N  P  C  Q    27
 205  AAACCGTGGGGAATGTATGAGCACAGGATTTGACCAGTATAAGTGTGACTGTACCCGGAC  264
  28   N  R  G  E  C  M  S  T  G  F  D  Q  Y  K  C  D  C  T  R  T    47
 265  TGGATTCTATGGTGAAAACTGTACTACACCTGAATTTCTGACAAGAATCAAATTACTGCT  324
  48   G  F  Y  G  E  N  C  T  T  P  E  F  L  T  R  I  K  L  L  L    67
 325  GAAGCCCACCCCAAACACAGTGCACTACATCCTGACCCACTTCAAGGGAGTCTGGAACAT  384
  68   K  P  T  P  N  T  V  H  Y  I  L  T  H  F  K  G  V  W  N  I    87
 385  TGTGAACAACATCCCCTTCCTGCGAAGTTTAATCATGAAATATGTGCTGACATCCAGATC  444
  88   V  N  N  I  P  F  L  R  S  L  I  M  K  Y  V  L  T  S  R  S   107
 445  ATATTTGATTGACAGTCCACCTACTTACAATGTGCACTATGGTTACAAAAGCTGGGAAGC  504
 108   Y  L  I  D  S  P  P  T  Y  N  V  H  Y  G  Y  K  S  W  E  A   127
 505  CTTCTCCAACCTCTCCTACTACACCAGGGCCCTTCCTCCCGTAGCAGATGACTGCCCAAC  564
 128   F  S  N  L  S  Y  Y  T  R  A  L  P  P  V  A  D  D  C  P  T   147
 565  TCCCATGGGTGTGAAGGGAAATAAGGAGCTTCCTGATTCAAAAGAAGTGCTGGAAAAGGT  624
 148   P  M  G  V  K  G  N  K  E  L  P  D  S  K  E  V  L  E  K  V   167
 625  TCTTCTACGGAGAGAGTTCATCCCTGACCCCCAAGGCTCAAATATGATGTTTGCATTCTT  684
 168   L  L  R  R  E  F  I  P  D  P  Q  G  S  N  M  M  F  A  F  F   187
 685  TGCCCAGCACTTCACCCATCAGTTTTTCAAGACAGATCATAAGCGAGGACCTGGGTTCAC  744
 188   A  Q  H  F  T  H  Q  F  F  K  T  D  H  K  R  G  P  G  F  T   207
 745  CCGAGGACTGGGCCATGGAGTGGACTTAAAATCACATTTATGGTGAAACTCTGGACAGACA  804
 208   R  G  L  G  H  G  V  D  L  N  H  I  Y  G  E  T  L  D  R  Q   227
 805  ACATAAACTGCGCCTTTTCAAGGATGGAAAATTGAAATATCAGGTCATTGGTGGAGAGGT  864
 228   H  K  L  R  L  F  K  D  G  K  L  K  Y  Q  V  I  G  G  E  V   247
 865  GTATCCCCCCACAGTCAAAGACACTCAGGTAGAGATGATCTACCCTCCTCACATCCCTGA  924
 248   Y  P  P  T  V  K  D  T  Q  V  E  M  I  Y  P  P  H  I  P  E   267
 925  GAACCTGCAGTTTGCTGTGGGGCAGGAAGTCTTTGGTCTGGTGCCTGGTCTGATGATGTA  984
 268   N  L  Q  F  A  V  G  Q  E  V  F  G  L  V  P  G  L  M  M  Y   287
 985  TGCCACCATCTGGCTTCGGGAGCACAACAGAGTGTGCGACATACTCAAGCAGGAGCATCC 1044
 288   A  T  I  W  L  R  E  H  N  R  V  C  D  I  L  K  Q  E  H  P   307
1045  TGAGTGGGGTGATGAGCAACTATTCCAAACCAGCAGACTCATACTCATAGGAGAGACTAT 1104
 308   E  W  G  D  E  Q  L  F  Q  T  S  R  L  I  L  I  G  E  T  I   327
1105  CAAGATAGTGATCGAAGACTACGTGCAACACCTGAGCGGTTACCACTTCAAACTCAAGTT 1164
 328   K  I  V  I  E  D  Y  V  Q  H  L  S  G  Y  H  F  K  L  K  F   347
1165  TGACCCAGAGCTCCTTTTCAACCAGCAGTTCCAGTATCAGAACCGCATTGCCTCTGAATT 1224
 348   D  P  E  L  L  F  N  Q  Q  F  Q  Y  Q  N  R  I  A  S  E  F   367
1225  CAACACACTCTATCACTGGCACCCCCTGCTGCCCGACACCTTCAACATTGAAGACCAGGA 1284
 368   N  T  L  Y  H  W  H  P  L  L  P  D  T  F  N  I  E  D  Q  E   387
1285  GTACAGCTTTAAACAGTTTCTCTACAACAACTCCATCCTCCTGGAACATGGACTCACTCA 1344
 388   Y  S  F  K  Q  F  L  Y  N  N  S  I  L  L  E  H  G  L  T  Q   407
```

FIG.1A

```
1345  GTTTGTTGAGTCATTCACCAGACAGATTGCTGGCCGGGTTGCTGGGGGAAGAAATGTGCC  1404
408    F  V  E  S  F  T  R  Q  I  A  G  R  V  A  G  G  R  N  V  P   427
1405  AATTGCTGTACAAGCAGTGGCAAAGGCCTCCATTGACCAGAGCAGAGAGATGAAATACCA  1464
428    I  A  V  Q  A  V  A  K  A  S  I  D  Q  S  R  E  M  K  Y  Q   447
1465  GTCTCTCAATGAGTAnCGGAAACGCTTCTCCCTGAAGCCGTACACATCATTTGAAGAACT  1524
448    S  L  N  E  X  R  K  R  F  S  L  K  P  Y  T  S  F  E  E  L   467
1525  TACAGGAGAGAAGGAAATGGCTGCAGAATTGAAAGCCCTCTACAGTGACATCGATGTCAT  1584
468    T  G  E  K  E  M  A  A  E  L  K  A  L  Y  S  D  I  D  V  M   487
1585  GGAACTGTACCCTGCCCTGCTGGTGGAAAAACCTCGTCCAGATGCTATCTTTGGGGAGAC  1644
488    E  L  Y  P  A  L  L  V  E  K  P  R  P  D  A  I  F  G  E  T   507
1645  CATGGTAGAGCTTGGAGCACCATTCTCCTTGAAAGGACTTATGGGAAATCCCATCTGTTC  1704
508    M  V  E  L  G  A  P  F Ⓢ L  K  G  L  M  G  N  P  I  C  S   527
1705  TCCTCAATACTGGAAGCCGAGCACCTTTGGAGGCGAAGTGGGTTTTAAGATCATCAATAC  1764
528    P  Q  Y  W  K  P  S  T  F  G  G  E  V  G  F  K  I  I  N  T   547
1765  TGCCTCAATTCAGTCTCTCATCTGCAATAATGTGAAGGGGTGTCCCTTCACTTCTTTCAA  1824
548    A  S  I  Q  S  L  I  C  N  N  V  K  G  C  P  F  T  S  F  N   567
1825  TGTGCAAGATCCACAGCCTACCAAAACAGCCACCATCAATGCAAGTGCCTCCCACTCCAG  1884
568    V  Q  D  P  Q  P  T  K  T  A  T  I  N̲  A̲  S̲  A  S  H  S  R   587
1885  ACTAGATGACATTAACCCTACAGTACTAATCAAAAGGCGTTCAACTGAGCTGTAAAAGTC  1944
588    L  D  D  I  N̲  P̲  T  V  L  I  K  R  R  S  T  E  L            607
```

FIG.1B

```
 90  CCGCTGCGATGCTCGCCCGCGCCCTGCTGCTGTGCGCGGTCCTGGCGCTCAGCCATACAG  149

150  CAAATCCTTGCTGTTCCCACCCATGTCAAAACCGAGGTGTATGTATGAGTGTGGGATTTG  209

210  ACCAGTATAAGTGCGATTGTACCCGGACAGGATTCTATGGAGAAAACTGCTCAACACCGG  269

270  AATTTTTGACAAGAATAAAATTATTTCTGAAACCCACTCCAAACACAGTGCACTACATAC  329

330  TTACCCACTTCAAGGGATTTTGGAACGTTGTGAATAACATTCCCTTCCTTCGAAATGCAA  389

390  TTATGAGTTATGTGTTGACATCCAGATCACATTTGATTGACAGTCCACCAACTTACAATG  449

450  CTGACTATGGCTACAAAAGCTGGGAAGCCTTCTCCAACCTCTCCTATTATACTAGAGCCC  509

510  TTCCTCCTGTGCCTGATGATTGCCCGACTCCCTTGGGTGTCAAAGGTAAAAAGCAGCTTC  569

570  CTGATTCAAATGAGATTGTGGAAAAATTGCTTCTAAGAAGAAAGTTCATCCCTGATCCCC  629

630  AGGGCTCAAACATGATGTTTGCATTCTTTGCCCAGCACTTCACGCATCAGTTTTTCAAGA  689

690  CAGATCATAAGCGAGGGCCAGCTTTCACCAACGGGCTGGGCCATGGGGTGGACTTAAATC  749

750  ATATTTACGGTGAAACTCTGGCTAGACAGCGTAAACTGCGCCTTTTCAAGGATGGAAAAA  809

810  TGAAATATCAGATAATTGATGGAGAGATGTATCCTCCCACAGTCAAAGATACTCAGGCAG  869

870  AGATGATCTACCCTCCTCAAGTCCCTGAGCATCTACGGTTTGCTGTGGGGCAGGAGGTCT  929

930  TTGGTCTGGTGCCTGGTCTGATGATGTATGCCACAATCTGGCTGCGGGAACACAACAGAG  989

990  TATGCGATGTGCTTAAACAGGAGCATCCTGAATGGGGTGATGAGCAGTTGTTCCAGACAA  1049
```

FIG.6A

1050 GCAGGCTAATACTGATAGGAGAGACTATTAAGATTGTGATTGAAGATTATGTGCAACACT 1109

1110 TGAGTGGCTATCACTTCAAACTGAAGTTTGACCCAGAACTACTTTTCAACAAACAGTTCC 1169

1170 AGTACCAAAATCGTATTGCTGCTGAATTTAACACCCTCTATCACTGGCATCCCCTTCTGC 1229

1230 CTGACACCTTTCAAATTCATGACCAGAAATACAACTATCAACAGTTTATCTACAACAACT 1289

1290 CTATATTGCTGGAACATGGAATTACCCAGTTTGTTGAATCATTCACCAGGCAGATTGCTG 1349

1350 GCAGGGTTGCTGGTGGTAGGAATGTTCCACCCGCAGTACAGAAAGTATCACAGGCTTCCA 1409

1410 TTGACCAGAGCAGGCAGATGAAATACCAGTCTTTTAATGAGTACCGCAAACGCTTTATGC 1469

1470 TGAAGCCCTATGAATCATTTGAAGAACTTACAGGAGAAAAGGAAATGTCTGCAGAGTTGG 1529

1530 AAGCACTCTATGGTGACATCGATGCTGTGGAGCTGTATCCTGCCCTTCTGGTAGAAAAGC 1589

1590 CTCGGCCAGATGCCATCTTTGGTGAAACCATGGTAGAAGTTGGAGCACCATTCTCCTTGA 1649

1650 AAGGACTTATGGGTAATGTTATATGTTCTCCTGCCTACTGGAAGCCAAGCACTTTTGGTG 1709

1710 GAGAAGTGGGTTTTCAAATCATCAACACTGCCTCAATTCAGTCTCTCATCTGCAATAACG 1769

1770 TGAAGGGCTGTCCCTTTACTTCATTCAGTGTTCCAGATCCAGAGCTCATTAAAACAGTCA 1829

1830 CCATCAATGCAAGTTCTTCCCGCTCCGGACTAGATGATATCAATCCCACAGTACTACTAA 1889

1890 AAGAACGTTCGACTGAACTGTAGAAGTCTAATAC 1923

FIG.6B

```
hPGHS-2    MLARALLLCA VLALSHTANP CCSHPCQNRG VCMSVGFDQY KCDCTRTGFY
           |||||||||| |||||||||| |||||||||| |||||||||| ||||||||||
hPGHS-2    MLARALLLCA VLALSHTANP CCSHPCQNRG VCMSVGFDQY KCDCTRTGFY

51    GENCSTPEFL TRIKLFLKPT PNTVHYILTH FKGFWNVVNN IPFLRNAIMS
           |||||||||| |||||||||| |||||||||| |||||||||| ||||||||||
     51    GENCSTPEFL TRIKLFLKPT PNTVHYILTH FKGFWNVVNN IPFLRNAIMS

101    YVLTSRSHLI DSPPTYNADY GYKSWEAFSN LSYYTRALPP VPDDCPTPLG
           |||||||||| |||||||||| |||||||||| |||||||||| ||||||||||
    101    YVLTSRSHLI DSPPTYNADY GYRSWEAFSN LSYYIRALPP VPDDCPTPLG

151    VKGKKQLPDS NEIVEKLLLR RKFIPDPQGS NMMFAFFAQH FTHQFFKTDH
           |||||||||| ||||||||||  |||||||||| |||||||||| ||||||||||
    151    VKGKKQLPDS NEIVGKLLLR RKFIPDPQGS NMMFAFFAQH FTHQFFKTDH

201    KRGPAFTNGL GHGVDLNHIY GETLARQRKL RLFKDGKMKY QIIDGEMYPP
           |||||||||| |||||||||| |||||||||| |||||||||| ||||||||||
    201    KRGPAFTNGL GHGVDLNHIY GETLARQRKL RLFKDGKMKY QIIDGEMYPP

251    TVKDTQAEMI YPPQVPEHLR FAVGQEVFGL VPGLMMYATI WLREHNRVCD
           |||||||||| |||||||||| |||||||||| |||||||||| ||||||||||
    251    TVKDTQAEMI YPPQVPEHLR FAVGQEVFGL VPGLMMYATI WLREHNRVCD

301    VLKQEHPEWG DEQLFQTSRL ILIGETIKIV IEDYVQHLSG YHFKLKFDPE
           |||||||||| |||||||||| |||||||||| |||||||||| ||||||||||
    301    VLKQEHPEWG DEQLFQTSRL ILIGETIKIV IEDYVQHLSG YHFKLKFDPE

351    LLFNKQFQYQ NRIAAEFNTL YHWHPLLPDT FQIHDQKYNY QQFIYNNSIL
           |||||||||| |||||||||| |||||||||| |||||||||| ||||||||||
    351    LLFNKQFQYQ NRIAAEFNTL YHWHPLLPDT FQIHDQKYNY QQFIYNNSIL

401    LEHGITQFVE SFTRQIAGRV AGGRNVPPAV QKVSQASIDQ SRQMKYQSFN
           |||||||||| |||||||||| |||||||||| |||||||||| ||||||||||
    401    LEHGITQFVE SFTRQIAGRV AGGRNVPPAV QKVSQASIDQ SRQMKYQSFN

451    EYRKRFMLKP YESFEELTGE KEMSAELEAL YGDIDAVELY PALLVEKPRP
           |||||||||| |||||||||| |||||||||| |||||||||| ||||||||||
    451    EYRKRFMLKP YESFEELTGE KEMSAELEAL YGDIDAVELY PALLVEKPRP

501    DAIFGETMVE VGAPFSLKGL MGNVICSPAY WKPSTFGGEV GFQIINTASI
           |||||||||| |||||||||| |||||||||| |||||||||| ||||||||||
    501    DAIFGETMVE VGAPFSLKGL MGNVICSPAY WKPSTFGGEV GFQIINTASI

551    QSLICNNVKG CPFTSFSVPD PELIKTVTIN ASSSRSGLDD INPTVLLKER
           |||||||||| |||||||||| |||||||||| |||||||||| ||||||||||
    551    QSLICNNVKG CPFTSFSVPD PELIKTVTIN ASSSRSGLDD INPTVLLKER

601    STEL 604
           ||||
    601    STEL 604
```

FIG.7

```
                                    10        20        30        40
PGHS-1                              CCGCGCCATGAGCCGGAGTCTCTTGCTCCGGTTCTTGCTG
              10        20        30        40        50
PGHS-2  CCGCTGC-GATGCTCGC-CCGCGCCCTGCTGCTGTGCGCGG-TCCTGGCGCTCAGCCA-T
        |||||   ||||||  |||||  |||  |  |||  |||||  ||  || ||  |||
PGHS-1  TTGCTGCTCCTGCTCCCGCCGCTCCCCG-TCCTGCTCGCGGACCCAGGGGCGC--CCACG
                 50        60        70        80        90
                   60        70        80        90        100       110
PGHS-2   ACAGCAAATCCTTGCTGTTCCCACCCATGTCAAAACCCAGGTGTATGTATGAGTGTGGGA
         |||  ||||| ||  |||| || | ||||| || |||  || | |||| |  |  | ||
PGHS-1   CCAGTGAATCCCTGTTGTTACTATCCATGCCAGCACCAGGGCATCTGTGTCCGCTTCGGC
          100       110       120       130       140       150
              120       130       140       150       160       170
PGHS-2   TTTGACCAGTATAAGTGCGATTGTACCCGGACAGGATTCTATGGAGAAAACTGC|TCAACA|
         ||||||  || ||||  || ||  ||||| || ||  |  |  ||       ||||||| ||
PGHS-1   CTTGACCGCTACCAGTGTGACTGCACCCGCACGGGCTATTCCGGCCCCAACTGC|ACCATC|
           160       170       180       190       200       210
            180        190       200       210       220       230
PGHS-2  |CCGGAATTTTTGACAAGAAT—AAAATTATTTCTGAAACCCA-CTCCAAACACAGTGCAC|
        ||| |  | ||||| |    |||| |||  ||||  || || ||  |||||
PGHS-1  |CCTGGCCTGTGGACCTGGCTCCGGAATT—CACTGCGGCCCAGCCCCTCTTTCA-CCCAC|
             220       230       240       250       260       270
                 240       250       260       270       280       290
PGHS-2  |TACATACTTACCCAC-TTCAAG|GGATTTTGGAACGTTGTGAATAACATTCCCTTCCTTCG
        | | || || |||    |||||  ||| || | |||   |||| ||  | || ||||| ||
PGHS-1  |TTCCTGCTCACTCACGGGCGCT|GG-TTCTGGGAGTTTGTCAATGCCA——CCTTCATCCG
            280       290       300       310       320       330
                   300       310       320       330       340
PGHS-2   A-A-ATGC|AATTATGAGTTAT-GTGTTGACA-TCCAGATCACATTTGATTGA|CAGTCCAC
         |  ||||| | | |  |   || | |||  | | ||  |  |  | |  ||| |||||| |
PGHS-1   AGAGATGC|—TCATG-CTCCTGGTACTCACAGTGC-GCTCCAACCTTATCCC|CAGTCCCC
                   340       350       360       370       380
           350       360       370       380       390       400
PGHS-2  CAACTTACAATGCTG-ACTATGGCTACAAAAGCTGGGAAGCCTTCTCCAACCTCTCCTAT
        | || |||| ||| || || || ||||| || |||||||| | |||||||||| ||||
PGHS-1  CCACCTACAACTCTGCAC-ATGACTACATCAGCTGGGAGTCTTTCTCCAACGTGAGCTAT
          390       400       410       420       430       440
              410       420       430       440       450       460
PGHS-2   TATACTAGAGCCCTTCCTC|CTGTGCCTGATGATTGCCCGACTCCCTTGGG|TGTCAAAGT
         || |||| |   |  || || |||||||||| | |||||||| ||| |||| ||||||
PGHS-1   TACACTCGTATTCTGCCCT|CTGTGCCTAAAGATTGCCCCACACCCATGGG|AACCAAAGG
           450       460       470       480       490       500
```

FIG.10A

```
              470       480       490       500       510       520
PGHS-2  AAAAAGCAGCTTCCTGAT TCAAATGAGATTGTGGAAAAATTGCTT CTAAGAAGAAAGTTC
        ||  ||||||| || ||| |  |    ||         || || ||| || || || ||||||
PGHS-1  AAGAAGCAGTTGCCAGAT GCCCAGCTCCTGGCCCGCCGCTTCCTG CTCAGGAGGAAGTTC
              510       520       530       540       550       560
              530       540       550       560       570       580
PGHS-2  ATCCCTGATCCCCAGGGCTCAAACATG ATGTTTGCATTCTTTGCCCAGCACTTCACGCAT
        || |||||  ||||||  |||  | ||| ||||||||| ||||||||| || |||||||||| ||
PGHS-1  ATCCTGACCCCCAAGGCACCAACCTC ATGTTTGCCTTCTTTGCACAACACTTCACCCAC
              570       580       590       600       610       620
              590       600       610       620       630       640
PGHS-2  CAGTTTTTCAAGAC AGATCATAAGCGAGGGCCAGCT TTCACCAACGGGC-TGGGCCATGG
        ||||| || |||| ||   |||   || || |  ||||||||| || | |||||||||||
PGHS-1  CAGTTCTTCAAAAC TTCTGGCAAGATGGGTCCTGGC TTCACCAA-GGCCTTGGGCCATGG
              630       640       650       660       670       680
              650       660       670       680       690       700
PGHS-2  GGTGGACTTAAATCATATTTACGGTGAAACTCTGGCTAGACAGCGTAAACTGCGCCTTTT
        ||| ||| ||  ||  |||||| ||| || ||||   | ||||  | |||||||||  || ||
PGHS-1  GGTAGACCTCGGCCACATTTATGGAGACAATCTGGAGCGTCAGTATCAACTGCGGCTCTT
              690       700       710       720       730       740
              710       720       730       740       750       760
PGHS-2  CAAGGATGGAAAAATGAAATATCAGATAATTGATGGAGAGATGTATCCTCCCACAGTCAA
        |||||||| ||| | || || || |||  | | ||||||||| |||||| || ||| | | |
PGHS-1  TAAGGATGGGAAACTCAAGTACCAGGTGCTGGATGGAGAAATGTACCCGCCCTCGGTAGA
              750       760       770       780       790       800
              770       780       790       800       810       820
PGHS-2  AGATACTCAGGCAGAGATGATCTACCCTCCTCAAG—TCCCTGAGCATCTACGGTTT GCT
        |||  |  |  | ||||   || ||||||| || ||||  ||    |  ||| |||
PGHS-1  AGAGGCGCCTGTGTTGATGCACTACCC-CC-GAGGCATCCCGCCCCAGAGCCAGAT GCT
              810       820       830       840       850       860
              830       840       850       860       870       880
PGHS-2  GTGGGGCAGGAGGTCTTTGGTCTGGTGCCTGGTCTGATGATGTATGCCACAATCTGGCTG
        ||||| |||||||| | ||||| ||||| || | ||||| || ||| |||||||| ||||||||
PGHS-1  GTGGGCCAGGAGGTGTTTGGGCTGCTTCCTGGGCTCATGCTGTATGCCACGCTCTGGCTA
              870       880       890       900       910       920
              890       900       910       920       930       940
PGHS-2  CGGGAACACAACAGAGT ATGCGATGTGCTTAAACAGGAGCATCCTGAATGGGGTGATGAG
        | || |||||||| || | ||  ||| |||     |   |||||| ||  ||||| ||||||
PGHS-1  CGTGAGCACAACCGTGT GTGTGACCTGCTGAAGGCTGAGCACCCCACCTGGGGCGATGAG
              930       940       950       960       970       980
              950       960       970       980       990       1000
PGHS-2  CAGTTGTTCCAGACAAGCAGGCTAATACTG ATAGGAGAGACTATTAAGATTGT GATTGAA
        ||| | |||||||||| |||||   |  || ||||| ||||| |||||||||| || ||
PGHS-1  CAGCTTTTCCAGACGACCCGCCTCATCCTC ATAGGGGAGACCATCAAGATTGT CATCGAG
              990       1000      1010      1020      1030      1040
```

FIG.10B

```
               1010      1020      1030      1040      1050      1060
PGHS-2  GATTATGTGCAACACTTGAGTGGCTATCACTTCAAACTGAAGTTTGACCCAGAACTACTT
        || ||  |||||| ||  |||||||||||| | |  |||||| |||||||||||| || ||
PGHS-1  GAGTACGTGCAGCAGCTGAGTGGCTATTTCCTGCAGCTGAAATTTGACCCAGAGCTGCTG
               1050      1060      1070      1080      1090      1100
               1070      1080      1090      1100      1110      1120
PGHS-2  TTCAACAAACAGTTCCAGTACCAAAATCGTATTGCTGCTGAATTTAACACCCTCTATCAC
        |||     ||||||||| ||||  || || |||||  | || || |||  |||||| |||
PGHS-1  TTCGGTGTCCAGTTCCAATACCGCAACCGCATTGCCACGGAGTTCAACCATCTCTACCAC
               1110      1120      1130      1140      1150      1160
               1130      1140      1150      1160      1170      1180
PGHS-2  TGGCATCCCCTTCTGCCTGACACCTTTCAA-ATTCATGACCAGAAATACAACTATCAACA
        ||||| | || |||||||| || |||||   |    |||| | |||| ||   |  | |
PGHS-1  TGGCACCCCCTCATGCCTGACTCC-TTCAAGGTGGGCTCCCAGGAGTACAGCTACGAGCA
               1170      1180      1190      1200      1210      1220
               1190      1200      1210      1220      1230      1240
PGHS-2  GTTTATCTACAACAACTCTATATTGCTGGAACATGGAATT-A---CCCAGTTTGTTGAATC
        |||  | | |||||| || ||| |   ||| ||||  ||  ||  ||| || |  ||   |
PGHS-1  GTTCTTGTTCAACACCTCCATGTTGGTGGACTATGGGGTTGAGGCCCTGGTGGATG---C
               1230      1240      1250      1260      1270
               1250      1260      1270      1280      1290
PGHS-2  ATTCACCAGGCAGATTGCTGGCAGGGTTGCTGGTGGTAGGAA-TGTTCCACCCGCAGTA
        |||  |  ||||||||||||||| |||  | | | ||||||| ||  ||| || || ||
PGHS-1  CTTCTCTCGCCAGATTGCTGGCCGGATCGGTGGGGGCAGGAACATGGACCA-CCACA-TC
               1280      1290      1300      1310      1320      1330
               1300      1310      1320      1330      1340      1350
PGHS-2  CAGAAAGTATCACAGGCTTCCATTGACCAGAGCAGGCAGATGAAATACCAGTCTTTTAAT
        | | ||  |  | |   ||| |||   ||   || || || |||| | |||  | |||
PGHS-1  CTGCATGTGGCTGTGGATGTCATCAGGGAGTCTCGGGAGATGCGGCTGCAGCCCTTCAAT
               1340      1350      1360      1370      1380      1390
               1360      1370      1380      1390      1400      1410
PGHS-2  GAGTACCGCAAACGCTTTATGC-TGAAGCCCTATGAATCATTTGAAGAACTTACAGGAGA
        ||||||||||  |  ||||  | | |||   ||   ||  ||  || |||| ||||||
PGHS-1  GAGTACCGCAAGAGGTTT-GGCATGAAACCCTACACCTCCTTCCAGGAGCTCGTAGGAGA
               1400      1410      1420      1430      1440      1450
               1420      1430      1440      1450      1460      1470
PGHS-2  AAAGGAAATGTCTGCAGAGTTGGAAGCACTCTATGGTGACATCGATGCTGTGGAGCTGTA
        ||||| ||| | | |||||||||||| | |||||| || ||| ||||| ||||| |||
PGHS-1  GAAGGAGATGGCAGCAGAGTTGGAGGAATTGTATGGAGACATTGATGCGTTGGAGTTCTA
               1460      1470      1480      1490      1500      1510
               1480      1490      1500      1510      1520      1530
PGHS-2  TCCTGCCCTTCTGGTAGAAAAGCCTCGGCCAGATGCCATCTTTCCTCAAACCATCCTACA
        ||||  || ||  | |||||||  ||| |||||| |||| | ||| |  ||| |  | |
PGHS-1  CCCTGGACTGCTTCTTGAAAAGTGCCATCCAAACTCTATCTTTGGGGAGAGTATGATAGA
               1520      1530      1540      1550      1560      1570

FIG.10C
```

```
              1540      1550      1560      1570      1580      1590
PGHS-2   ACTTGGAGCACCATTCTCCTTGAAACCACTTATGGGTAATGTTATATGTTCTCCTGCCTA
         ||||  || ||  ||  |||  | ||     ||  |  | ||  ||  ||  |||||||||  |  |||
PGHS-1   GATTGGGGCTCCCTTTTCCCTCAAGGGTCTCCTAGGGAATCCCATCTGTTCTCCGGAGTA
              1580      1590      1600      1610      1620      1630

1600      1610      1620      1630      1640      1650
PGHS-2   CTGGAAGCCAAGCACTTTTGGTGGAGAAGTGGGTTTTCAAATCATCAACACTGCCTCAAT
         ||||||||||  ||||||  ||||||  ||  ||  |||||  |||  |  |||   ||||  ||  |||  || |
PGHS-1   CTGGAAGCCGAGCACATTTGGCGGCGAGGTGGGCTTTAACATTGTCAAGACGGCCACACT
              1640      1650      1660      1670      1680      1690

1660      1670      1680      1690      1700      1710
PGHS-2   TCAGTCTCTCATCTGCAATAACGTGAAGGGCTGTCCCTTTACTTCATTCAGTGTTCCAGA
            ||     ||   ||||||     |||      |||   |||||||||         |||  |||  ||||  ||  ||
PGHS-1   GAAGAAGCTGGTCTGCCTCAACACCAAGACCTGTCCCTACGTTTCCTTCCGTGTGCCGGA
              1700      1710      1720      1730      1740      1750

1720      1730      1740      1750      1760
PGHS-2   T-CCAG---A-GCTCAT---TAAAACAGT-CACCATCAATGCA-AGTTCT-TCCCGCTCCGG
         |  ||||    |  | | | |  ||        ||  | |    |   ||  ||  || | | ||   ||   | ||
PGHS-1   TGCCAGTCAGGATGATGGGCCTGCTGTGGAGCGACCATCCACAGAGCTCTGAGGGGCAGG
              1760      1770      1780      1790      1800      1810

1770      1780      1790      1800      1810      1820
PGHS-2   ACTAGATGATATCAATCCCACACTACTACTAAAAGAACGTTCGACTGAACTGTAGAAGTC
                                                                |
PGHS-1   AAAG

1830
PGHS-2   TAATAC
```

FIG.10D

```
                                                       50
CTCGATCAAACCTTTTTTTTATGGTACACAATAGTCACAGTACTTTTCCA
                                                      100
TATAAAACAGGTTTAGTGGTCTTAATTTAGTTTGGCACATTTAATACACT
                                                      150
CCCATGACCAGCATCCCAAATGTACCTATCCGTTTTATTTTATTGTCTCA
                                                      200
GAATTGTCAGTTATTTAATAAATTATGTAACTTTTTTCCTTATGCTCAGA
                                                      250
TTTGCACTTCTTTCTAAAACTCTGCCCATCCTTAAAGTCCCAGATTCTCC
                                                      300
TTGAACTTTTTTTTTGACTTTCCAAGTACATGGAACTCTTCACTCTATC
                                                      350
CTGCTATATAAGGTGACAGAATTTCCACTATGGGATAGATGGAGTTCAAT
                                                      400
TCCTTTGAGTTTAAAATAATCTAAATATAATTATTCCTTATGCCCTGTTT
                                                      450
TTCCCTCACTTTTGTATCCAAATCTCTTTTCAGACAACAGAACAATTAAT
                                                      500
GTCTGATAAGGAAGACAATGATGATGATCACTTCAAAATGAATTCAGGAT
                                                      550
TGTAATGTAAAATTTTAGTACTCTCTCACAGTATGGATTCTAACATGGCT
                                                      600
TCTAACCCAAACTAACATTAGTAGCTCTAACTATAAACTTCAAATTTCAG
                                                      650
TAGATGCAACCTACTCCTTTAAAATGAAACAGAAGATTGAAATTATTAAA
                                                      700
TTATCAAAAAGAAAATGATCCACGCTCTTAGTTGAAATTTCATGTAAGAT
                                                      750
TCCATGCAATAAATAGGAGTGCCATAAATGGAATGATGAAATATGACTAG
                                                      800
AGGAGGAGAAAGGCTCCTAGATGAGATGGGATTTTAGGCATCCGTGTCTC
                                                      850
ATGAGGAATCAGTTGTGTCACTAGGCAAAACAGTAAAAAAAAAAACCTCC
                                                      900
AAGTGAGTCTCTTATTTATTTTTTTCTTATAAGACTTCTACAAATTGAGG
                                                      950
TACCTGGTGTAGTTTTATTTCAGGTTTTATGCTGTCATTTTCCTGTAATG
```

FIG.11A

```
                                                      1000
CTAAGGACTTAGGACATAACTGAATTTTCTATTTTCCACTTCTTTTCTGG
                                                      1050
TGTGTGTGTATATATATATGTATATATACACACACATATACATATATA
                                                      1100
TATTTTTTAGTATCTCACCCTCACATGCTCCTCCCTGAGCACTACCCATG
                                                      1150
ATAGATGTTAAACAAAAGCAAAGATGAAATTCCAACTGTCAAAATCCCCC
                                                      1200
CTCCATCTAATTAATCCCTCACCCAACTATGTTCCAAAACGAGAATAGAA
                                                      1250
AATTAGCCCCAATAAGCCCAGGCAACTGAAAAGTAAATGCTATGTTGTAC
                                                      1300
TTTGATCCATGGTCACAACTCATAATCTTGGAAAAGTGGACAGAAAAGAC
                                                      1350
AAAAGAGTGAACTTTAAAACTCGAATTTATTTTACCAGTATCTCCTATGA
                                                      1400
AGGGCTAGTAACCAAAATAATCCACGCATCAGGGAGAGAAATGCCTTAAG
                                                      1450
GCATACGTTTTGGACATTTAGCGTCCCTGCAAATTCTGGCCATCGCCGCT
                                                      1500
TCCTTTGTCCATCAGAAGGCAGGAAACTTTATATTGGTGACCCGTGGAGC
                                                      1550
TCACATTAACTATTTACAGGGTAACTGCTTAGGACCAGTATTATGAGGAG
                                                      1600
AATTTACCTTTCCCGCCTCTCTTTCCAAGAAACAAGGAGGGGGTGAAGGT
                                                      1650
ACGGAGAACAGTATTTCTTCTGTTGAAAGCAACTTAGCTACAAAGATAAA
                                                      1700
TTACAGCTATGTACACTGAAGGTAGCTATTTCATTCCACAAAATAAGAGT
                                                      1750
TTTTTAAAAAGCTATGTATGTATGTGCTGCATATAGAGCAGATATACAGC
                                                      1800
CTATTAAGCGTCGTCACTAAAACATAAAACATGTCAGCCTTTCTTAACCT
                                                      1850
TACTCGCCCCAGTCTGTCCCGACGTGACTTCCTCGACCCTCTAAAGACGT
                                                      1900
ACAGACCAGACACGGCGGCGGCGGCGGGAGAGGGATTCCCTGCGGCCCC
```

FIG.11B

```
                                                    1950
GGACCTCAGGGCCGCTCAGATTCCTGGAGAGGAAGCCAAGTGTCCTTCTG
                                                    2000
CCCTCCCCCGGTATCCCATCCAAGGCGATCAGTCCACAACTGGCTCTCGG
                                                    2050
AAGCACTCGGGCAAAGACTGCGAAGAAGAAAAGACATCTGGCGGAAACCT
                                                    2100
GTGCGCCTGGGGCGGTGGAACTCGGGGAGGAGAGGGAGGGATCAGACAGG
                                                    2150
AGAGTGGGGACTACCCCCTCTGCTCCCAAATTGGGGCAGCTTCCTGGGTT
                                                    2200
TCCGATTTTCTCATTTCCGTGGGTAAAAAACCCTGCCCCCACCGGCTTAC
                                                    2250
GCAATTTTTTTAAGGGGAGAGGAGGGAAAAATTTGTGGGGGGTACGAAAA
                                                    2300
GGCGGAAAGAAACAGTCATTTCGTCACATGGGCTTGGTTTTCAGTCTTAT
                                                    2350
AAAAAGGAAGGTTCTCTCGGTTAGCGACCAATTGTCATACGACTTGCAGT
                                                    2400
GAGCGTCAGGAGCACGTCCAGGAACTCCTCAGCAGCGCCTCCTTCAGCTC
```

FIG.11C

SCREENING ASSAYS FOR INHIBITORS OF MAMMALIAN PROSTAGLANDIN H SYNTHASE-2

This is a division of application Ser. No. 08/487,752, filed Jun. 7, 1995, which is a continuation-in-part of Ser. No. 08/231,456, filed Apr. 20, 1994, now abandoned which is a continuation-in-part of Ser. No. 08/054,364, filed Apr. 28, 1993, now abandoned which is a continuation-in-part of Ser. No. 07/983,835, filed Dec. 1, 1992 (abandoned), which is a continuation-in-part of Ser. No. 07/949,780, filed Sep. 22, 1992 (abandoned); and is also a continuation-in-part of Ser. No. 08/034,143, filed Mar. 22, 1993, now abandoned which is a continuation of U.S. patent application Ser. No. 07/949,780, filed Sep. 22, 1992, now abandoned each which is incorporated by reference in its entirety.

This invention was made with government support under grant number DK 16177, awarded by the National Institutes of Health. The government has certain rights in the invention.

TABLE OF CONTENTS

1. Introduction
2. Background of the Invention
3. Summary of the Invention
    3.1. Definitions
4. Description of the Drawings
5. Detailed Description of the Invention
    5.1. DNA Encoding Mammalian PGHS-2
    5.2. Expressing the PGHS-2 Gene Product
        5.2.1. Construction of Expression Vectors and Preparation of Transfectants
        5.2.2. Identification of Transfectants or Transformants Expressing the PGHS-2 Gene Product
        5.2.3. Cell Lines Expressing PGHS-1 or PGHS-2
        5.2.4 Purification of the PGHS-2 Gene Product
    5.3. Antibodies to the PGHS-2 Gene Product
    5.4. Diagnostics
    5.5. Gene Therapies Based on the PGHS-2 Gene
    5.6. Drug Screening Assays
    5.7. Compounds Identified in the Screens
    5.8. Pharmaceutical Formulations and Routes of Administration
        5.8.1. Effective Dosage
        5.8.2. Composition and Formulation
        5.8.3. Routes of Administration
        5.8.4. Packaging
6. EXAMPLE: Isolation, Cloning, and Sequencing of Murine PGHS-2
    6.1. Materials and Methods
        6.1.1. Cells and Cell Cultures
        6.1.2. Determination of Cyclooxygenase Activity
        6.1.3. RNA Preparation
        6.1.4. cDNA Synthesis
        6.1.5. In Vitro Transcription, In Vitro Translation, Immunoprecipitation, and Primer Extension
        6.1.6. cDNA Expression and $PGE_2$ Determination
        6.1.7. Northern Blot Analysis
        6.1.8. Expressions of PGHS-2 in Human Monocytes
    6.2. Results
        6.2.1. Identification and Characterization of PGHS-2
        6.2.2. PGHS-2 cDNA Expression in COS Cells Produced a Functional Prostaglandin H Synthase
        6.2.3. Dexamethasone Specifically Reduces Expression of PGHS-2 and not PGHS-1 in Human Monocytes
7. EXAMPLE: Drug Assays Using PGHS-2 Transfectants
    7.1. Materials and Methods
        7.1.1. Expression Vector Construction
        7.1.2. Transfection and Establishment of Stable Cell Lines
        7.1.3. Drug Screening Studies
    7.2. Results
        7.2.1. Expression Vectors
        7.2.2. Cell Line Characterization
        7.2.3. Stability of $PGE_2$ Production
        7.2.4. Drug Screening Studies
8. EXAMPLE: Preparation of Microsomal Extracts and In Vitro Testing of Cyclooxygenase Activity
EXAMPLE: Isolation, Cloning and Sequencing of Human PGHS-2
    9.1. Materials and Methods
        9.1.1. Generation of Human PGHS-1 and Human PGHS-2 cDNA Clones
        9.1.2. Generation of Plasmid Constructs for Transfection and Sequencing
        9.1.3. Generation of Stably Transfected Mammalian Cell Lines
        9.1.4. Testing the G418 Resistant Cell Lines and Confirming the Stable Expression of PGHS-2 and PGHS-1 Activity
    9.2. Results
        9.2.1. Sequence of Human PGHS-2
        9.2.2. Transformed Cell Lines Stably Expressed PGHS-1 and PGHS-2
10. EXAMPLE: Nonsteroidal Anti-Inflammatory Drug (NSAID) Studies on Stable Human PGHS-1 and PGHS-2 Cell Lines
11. Deposit of Microorganisms

INTRODUCTION

The present invention relates to the gene encoding the mammalian prostaglandin H synthase-2, hereinafter "PGHS-2," and its product. Mammalian prostaglandin H synthase-1, hereinafter "PGHS-1," is responsible for the constitutive prostaglandin synthesis in mammalian physiology. PGHS-2 was discovered to be responsible for the increased prostaglandin synthesis associated with inflammation. The invention relates to PGHS-2 and to compounds which specifically modulate the expression of PGHS-2 and not PGHS-1 including but not limited to nucleic acid encoding PGHS-2 and homologues, analogues, and deletions thereof, as well as antisense, ribozyme, triple helix, antibody, and polypeptide molecules and small inorganic molecules. The invention further relates to methods of diagnosing an aberrant PGHS-2 gene and gene product as well as gene therapies for use as a remedy for such aberrant PGHS-2 gene or gene product. In addition, the invention relates to pharmaceutical formulations and routes of administration for such remedies.

2. BACKGROUND OF THE INVENTION

Prostaglandins (which include $PGE_2$, $PGD_2$, $PGF_{2\alpha}$, $PGI_2$ and other related compounds) represent a diverse group of autocrine and paracrine hormones that are derived from the metabolism of fatty acids. They belong to a family of naturally occurring eicosanoids (prostaglandins, thromboxanes and leukotrienes) which are not stored as such in cells, but are biosynthesized on demand from arachidonic acid, a 20-carbon fatty acid that is derived from the breakdown of cell-membrane phospholipids. Under normal circumstances, the eicosanoids are produced at low levels to serve as important mediators of many and diverse cellular functions which can be very different in different types of cells. However, the prostaglandins also play critical roles in pathophysiology. In particular, inflammation is both initiated and maintained, at least in part, by the overproduction of prostaglandins in injured cells. The central role that prostaglandins play in inflammation is underscored by the fact that those aspirin-like non-steroidal anti-inflammatory drugs (NSAIDS) that are most effective in the therapy of many pathological inflammatory states all act by inhibiting prostaglandin synthesis. Unfortunately, the use of these drugs is often limited by the side effects (gastrointestinal bleeding, ulcers, renal failure, and others) that result from the undesirable reduction in prostaglandins in normal cells that now suffer from a lack of those autocrine and paracrine functions that are required for the maintenance of normal physiology. The development of new agents that will act more specifically by achieving a reduction in prostaglandins in inflamed cells without altering prostaglandin production in other cells is one of the major goals for future medicinal therapy.

The cyclooxygenase reaction is the first step in the prostaglandin synthetic pathway; an enzyme (PGHS) with prostaglandin G/H synthetic activity converts arachidonic acid into the endoperoxide $PGG_2$, which then breaks down to $PGH_2$ (the two reactions are carried out by a single enzyme). $PGH_2$ is in turn metabolized by one or more prostaglandin synthase ($PGE_2$ synthase, $PGD_2$ synthase etc.) to generate the final "2-series" prostaglandins, $PGE_2$, $PGD_2$, $PGF_{2\alpha}$, $PGI_2$ and others which include the thromboxanes, $TXA_2$. The first step (PGHS) is the one that is rate-limiting for prostaglandin synthesis. As such, the PGHS-mediated reaction is the principal target for anti-inflammatory drug action; and it is inhibition of PGHS activity that accounts for the activity of the NSAIDS (aspirin, acetominophen, ibuprofen, naproxen, indomethacin) and others that limit the overproduction of prostaglandins in inflammation (the desired therapeutic goal) and reduce the normal production of prostaglandins in uninflamed cells (which produces the undesirable side effects).

In addition to the abnormal changes associated with inflammation, multiple other factors are known to influence prostaglandin production under experimental conditions. These include growth factors, cAMP, tumor promoters, src activation and interleukins 1 and 2, all of which increase overall cellular PGHS activity. The adrenal glucocorticoid hormones and related synthetic anti-inflammatory steroids also inhibit prostaglandin synthesis, but their metabolic site of action is not well defined.

Human, ovine, and murine cDNAs have been cloned for PGHS-1. All show similar sequences and hybridize with 2.8–3.0-kb mRNAs on Northern blots. However, several research groups have recently identified and predicted the sequence of a protein reported to be related to PGHS-1 in some manner. In 1990, Han et al., 1990, Proc. Nat'l. Acad. Sci. USA, 87:3373–3377 reported changes in protein synthesis caused by the polypeptide $pp60^{v-src}$, following infection of BALB/c 3T3 fibroblasts by Rous sarcoma virus temperature-sensitive mutant strain LA90. Giant two-dimensional gel electrophoresis detected induction of a 72–74 kDa protein doublet that is recognized by anticyclooxygenase antibodies. Synthesis of this doublet was also transiently increased by exposure to platelet-derived growth factor and inhibited by dexamethasone treatment. These changes in protein synthesis were strongly correlated with changes in cyclooxygenase activity. The protein doublet was also seen in mouse C127 fibroblasts where its synthesis was found to be regulated by serum and dexamethasone and correlated with cyclooxygenase activity. See O'Banion et al., 1991, J. Biol. Chem., 266:23261–23267.

Xie et al., 1991, Proc. Nat'l. Acad. Sci. USA, 2692–2696 followed Han's et al. earlier report with the isolation of a set of cDNAs corresponding to $pp60^{v-arc}$ inducible form "$miPGHS_{ch}$", for mitogen-inducible $PGHS_{chicken}$. Although Xie et al. speculated that prostaglandin synthesis may play a role in src product-mediated cellular transformation, their experiments did not permit them to discriminate between $miPGHS_{ch}$ as a second cyclooxygenase or simply as the chicken homolog of sheep PGHS-1, "$PGHS_{ov}$".

In a separate set of experiments, Kujubu et al., 1991 J. Biol. Chem., 266:12866–12872 reported that one of the primary response genes cloned from mitogen-responding Swiss 3T3 cells (TIS10) has a long 3'-untranslated region and encodes a "predicted" 66 kDa protein which is about 60% identical to mouse PGHS-1. The sequence of this putative protein was essentially identical to that derived by Xie et al. On the basis of sequence similarities, Kujubu et al. speculated that the enzymatic activity of the protein encoded by the TIS10 gene would be likely to be "similar" to enzymatic activity of other types of mammalian PGHS-1. They concluded that "[p]roof of this conjecture, however, awaits the heterologous expression of this gene production from an expressible plasmid and the direct measurement of cyclooxygenase activity in transfected cells and/or purified preparations of the TIS10 protein."

There is increasing emphasis on the development of methods for the modulation and evaluation of the activity of the prostaglandin synthetic pathway. As noted above, non-steroidal anti-inflammatory agents, such as aspirin and indomethacin, inhibit the cyclooxygenase which converts arachidonic acid into $PGG_2$ and $PGH_2$. Therefore, there is a need for improved methods to study the effectiveness of existing anti-inflammatory drugs and to evaluate the effectiveness of potential anti-inflammatory agents, at the molecular level, as well as for reagents for use in such methods.

3. SUMMARY OF THE INVENTION

The invention relates to the gene encoding the mammalian prostaglandin H synthase-2 and its product. The invention is based, in part, on the discovery that there are two PGHS genes; one constituitively expressed and termed herein PGHS-1, and a second which is responsive to regulatory control and termed herein PGHS-2. More specifically, the invention relates to the diagnosis of an aberrant PGHS-2 gene or gene product; the identification, production, and use of compounds which modulate PGHS-2 gene expression or the activity of the PGHS-2 gene product including but not limited to nucleic acid encoding PGHS-2 and homologues, analogues, and deletions thereof, as well as antisense, ribozyme, triple helix, antibody, and polypeptide molecules and small inorganic molecules; and pharmaceutical formulations and routes of administration for such compounds. The invention also relates to the identification of naturally occurring cells and the creation of cells that express PGHS-1 or PGHS-2 exclusively and the use of such cells in drug screening.

In the examples described infra, it is shown that a second PGHS gene, PGHS-2, has been identified in mouse and in human cells which is distinct from the PGHS-1 gene. It is further shown that PGHS-2 expression is responsive to regulatory control while PGHS-1 expression is constitutive. An assay employing PGHS-2 transfectants was used to successfully identify compounds which modulate the expression of the PGHS-2 gene. Assays for the activity of the PGHS-2 gene product are also described. In addition assays employing PGHS-2 and PGHS-1 transfectants are described for use in identifying compounds which modulate the expression of the PGHS-2 gene and not the PGHS-1 gene.

3.1. DEFINITIONS

As used herein, the following terms and abbreviations shall have the meanings indicated below:

| | |
|---|---|
| base pair(s) | bp |
| complementary DNA | cDNA |
| counts per minute | cpm |
| deoxyribonucleic acid | DNA |
| kilobase pairs | kb |
| kilodation | kDa |
| micrograms | µg |
| micrometer | µm |
| nanograms | ng |
| nanometer | nm |
| nucleotide | nt |
| polyacrylamide gel electrophoresis | PAGE |
| polymerase chain reaction | PCR |
| prostaglandin H syntnase | PGHS |
| radioimmunoassay | RIA |
| ribonucleic acid | RNA |
| sodium dodecyl sulfate | SDS |
| units | u |

As used herein, the word "modulate" shall have its usual meaning, but shall also encompass the meanings of the words enhance, inhibit, and mimic. In addition, as used herein, the word "expression" when used in connection with a gene such as PGHS-2 shall have its usual meaning, but shall also encompass the transcription of the gene, the longevity of functional mRNA transcribed from the gene, the translation of that mRNA, and the activity of the gene product.

4. DESCRIPTION OF THE DRAWINGS

FIG. 1 depicts the cDNA (SEQ ID NO:1) and predicted amino acid sequence (SEQ ID NO:2) of murine griPGHS ("PGHS-2"). The standard one letter code for amino acids is used. Based on a transcription start site determined by primer extension at −24, the numbering of this sequence starts at 25. A predicted signal peptide cleavage site between amino acids 17 and 18 is marked with an arrowhead. The position of the putative aspirin-modified serine is indicated by a circle, and potential N-glycosylation sites are double underlined.

FIG. 2 is a schematic depiction comparing the cDNA and protein sequences for the murine 2.8- and 4.1 kb RNA-encoded cyclooxygenases. cDNA structures for the 4.1 kb cDNA cloned from C127 cells and the murine 2.8 kb cDNA are drawn as the thick lines at top and bottom. The numbering of the 4.1 kb cDNA is based on primer extension data. Since the 5' end of the 2.8 kb mouse mRNA has not been determined, no numbers have been assigned to the translation start and stop sites. Alternative polyadenylation sites established from other cDNA clones are indicated with "A" and the 5'-AUUU$_n$A-3' motifs are identified by dots underneath the sequence. These motifs are not found in the 2.8 kb cDNA. Deduced protein sequences are drawn colinearly with gaps (17 aa at the amino-terminal end of the 4.1 kb mRNA product, and 18 aa at the carboxy-terminal end of the 2.8 kb mRNA product) indicated by connecting lines. The 26 aa leader sequence for the 2.8 kb PGHS is indicated. Although its extent has not been precisely defined, a shorter, nonhomologous leader appears to exist for griPGHS with a mature N-terminal end at amino acid 18. The positions of potential N-glycosylation sites (NXS/T, "N") and the conserved aspirin modified serines are noted on each molecule. The hatched areas near the center of each molecule denote presumed axial (TIWLREHNRV, identical between the two molecules) and distal (KALGH/RGLGH) heme-binding sites as suggested by DeWitt et al., 1990, J. Biol. Chem. 265:5192–5198. Interestingly, the RGLGH sequence in griPGHS fits the consensus RXXXH (SEQ ID NO:18) distal heme-binding site described for other peroxidases, Kimura and Ikeda-Saito, 1988, Prot. Struc. Func. Genetics 113–120, and supports the previous suggestion that KALGH serves the same purpose in the 2.8 kb gene product, DeWitt et al., 1990, J. Biol. Chem. 265-5192–5198. The bar at the bottom of the figure represents the similarities between the two mouse PGHS proteins (omitting the nonconserved N- and C-termini) as the percentage of identical residues for groups of 20 amino acids with increasing shading indicating 40–55% (no shading), 60–75%, 80–95%, and 100% identity. The overall identity is 64% and with conservative changes the similarity index is 79%.

Figure 3A:
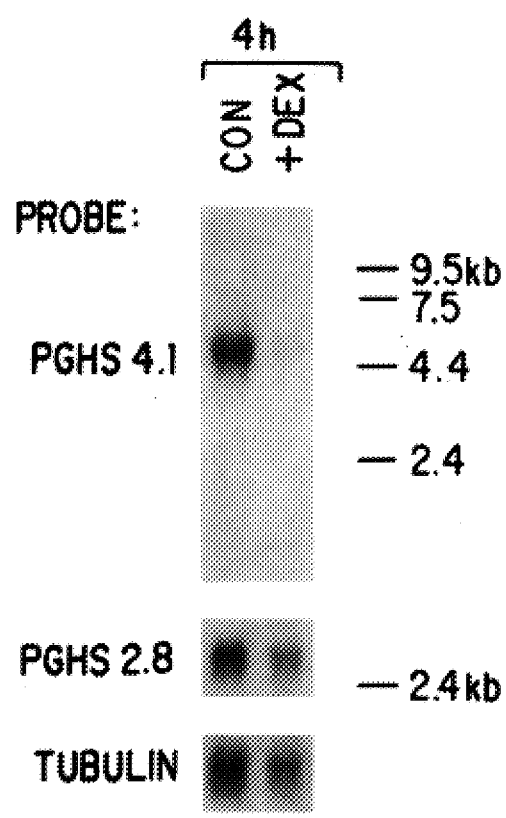
Figure 3B:
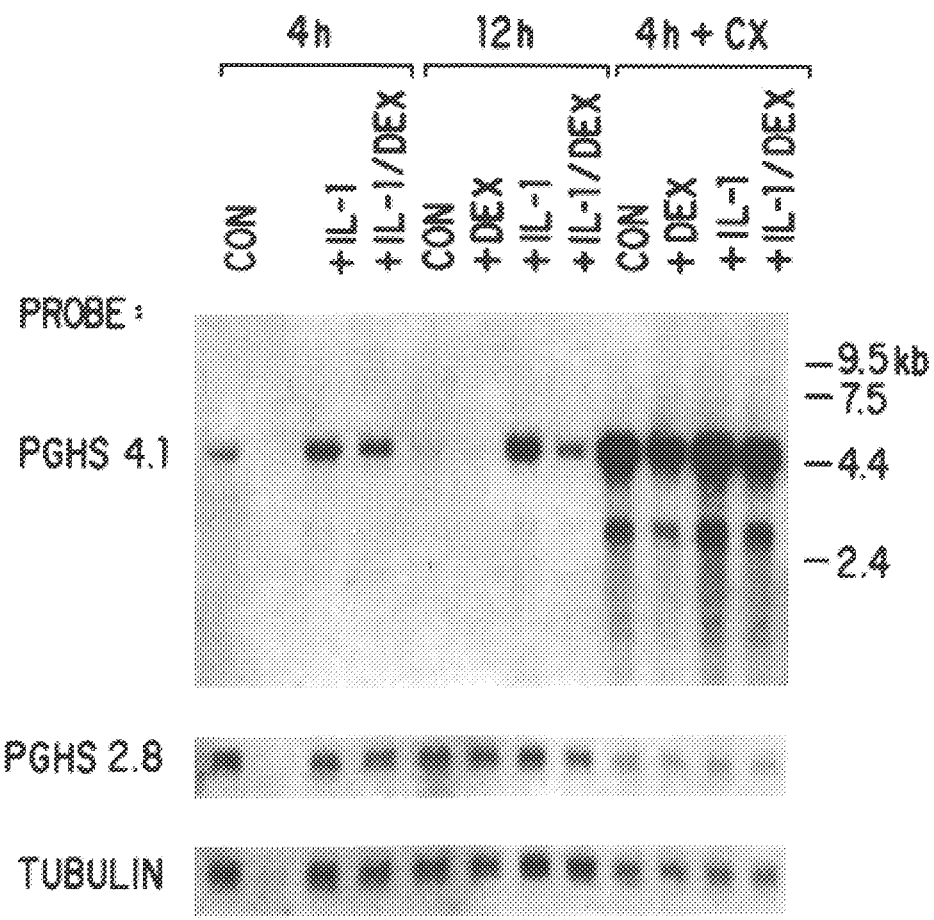

FIGS. 3A–3B are a photographic depiction of autoradiographies obtained by Northern blotting monitoring the expression of the genes encoding griPGHS and the constitutive PGHS-1, as expressed in human monocytes, in response to interleukin-1 treatment, a known mediator of inflammation. Adherent human monocytes isolated from healthy donors were suspended in medium without serum at $1\times10^6$ cells/ml. One ml aliquots in 5 ml polypropylene tubes were incubated with loosened caps in 5% $CO_2$ at 37° C. with occasional shaking. FIGS. 3A–3B are more fully described as follows:

FIG. 3A: Monocytes were incubated for 4 h in the presence or absence of dexamethasone (1 µM) prior to total RNA isolation. Five µg was subjected to Northern blot analysis with the indicated probes.

FIG. 3B: Monocytes were treated with dexamethasone (1 µM), 1L-1β (10 half-maximal units, Collaborative Research), or both for the indicated times prior to RNA isolation. Cycloheximide (25 µM) was added to one set of incubations 15 min prior to he addition of cytokine or hormone.

Figure 4:
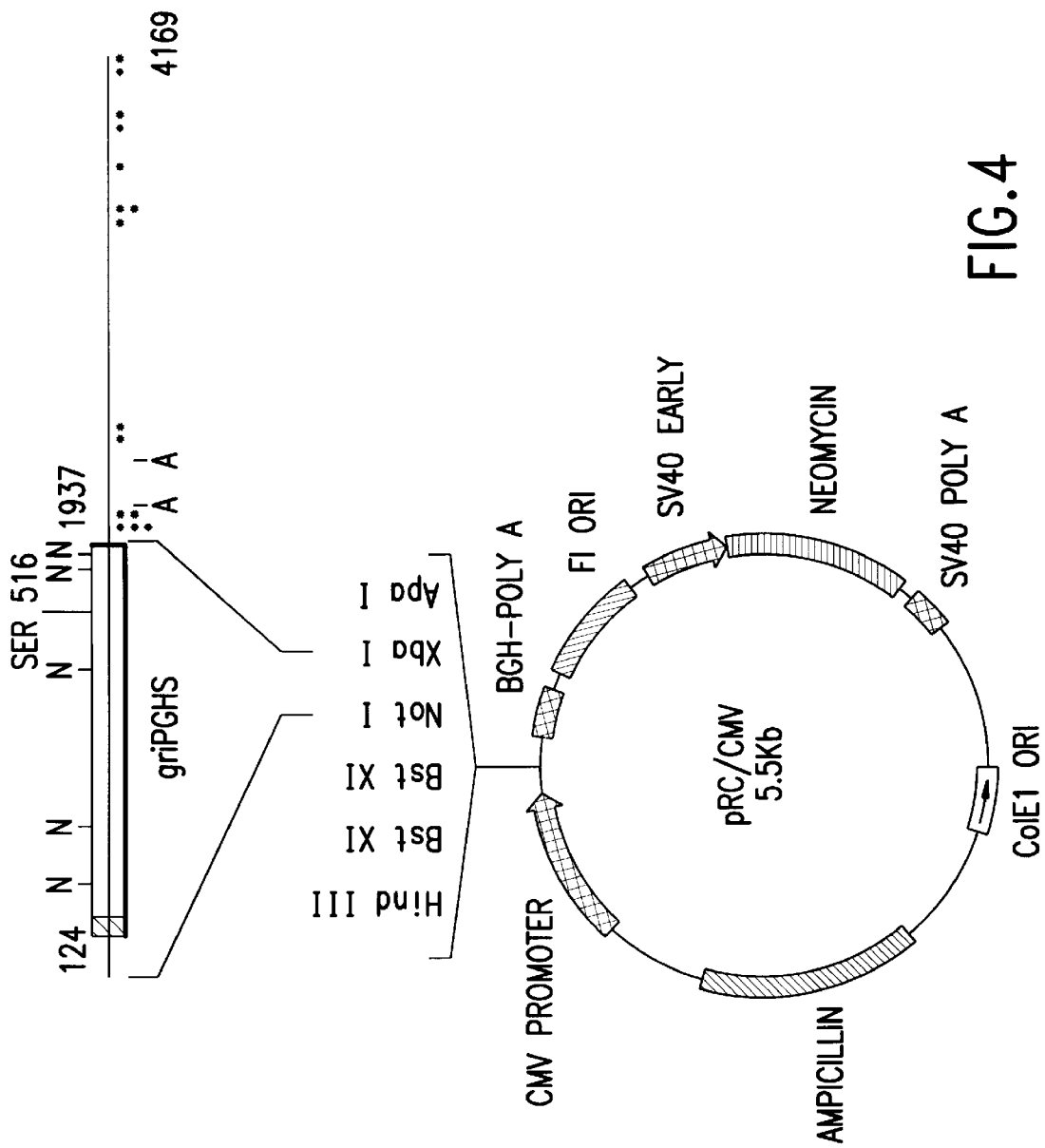

FIG. 4 is a schematic depiction of griPGHS expression vector construction. griPGHS was prepared for directional subcloning into the pRC/CMV expression vector (Invitrogen) by digestion with Acc I, Klenow fill-in, and digestion with Not I. This fragment, extending from the Not I site 50 bases upstream of the cDNA end to nt 1947 of the cDNA, contains the full-coding region truncated immediately before any 5'-AUUUA-3' mRNA destabilizing regions, O'Banion et al., 1992, Proc. Nat'l. Acad. Sci. USA, 89:4888–4892. The pRc/CMV vector DNA was digested with Xba I, filled in with Klenow, then digested with Not I. The dots in the 3' untranslated region of griPGHS indicate the locations of 5'-AUUUA'-3'mRNA destabilizing sequences. "A" represents alternative polyadenylation sites, "N" represents potential glycosylation sites, and "SER 516" marks the location of the aspirin-acetylated serine.

Figure 5A:
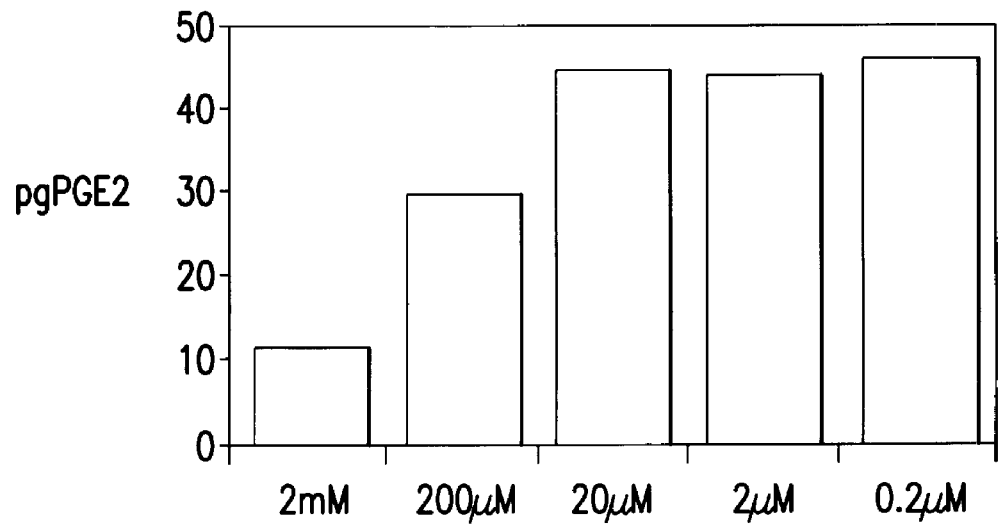

FIGS. 5A–5D are a graphic depiction of the inhibition of murine griPGHS activity in stable transfected mammalian cell lines by preselected amounts of several non-steroidal anti-inflammatory drugs. FIGS. 5A–5D are more fully described as follows:

FIG. 5A: Acetominophen.

Figure 5B:
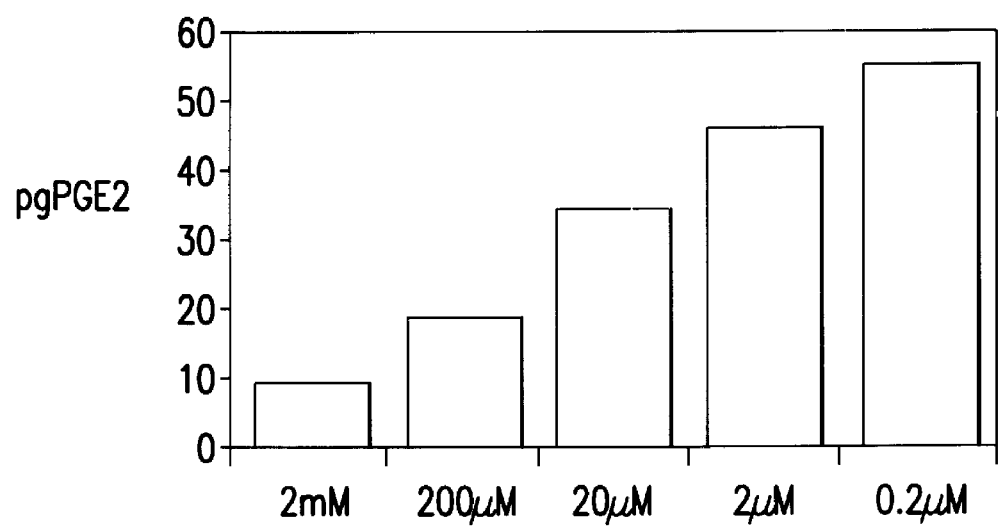
Figure 5C:
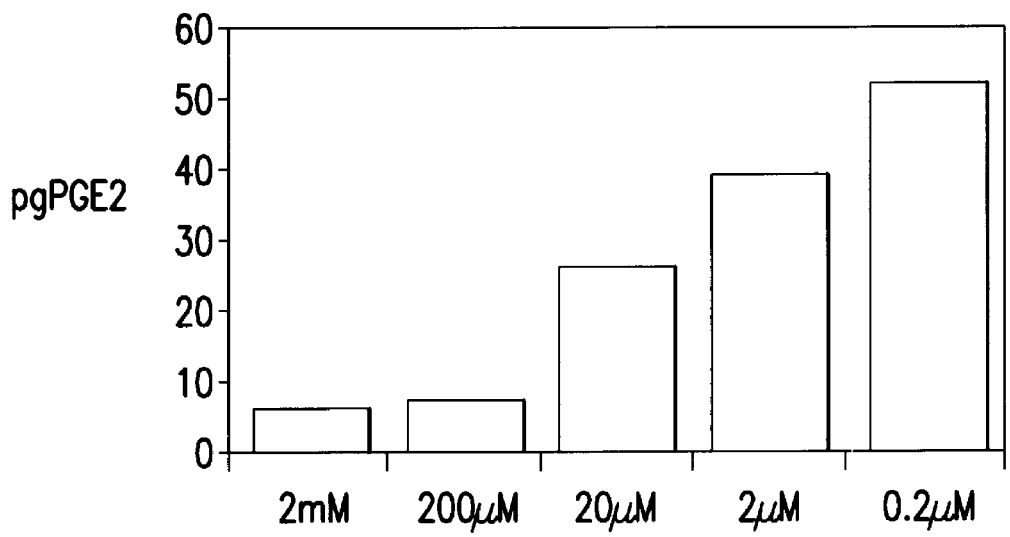

FIG. 5B: Ibuprofen.

FIG. 5C: Naproxen.

Figure 5D:
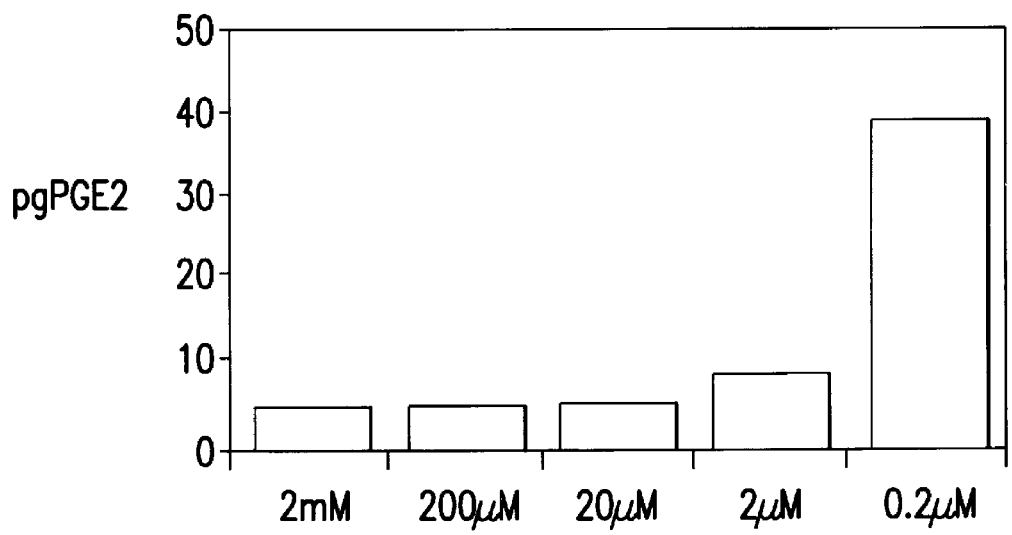

FIG. 5D: Indomethacin.

FIGS. 6A–6B depict the nucleotide sequence of the human PGHS-2 gene (SEQ ID NO:3). FIGS. 6A–6B are more fully described as follows:

FIG. 6A: Nucleotides 90–1049.

FIG. 6B: Nucleotides 1050–1923.

FIG. 7 depicts a comparison between the amino acid sequence of human PGHS-2 of the present invention (upper sequence) (SEQ ID NO:4) and the amino acid sequence published by Hla et al. (lower sequence) (SEQ ID NO:5). The sequences are given in standard single letter code.

Figure 8A:
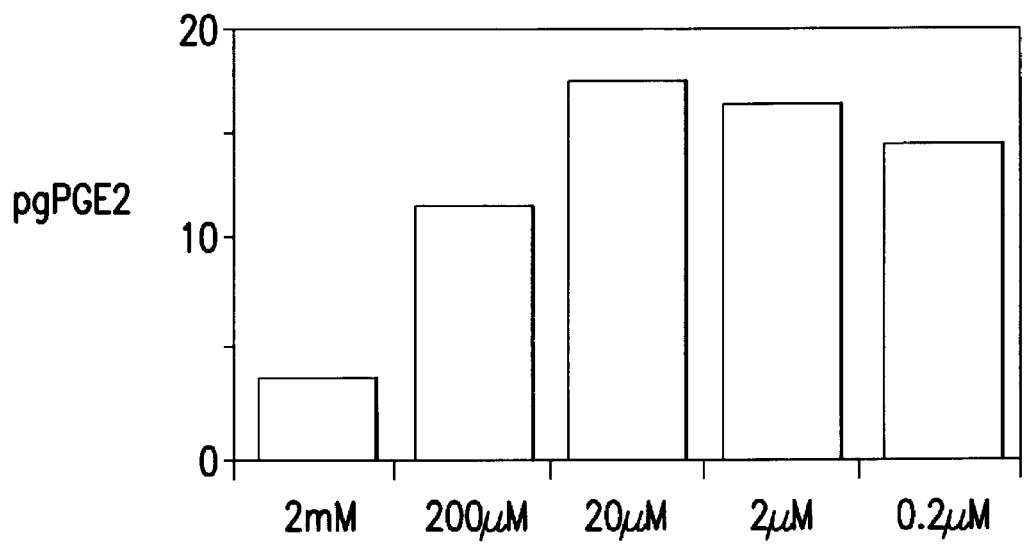

FIGS. 8A–8D are a graphical depiction of the inhibition of human PGHS-2 activity in stably transformed COS cells by four non-steroidal anti-inflammatory drugs (NSAID): Acetominophen; Ibuprofen; Naproxen; and Indomethacin. FIGS. 8A–8D are more fully described as follows:

FIG. 8A: Acetominophen.

Figure 8B:
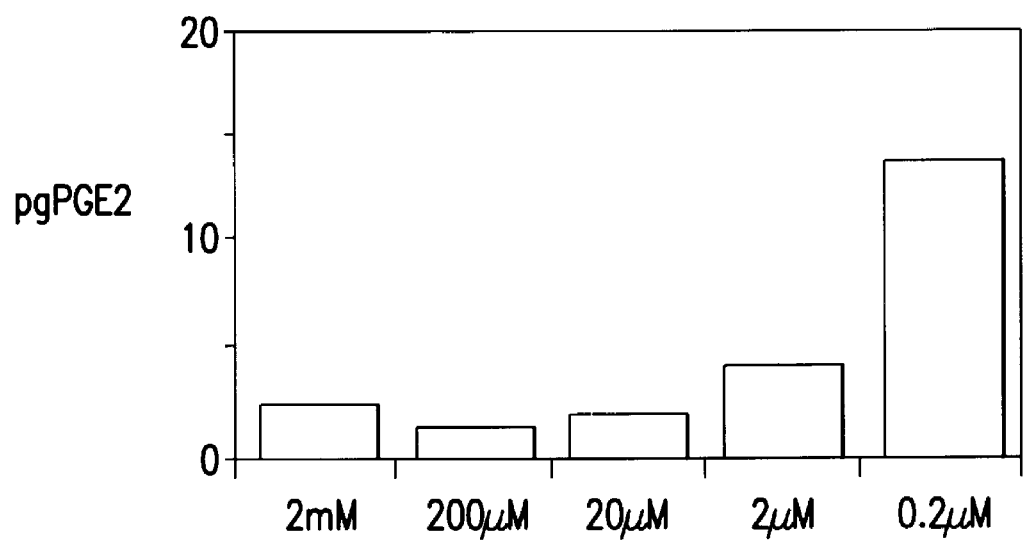
Figure 8C:
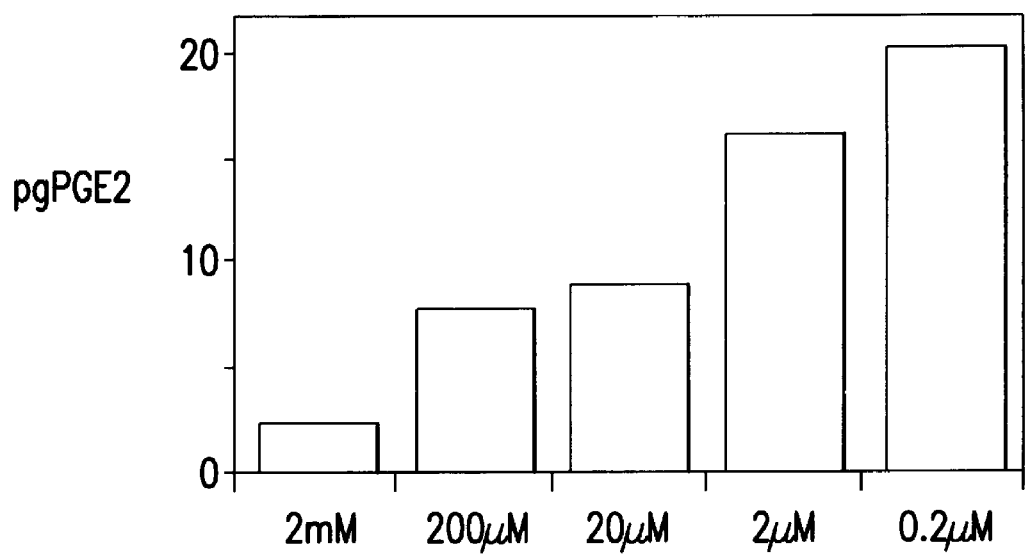

FIG. 8B: Ibuprofen.

FIG. 8C: Naproxen.

Figure 8D:
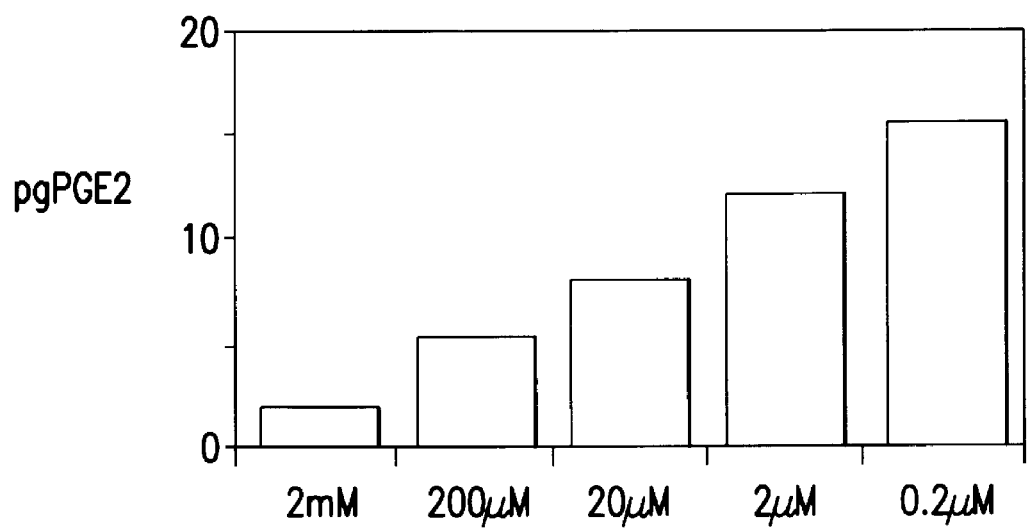

FIG. 8D: Indomethacin.

Figure 9A:
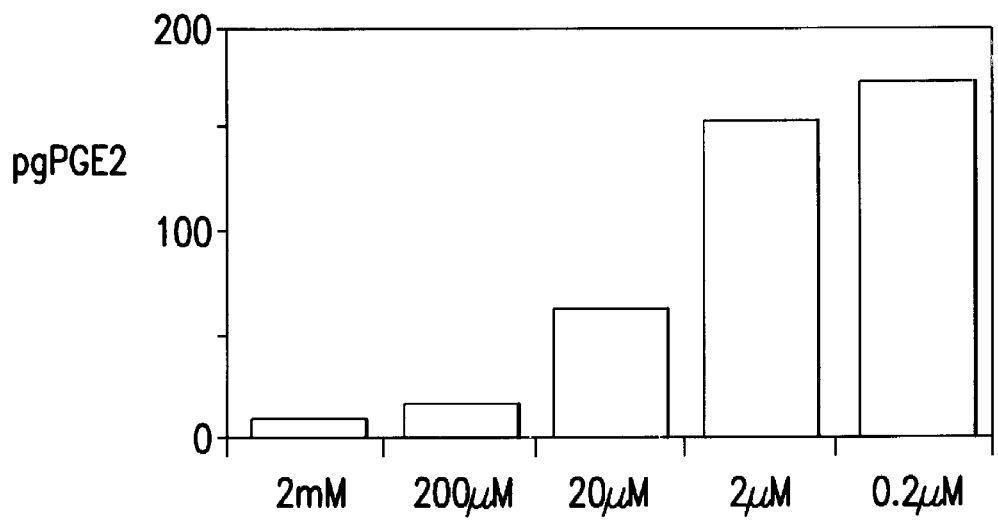

FIGS. 9A–9D are a graphical depiction of the inhibition of human PGHS-1 activity in stably transformed COS cells by four NSAID: Acetominophen; Ibuprofen; Naproxen; and Indomethacin. FIGS. 9A–9D are more fully described as follows:

FIG. 9A: Acetominophen.

Figure 9B:
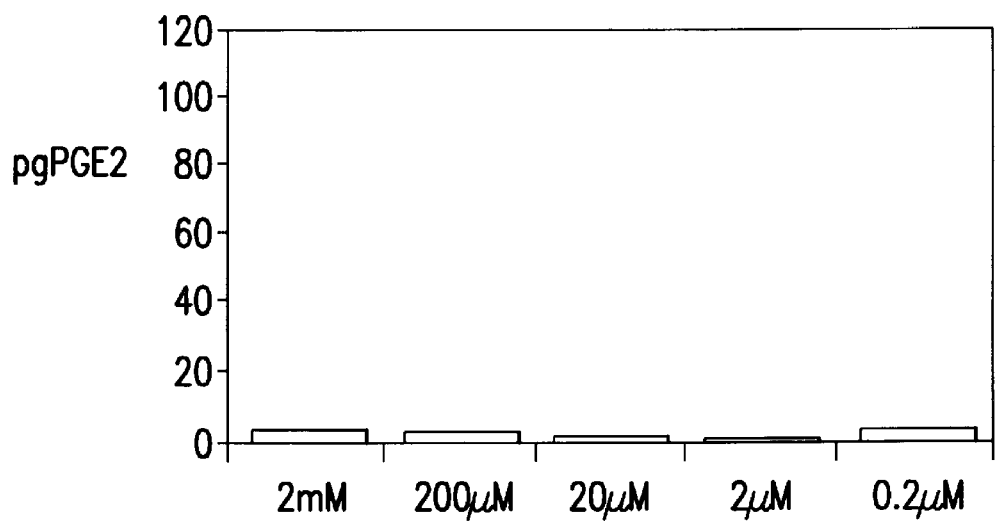
Figure 9C:
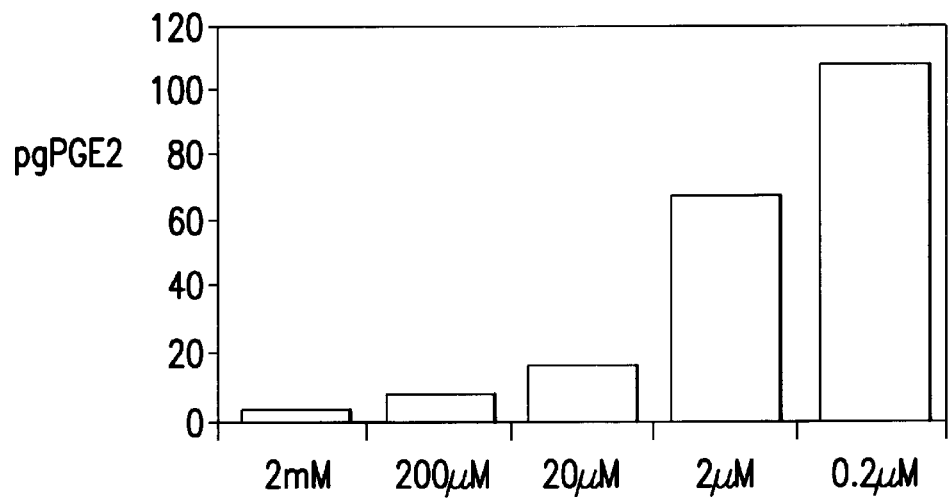

FIG. 9B: Ibuprofen.

FIG. 9C: Naproxen.

Figure 9D:
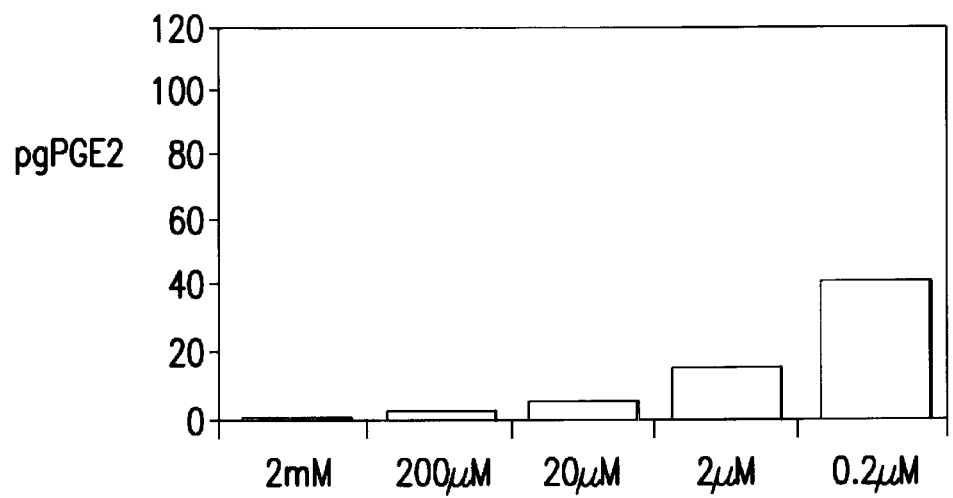

FIG. 9D: Indomethacin.

FIGS. 10A–10D show a nucleic acid sequence comparison between the coding regions of human PGHS-2 (SEQ ID NO:14) and PGHS-1 (SEQ ID NO:6). Solid-lined-boxes indicate regions where the sequence of PGHS-2 is least homologous to that of PGHS-1. Dashed-lined-boxes indicate regions where the sequence of PGHS-2 is most homologous to that of PGHS-1. FIGS. 10A–10D are more fully described as follows:

FIG. 10A: PGHS-2 nucleotides 1–467.

FIG. 10B: PGHS-2 nucleotides 469–1004.

FIG. 10C: PGHS-2 nucleotides 1006–1537.

FIG. 10D: PGHS-2 nucleotides 1540–1834.

FIGS. 11A–11C show the nucleic acid sequence of the 5' promoter region of human PGHS-2 (SEQ ID NO:15) as compared with that of PGHS-1. Dashed-lined-boxes indicate the regions where the sequence of the PGHS-2 5' region is most homologous to that of PGHS-1. FIGS. 11A–11C are more fully described as follows:

FIG. 11A: PGHS-2 promoter nucleotides 1–950.

FIG. 11B: PGHS-2 promoter nucleotides 951–1900.

FIG. 11C: PGHS-2 promoter nucleotides 1901–2400.

5. DETAILED DESCRIPTION OF THE INVENTION

The present invention provides a mammalian cell line which contains a chromosomally integrated, recombinant DNA sequence, which DNA sequence expresses mammalian, preferably human, glucocorticoid-regulated inflammatory PGHS, and which cell line does not significantly express autologous PGHS-1 or PGHS-2 activity. For brevity, glucocorticoid-regulated inflammatory PGHS will hereinafter be referred to as "griPGHS" or "PGHS-2", and the art-recognized mammalian PGHS encoded by the 2.8–3.0 kb mRNA (EC 1.14.99.1) will be referred to as -constitutive cyclooxygenase," or "constitutive PGHS," or "PGHS-1." The recitation that there is no "autologous PGHS-1 or PGHS-2 activity" relates to the inability of the cell line to express PGHS activity apart from that expressed by the recombinant DNA sequence. Autologous PGHS activity may also be referred to as "endogenous" PGHS activity in the art.

This invention is a result, in part, of the discovery that the 72–74 kDa cyclooxygenase reported by Han et al., the miPGHS$_{ch}$ reported by Xie et al., and the TIS10 protein reported by Kujubu et al. are essentially identical and represent a second cyclooxygenase, which second form is the primary target for inhibition by glucocorticoids and is also a target for inhibition by non-steroidal anti-inflammatory agents.

The synthesis of a 70 kilodalton (kDa) protein in C127 mouse fibroblasts, via a mouse 4 kilobase (kb) mRNA, and the derived amino acid sequence was reported. The protein encoded by the 4-kb mRNA shows 80% amino acid identify with the previously known mouse PGHS-1 protein product in a sequenced 240 base region. See O'Banion et al., 1991, J. Biol. Chem., 35:23261–23267.

The 70 kDa protein, designated griPGHS or PGHS-2 herein, was determined to be a discrete form of cyclooxygenase by several assays. The protein was precipitated by anti-PGHS serum, its synthesis and concomitant cyclooxygenase levels are rapidly induced by serum, and the induction is inhibited by dexamethasone. The regulation of PGHS-2 synthesis was found not to arise from alterations in the level of the 2.8-kb PGHS-1 mRNA, but resulted from changes in the level of a 4-kb mRNA species. This latter species is barely detectable with a 2.8-kb PGHS-1 DNA probes in cells treated with serum, but accumulates to significant levels in cells treated with cycloheximide or calcium ionophores. In contrast, there was no change in the level of, the 2.8-kb mRNA which encodes PGHS-1 or "constitutive PGHS" as observed following treatment with serum, dexamethasone or cycloheximide. Finally, by hybridization analysis, it was shown that the 4-Kb mRNA represented the product of a gene that is distinct from the gene giving rise to the 2.8-Kb mRNA.

These observations indicated that there are two cyclooxygenase genes; one constitutively expressed as a 2.8-kb mRNA, and a second giving rise to a growth factor and glucocorticoid-regulated 4-kb mRNA which encodes PGHS-2. It is believed that expression of the latter 4-kb RNA and concomitantly increased PGHS-2 levels are primarily, if not entirely, responsible for the enhanced prostaglandin synthesis that is responsible, directly or indirectly, for many of the adverse effects of inflammation.

The primary and perhaps sole action of most non-steroidal anti-inflammatory agents is to inhibit the enzyme prostaglandin G/H synthase, also known as cyclooxygenase, which serves as the first committed step in the biosynthesis of prostaglandins. PGHS-2 is a unique isoform of cyclooxygenase, which in contrast to the previously cloned, constitutively expressed enzyme, is dramatically up-regulated by growth factors, tissue injury, and proinflammatory cytokines, and down-regulated by glucocorticoids (O'Banion et al., 1991, J. Biol. Chem., 266:23261–23267; O'Banion et al., 1992, Proc. Nat'l. Acad. Sci. USA, 89:4888–4892: Pritchard et al., 1994, J. Biol. Chem., 269:8504–8509). Recent studies utilizing specific pharmacological inhibitors of PGHS-2 confirm that it plays a major role in peripheral inflammation (Futaki et al., 1993, J. Pharm. Pharmacol., 45:753–755; Masferrer et al., 1994, Proc. Natl. Acad. Sci. USA, 91: 3228–3232; Vane et al., 1994, Proc. Nat'l. Acad. Sci. USA, 91:2046–2050).

The present invention also comprises an isolated DNA sequence (gene) encoding biologically active human PGHS-2; antisense and ribozyme molecules specific for the PGHS-2 transcript; polynucleotide molecules which form a triple helix at the 5' region of the PGHS-2 gene and thereby prevent or reduce transcription of the gene; the isolated, essentially pure human PGHS-2 gene product; antibodies to the gene product; continuous cell lines engineered to stably express PGHS-2; assays for screening compounds, including peptides, polynucleotides, and small organic molecules to identify those that inhibit the expression or activity of the PGHS-2 gene product; and methods of treating diseases characterized by aberrant PGHS-2 activity using such compounds.

5.1. DNA ENCODING MAMMALIAN PGHS-2

The screening of a murine cDNA library enriched in the 4 kb mRNA of O'Banion et al., 1991, J. Biol. Chem., 35:2326–23267 with a radiolabelled portion of the 2.8 kb PGHS cDNA revealed a 4.1 kb sequence (FIG. 1). Comparison of the 4.1 kb sequence with that of the previously cloned mouse 2.8 kb PGHS cDNA revealed a single open reading frame with 64% amino acid identity to the protein encoded by the 2.8 kb PGHS cDNA, O'Banion et al., 1992, Proc. Nat'l. Acad. Sci. USA, 89:4888–4892. This 4.1 kb sequence is designated PGHS-2, and the 2.8 kb sequence is designated PGHS-1. The reduced amino acid sequences are colinear except that PGHS-2 has a shorter amino-terminus and longer carboxy-terminus than PGHS-1.

Three of four potential N-glycosylation sites are conserved between the two molecules and there is particularly high similarity in the regions surrounding a putative axial heme-binding domain (amino acids 273–342) and the region around the presumed aspirin modified-serine$^{516}$ (amino acids 504–550). By far the largest difference in the two cDNAs is the presence of a 2.1 kb 3' untranslated region in the 4.1 kb cDNA. This region is rich in 5'-AUUUA-3' motifs that are associated with the decreased stability of many cytokine and protooncogene mRNAs. The presence of these motifs is consistent with the profound superinducibility of the 4.1 kb mRNA by cycloheximide, which is not observed for the 2.8 kb mRNA.

FIG. 2 schematically compares cDNA and protein sequences for the murine 2.8 and 4.1 kb mRNA-encoded cyclooxygenases. cDNA structures for the 4.1 kb cDNA cloned from murine C127 cells and the murine 2.8 kb cDNA (DeWitt et al., 1990, J. Biol. Chem., 265:5192–5198 are drawn as the thick lines at top and bottom. The numbering of the 4.1 kb cDNA is based on primer extension data. Since the 5' end of the 2.8 kb mouse mRNA has not been determined, no numbers have been assigned to the translation start and stop sites. Alternative polyadenylation sites established from other cDNA clones are indicated with "A" and the 5'-AUUUnA-3' motifs are identified by dots underneath the sequence. These motifs are not found in the 2.8 kb cDNA. Deduced protein sequences are drawn colinearly with gaps (17 aa at the amino-terminal end of the 4.1 kb mRNA product, and 18 aa at the carboxy-terminal end of the 2.8 kb mRNA product) indicated by connected lines. The 26 amino acid (aa) leader sequence for the 2.8 kb PGHS is indicated. Although its extent has not been precisely defined, a shorter, nonhomologous leader appears to exist for griPGHS with a mature N-terminal end at amino acid 18. The positions of potential N-glycosylation sites (NXS/T, "N") and the conserved aspirin modified serines are noted on each molecule. The hatched areas near the center of each molecule denote presumed axial (TIWLREHNRV (SEQ ID NO:7), identical between the two molecules) and distal (KALGH (SEQ ID NO:8)/RGLGH (SEQ ID NO:9)) heme-binding sites as suggested by DeWitt et al., cited above. The bar in the middle of the figure represents the similarities between the two mouse PGHS proteins (omitting the non-conserved N- and C-termini) as the percentage of identical residues for groups of 20 amino acids with increasing shading indicating 40–55% (no shading), 60–75%, 80–95%, and 100% identity. The overall identity is 64% and with conservative changes the similarity index is 79%.

Another specific embodiment of the invention is the human PGHS-2 gene and its product. The human PGHS-2 sequence differs from the human PGHS-2 sequence disclosed by Hla & Neilson, 1992, Proc. Nat'l. Acad. Sci. USA, 89:7384–7388, due to a glutamic acid (E) rather than a glycine (w) at amino acid position 165 of the PGHS-2 gene product (FIG. 7). The sequence for the PGHS-2 gene was confirmed by establishing the identity of the sequences of two other hPGHS-2 clones obtained from separate PCR runs, which demonstrates that the difference observed is not a PCR artifact. Furthermore, as shown in FIG. 1, mouse PGHS-2 also has a glutamic acid at this position. While the human PGHS-2 nucleotide sequence is similar to that of the mouse, there are regions of substantial divergence. These divergent regions in the nucleotide sequence of the human PGHS-2 (FIGS. 6A–6B) include, but are not limited to:

```
    TCCACCCGCAGTACAGAAAGTATCACAGGCT
1375-------------------------------1405

GTGTTCCAGATCCAGAGCTCATTAAAACAGT
1797-------------------------------1827
```

PGHS-1 clones were similarly screened and the sequences of the PGHS-1 gene and enzyme confirmed to be identical to that shown in FIG. 2 (SEQ ID NO:6) in Yokahama and Tanabe, 1984 Biochem. Biophys. Res. Commun., 165:888–894; see also, Hla, 1986, Prostaglandins, 32:829–845.

Fragments of the PGHS-2 DNA are also included within the scope of the invention. In a further embodiment of the invention, the PGHS-2 DNA or a modified sequence thereof may be ligated to a heterologous sequence to encode a fusion protein. For example, for screening peptide libraries it may be useful to encode a chimeric PGHS-2 protein expressing a heterologous epitope that is recognized by a commercially available antibody. A fusion protein may also be engineered to contain a cleavage site located between the PGHS-2 sequence and the heterologous protein sequence, so that the PGHS-2 protein or protein fragment can be cleaved away from the heterologous moiety. In another embodiment, DNA sequences encoding a fusion protein comprising all or a portion of the PGHS-2 protein fused to another protein with a desired activity are within the scope of the invention; e.g., enzymes such as GUS (β-glucuronidase), β-galactosidase, luciferase, etc.

In another embodiment, DNAs that encode mutant forms of PGHS-2 are also included within the scope of the invention. Such mutant PGHS-2 DNA sequences encompass deletions, additions and/or substitutions of nucleotide residues, or of regions coding for domains within the PGHS-2 protein. These mutated PGHS-2 DNAs may encode gene products that are functionally equivalent or which display properties very different from the native forms of PGHS-2.

The invention contemplates, in addition to the DNA sequences disclosed herein, 1) any DNA sequence that encodes the same amino acid sequence as encoded by the DNA sequences shown in FIGS. 1 and 6A–6B; 2) any DNA sequence that hybridizes to the complement of the coding sequences disclosed herein (see FIGS. 1 and 6A–6B) under highly stringent conditions, e.g., washing in 0.1xSSC/0.1% SDS at 68° C. (Ausubel, et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed herein (see FIGS. 1 and 6) under less stringent conditions, such as moderately stringent conditions, e.g., washing in 0.2xSSC/0.1% SDS at 42° C. (Ausubel, et al., 1989, supra), yet which still encodes a functionally equivalent gene product.

The invention also encompasses 1) DNA vectors that contain any of the coding sequences disclosed herein (see FIGS. 1 and 6), and/or their complements (i.e., antisense); 2) DNA expression vectors that contain any of the coding sequences disclosed herein (see FIGS. 1 and 6), and/or their complements (i.e., antisense), operatively associated with a regulatory element that directs the expression of the coding and/or antisense sequences; and 3) genetically engineered host cells that contain any of the coding sequences disclosed herein (see FIGS. 1 and 6), and/or their complements (i.e., antisense), operatively associated with a regulatory element that directs the expression of the coding and/or antisense sequences in the host cell. Regulatory element includes but is not limited to inducible and non-inducible promoters, enhancers, operators and other elements known to those skilled in the art that drive and regulate expression. The invention includes fragments of any of the DNA sequences disclosed herein.

PGHS-2 sequence can be obtained from a variety of sources including cDNA libraries. For example, appropriate cDNA libraries which are good sources of PGHS-2 can be obtained from (Clonetech (Palo Alto, Calif.), Stratagene (La Jolla, Calif.) the ATCC Repository (Rockville, Md.). In addition, cDNA libraries may be prepared from mRNA pools collected from mammalian cells which express PGHS-2 either constitutively or inducibly. By way of example but not by way of limitation, such cells include C127 mouse fibroblasts and W138 human fibroblasts. The collection of mRNA pools and construction of cDNA libraries from these cells are set forth more fully in the examples described infra.

Any of the cDNA libraries described above may be screened by hybridization or PCR using the PGHS-2 sequences described herein as oligonucleotide probes. Screening can be performed using those portions of the PGHS-2 sequence which are not in PGHS-1, see FIGS. 10A–10D. These sequences include the following regions in the nucleotide sequence of PGHS-2:

171–254

299–340

486–512

602–623

1214–1250

1283–1346

1521–1580

1718–1834

In addition to cDNA libraries, partial PGHS-2 sequence can be obtained from any genomic library by library screening or from genomic DNA by PCR. Full cDNA sequences can be obtained by PCR of total RNA isolated from any cell or tissue that expresses PGHS-2 including, but not limited to, brain, heart and lung (where PGHS-2 is expressed without apparent inflammation), as well as in many inflamed tissues such as synovial biopsies from rheumatoid arthritis. Cellular sources include, but are not limited to, primary and established cultures of fibroblasts, macrophages, endothelial cells, synoviocytes, vascular smooth muscle cells and astrocytes treated with growth factors, serum, inflammatory cytokines, calcium ionophores, or oncogenes, particularly if cycloheximide is included.

Alternatively, the cDNA libraries described above can be used to construct expression libraries in a cell line such as COS A2 which contains little or no autologous cyclooxygenase activity. These expression libraries can then be screened using antibodies which are specific to PGHS-2 and do not bind PGHS-1. Expression libraries for antibody screening may also be made in bacteria, such as E. coli, using phage vectors, such as lambda. Antibodies with specificity to PGHS-2 are commercially available through Cayman Chemical (Ann Arbor, Mich.), Oxford Biomedical Research, Inc. (Oxford, Mich.), and Transduction Laboratories (Lexington, Ky.). These expression libraries may also be screened for PGHS-2 enzyme activity as set forth in the examples which are described in more detail infra.

5.2. EXPRESSING THE PGHS-2 GENE PRODUCT

In order to express a biologically active PGHS-2, the coding sequence for the enzyme, a function equivalent, or a modified sequence, as described in Section 5.1., supra, is inserted into an appropriate eukaryotic expression vector, i.e., a vector which contains the necessary elements for transcription and translation of the inserted coding sequence in appropriate eukaryotic host cells which possess the cellular machinery and elements for the proper processing, i.e., signal cleavage, glycosylation, phosphorylation, sialylation, and protein sorting. Mammalian host cell expression systems are preferred for the expression of biologically active enzymes that are properly folded and processed. When administered in humans such expression products may also exhibit tissue targeting.

The invention also encompasses peptide fragments of the PGHS-2 gene product. The PGHS-2 gene product or peptide fragments thereof, can be linked to a heterologous peptide or protein as a fusion protein. In addition, chimeric PGHS-2 expressing a heterologous epitope that is recognized by a commercially available antibody is also included in the invention. A durable fusion protein may also be engineered; i.e., a fusion protein which has a cleavage site located between the PGHS-2 sequence and the heterologous protein sequence, so that the PGHS-2 gene product, or fragment thereof, can be cleaved away from the heterologous moiety. For example, a collagenase cleavage recognition consensus sequence may be engineered between the PGHS-2 gene product, or fragment thereof, the heterologous peptide or protein. The PGHS-2 domain can be released from this fusion protein by treatment with collagenase.

5.2.1. CONSTRUCTION OF EXPRESSION VECTORS AND PREPARATION OF TRANSFECTANTS

Methods which are well-known to those skilled in the art can be used to construct expression vectors containing the PGHS-2 coding sequence and appropriate transcriptional/translational control signals. These methods include in vitro recombination/genetic recombination. See, for example, the techniques described in Sambook et al., 1987, Molecular Cloning A Laboratory Manual, Cold Spring Harbor Laboratory, N.Y., Chapter 12.

Human PGHS-1 or PGHS-2 proteins produced by these methods would be useful for in vitro studies on the mechanism of action of the human forms of PGHS-1 and PGHS-2 and particularly for further studies on the mechanism of action of any inhibitors that are selective for PGHS-2 or PGHS-1 that are identified by drug screening with the stably expressing PGHS-2 or PGHS-1 cell lines, as infra, or for investigating the mechanism of action of existing drugs or of inhibitors that may be identified by other means. The purified human PGHS-2 or PGHS-1 proteins would also be useful for the production of crystals suitable for X-ray crystallography. Such crystals would be extremely beneficial for the rational design of drugs based on molecular structure. Although the crystal structure for ovine PGHS-1 has been obtained, this information is not yet available for either human PGHS-1 or PGHS-2. Expression of these chimeric DNA constructs in a baculovirus or yeast system and subsequent crystallization of the proteins would yield such data.

A variety of eukaryotic host-expression systems may be used to express the PGHS-2 coding sequence. Although prokaryotic systems offer the distinct advantage of ease of manipulation and low cost of scale-up, their major drawback in the expression of PGHS-2 is their lack of proper post-translational modifications of expressed mammalian proteins. Eukaryotic systems, and preferably mammalian expression systems, allow for proper modification to occur. Eukaryotic cells which possess the cellular machinery for proper processing of the primary transcript glycosylation, phosphorylation, and, advantageously secretion of the gene product should be used as host cells for the expression of PGHS-2. Mammalian cell lines are preferred. Such host cell lines may include but are not limited to CHO, VERO, BHK, HeLa, COS, MDWCK, -293, WI38, etc. Alternatively, eukaryotic host cells which possess some but not all of the cellular machinery required for optional processing of the primary transcript and/or post-translational processing and/or secretion of the gene product may be modified to enhance the host cell's processing capabilities. For example, a recombinant nucleotide sequence encoding a peptide product that performs a processing function the host cell had not previously been capable of performing, may be engineered into the host cell line. Such a sequence may either be co-transfected into the host cell along with the gene of interest, or included in the recombinant construct encoding the gene of interest. Alternatively, cell lines containing this sequence may be produced which are then transfected with the gene of interest.

Appropriate eukaryotic expression vectors should be utilized to direct the expression of PGHS-2 in the host cell chosen. For example, at least two basic approaches may be followed for the design of vectors based on SV40. The first is to replace the SV40 early region with the gene of interest while the second is to replace the late region (Hammarskjold, et al., 1986, Gene, 43:41–50. Early and late region replacement vectors can also be complemented in vitro by the appropriate SV40 mutant lacking the early or late region. Such complementation will produce recombinants which are packaged into infectious capsids and which contain the PGHS-2 gene. A permissive cell line can then be infected to produce the recombinant protein. SV40-based vectors can also be used in transient expression studies, where best results are obtained when they are introduced into COS (CV-1, origin of SV40) cells, a derivative of CV-1 (green monkey kidney cells) which contain a single copy of an origin defective SV40 genome integrated into the chromosome. These cells actively synthesize large T antigen (SV40), thus initiating replication from any plasmid containing an SV40 origin of replication.

In addition to SV40, almost every molecularly cloned virus or retrovirus may be used as a cloning or expression vehicle. Viral vectors based on a number of retroviruses (avian and murine), adenoviruses, vaccinia virus (Cochran, et al., 1985, Proc. Natl. Acad. Sci. USA, 82:19–23) and polyoma virus may be used for expression. Other cloned viruses, such as J C (Howley, et al., 1980, J. Virol, 36:878–882), BK and the human papilloma viruses (Heilmsan, et al., 1980, J. Virol, 36:395–407), offer the potential of being used as eukaryotic expression vectors. For example, when using adenovirus expression vectors the PGHS-2 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the human enzyme in infected hosts (e.g., see Logan & Shenk, 1984, Proc. Natl. Acad. Sci. USA, 81:3655–3659). Alternatively, the vaccinia virus 7.5K promoter may be used. (e.g., see, Hackett et al., 1982, Proc. Natl. Acad. Sci. USA, 79:7415–7419; Hackett et al., 1994, J. Virol. 49:857–864, Panicali et al., 1982, Proc. Natl. Acad. Sci. USA, 79:4927–4931). Of particular interest are vectors based on bovine papilloma virus (Sarver, et al., 1981, Mol. Cell. Biol., 1:486–496), or Semliki Forest Virus, which provides large quantities of active protein in induced cells (Olkkohnen et al., 1994, Meth. Cell. Biol., 43 part A:43–53; Lundstrum et al., 1994, Eur. J. Biochem., 224:917–921). These vectors have the ability to replicate as extrachromosomal elements. Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. High level expression may also be achieved using inducible promoters such as the metallothionine IIA promoter, heat shock promoters, etc.

For long-term, high-yield production of recombinant proteins, stable expression is preferred. For example, following the introduction of foreign DNA, engineered cells may be allowed to grow for 1–2 days an enriched media, and then are switched to a selective media. Rather than using expression vectors which contain viral origins of replication, host cells can be transformed with the PGHS-2 DNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell, 11:223–232), hypoxanthine-guanine phosphoribosylatransferase (Szybalska & Szybalski, 1962, Proc. Natl. Acad. Sci. USA, 48:2026), and adenine phosphoribosyltransferase (Lowy, et al., 1980, Cell, 22:817–823) genes can be employed in tk$^-$, hgprt$^-$ or aprt$^-$ cells respectively. Also, antimetabolite resistance can be used as the basis of selection for dhfr, which confers resistance to methotrexate (Wigler, et al., 1980, Natl. Acad. Sci. USA 77:3567–3570; O'Hare, et al., 1981, Proc. Natl. Acad. Sci. USA 78:1527–1531); ygpt, which confers resistance to mycophenolic acid (Mulligan & Berg, 1981, Proc. Natl. Acad. Sci. USA, 78:2072–2076); neo, which confers resistance to the aminoglycoside G-418 (Colberre-Garapin, et al., 1981, J. Mol. Biol., 150:1–14); and hygro, which confers resistance to hygromycim (Santerre, et al., 1994, Gene, 30:147–156) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA, 85:8047–8051), and ODC (ornithine decarboxylase) which confers resistance to the ornithine decarboxylase inhibitor, 2-(difluromethyl)-DL-ornithine, DFMO (McConlogue L., 1987, In: Current Communications in Molecular Biology, Cold Spring Harbor Laboratory ed.).

Alternative eukaryotic expression systems which may be used to express the PGHS-2 enzymes are yeast transformed with recombinant yeast expression vectors containing the PGHS-2 coding sequence; insect cell system infected with recombinant virus expression vectors (e.g., baculovirus) containing the PGHS-2 coding sequence; or plant cell systems infected with recombinant virus expression vectors (e.g., cauliflower mosaic virus, CaMV; tobacco mosaic, TMV) or transformed with recombinant plasmid expression vectors (e.g., Ti plasmid) containing the PGHS-2 coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel Acad. Press, N.Y., Vol. 152, pp. 673–694; and The Molecular Biology of the Yeast Saccharomyces, 1982, Eds. Strathem et al., Cold Spring Harbor Press, Vols. I and II. For complementation assays in yeast, cDNAs for PGHS-2 may be cloned into yeast episomal plasmids (YEp) which replicate autonomously in yeast due to the presence of the yeast 2 $\mu$ circle. The cDNA may be cloned behind either a constitutive yeast promoter such as ADH or LEU2 or an inducible promoter such as GAL (Cloning in Yeast, Chpt. 3, R. Rothstein In: DNA Cloning Vol. 11, A Practical Approach, Ed. DM Glover, 1986, IRL Press, Wash., D.C.). Constructs may contain the 5' and 3' non-translated regions of the cognate PGHS-2 mRNA or those corresponding to a yeast gene. YEp plasmids transform at high efficiency and the plasmids are extremely stable. Alternatively, vectors may be used which promote integration of foreign DNA sequences into the yeast chromosome.

Alternately, active, post-translationally modified human PGHS-1 and PGHS-2 proteins can be obtained using a yeast expression system such as the Pichia pastoris expression system marketed by Invitrogen (Pichia pastoris is owned and licensed by Research Corporation Technologies, Tucson, Ariz.; however, all components are available from Invitrogen, San Diego, Calif.). In this example, cDNAs encoding human PGHS-2 and PGHS-1 are independently cloned into the pHIL-D2 Pichia expression vector. After linearization with a restriction endonuclease, these constructs are transfected into spheroblasts of the his4 Pichia pastoris strain, GS115, and recombinant yeast carrying the cloned PGHS-1 or PGHS-2 DNA sequences are identified by screening for yeast clones that grow in the absence of histidine (now supplied by the recombinant vector), but do not efficiently utilize methanol as the sole carbon source (due to the presence of PGHS-1 or PGHS-2 in the place of AOXI gene sequence coding for methanol utilization). After expansion of such clones in the presence of an alternative carbon source such as glycerol, large quantities of cells would be transferred to liquid media containing methanol where replication ceases. However, cells remain viable for many days during which time human PGHS-1 or PGHS-2 proteins are specifically expressed at high levels under control of the AOXI promoter. The advantages of this system include very high protein yields and lower expense in the production and maintenance of cultures.

In cases where plant expression vectors are used, the expression of the PGHS-2 coding sequence may be driven by any of a number of promoters. For example, viral promoters such as the 35S RNA and 19S RNA promoters of CaMV (Brisson et al., 1984, Nature, 310:511–514), or the coat protein promoter of TMV (Takamatsu et al., 1987, EMBO J., 6:307–311) may be used; alternatively, plant promoters such as the small subunit of RUBISCO (Coruzzi et al., 1994, EMBO J., 3:1671–1680; Broglie et al., 1984, Science, 224:838–843); or heat shock promoters, eg., soybean hsp 17.5-E or hsp 17.3-B (Gurley et al., 1986, Mol. Cell. Biol., 6:559–565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

An alternative expression system which could be used to express PGHS-2 is an insect system. In one such system, Autographa californica nuclear polyhedrosis virus (AcNPV) is used as a vector to express foreign genes. The virus grows in Spodoptera frugiperda cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith et al., 1983, J. Virol., 46:584, Smith, U.S. Pat. No. 4,215,051).

In a specific embodiment of an insect system, the DNA encoding human PGHS-2 or PGHS-1 can be independently cloned into the pBlueBacIII recombinant transfer vector (Invitrogen, San Diego, Calif.) downstream of the polyhedrin promoter and transfected into Sf9 insect cells (derived from Spodoptera frugiperda ovarian cells, available from Invitrogen, San Diego, Calif.) to generate recombinant virus containing human PGHS-1 or PGHS-2. After plaque purification of the recombinant virus high-titer viral stocks are prepared that in turn would be used to infect Sf9 or High Five™ (BTI-TN-5B1-4 cells derived from Trichoplusia ni egg cell homogenates; available from Invitrogen, San Diego, Calif.) insect cells, to produce large quantities of appropriately post-translationally modified PGHS-1 or PGHS-2 proteins. Although it is possible that these cells themselves could be directly useful for drug assays, the PGHS-1 or PGHS-2 proteins prepared by this method can be used for in vitro assays of drug potency and selectivity.

5.2.2. IDENTIFICATION OF TRANSFECTANTS OR TRANSFORMANTS EXPRESSING THE PGHS-2 GENE PRODUCT

The host cells which contain the PGHS-2 coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of PGHS-2 mRNA transcripts in the host cell; and (d) detection of the gene product as measured by immunoassay or by its biological activity.

In the first approach, the presence of the PGHS-2 coding sequence inserted in the expression vector can be detected by DNA—DNA or DNA-RNA hybridization or PCR using probes comprising nucleotide sequences that are homologous to the mouse PGHS-2 coding sequence [SEQ ID NO:1] or human PGHS-2 coding sequence [SEQ ID NO:3] substantially as shown in FIGS. 1 and 6A–6B, or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in baculovirus, etc.). For example, if the PGHS-2 coding sequence is within a marker gene sequence of the vector, recombinants containing the PGHS-2 coding sequence can be identified by the absence of the marker gene function. Alternatively, a marker gene can be placed in tandem with the PGHS-2 sequence under the control of the same or different promoter used to control the expression of the PGHS-2 coding sequence. Expression of the marker in response to induction or selection indicates expression of the PGHS-2 coding sequence. In addition, the marker gene may be identified by DNA—DNA or DNA-RNA hybridization or PCR.

In the third approach, transcriptional activity for the PGHS-2 coding region can be assessed by hybridization or PCR assays. For example, RNA can be isolated and analyzed by Northern blot using a probe homologous to the PGHS-2 coding sequence or particular portions thereof substantially as shown in FIG. 1 (murine, [SEQ ID NO:1]) or FIGS. 6A–6B (human, SEQ ID NO:3]). Alternatively, total nucleic acids of the host cell may be extracted and assayed for hybridization to such probes.

In the fourth approach, the expression of the PGHS-2 protein product can be assessed immunologically, for example by Western blots, immunoassays such as radioimmuno-precipitation, enzyme-linked immunoassays and the like. The ultimate test of the success of the expression system, however, involves the detection of the biologically active PGHS-2 gene product. Where the host cell secretes the gene product, the cell free media obtained from the cultured transfectant host cell may be assayed for PGHS-2 activity. Where the gene product is not secreted, cell lysates may be assayed for such activity. In either case, a number of assays can be used to detect PGHS-2 activity including but not limited to the following: cyclooxygenase activity may be determined in the culture medium by the addition of exogenous arachidonic acid substrate (30 $\mu$M for 15 min. at 37° C.) followed by conversion of the prostaglandin $E_2$ product to a methyl oximate form. This derivative may then be quantitated by radioimmunoassay (kit from Amersham Corp.)

5.2.3. CELL LINES EXPRESSING PGHS-1 OR PGHS-2

The present invention also relates to cell lines containing recombinant DNA sequence, preferably a chromosomally integrated recombinant DNA sequence, which comprises a gene encoding the regulated inflammatory cyclooxygenase griPGHS or "PGHS-2" which cell lines further do not express autologous PGHS-1 or PGHS-2, apart from that encoded by the recombinant DNA sequence. The recombinant DNA also does not encode constitutive PGHS-1 (EC 1.14.99.1).

A specific embodiment of the present invention is an engineered mammalian cell line which contains a chromosomally integrated, genetically-engineered ("recombinant") DNA sequence, which DNA sequence expresses mammalian, preferably human, PGHS-2, but does not express constitutive mammalian PGHS-1, and wherein said cell line also does not express autologous PGHS-1 or PGHS-2. The cell line is preferably of human or primate origin, such as the exemplified monkey kidney COS cell line, but cell lines derived from other species may be employed, including chicken, hamster, murine, ovine and the like; the CHO (Chinese hamster ovary) cell line for example, may be particularly preferred for large scale production.

Any cell or cell line, the genotype of which has been altered by the presence of a recombinant DNA sequence is encompassed by the invention. The recombinant DNA sequence may also be referred to herein as "heterologous DNA," "exogenous DNA," "genetically engineered" or "foreign DNA," indicating that the DNA was introduced into the genotype or genome of the cell or cell line by a process of genetic engineering.

The invention includes, but is not limited to, a cell or cell line wherein the native PGHS-2 DNA sequence has been removed or replaced as a result of interaction with a recombinant DNA sequence. Such cells are called PGHS-2 knockouts, herein, if the resulting cell is left without a native DNA that encodes a functional PGHS-2 gene product.

As used herein, the term "recombinant DNA sequence" refers to a DNA sequence that has been derived or isolated from any source, that may be subsequently chemically altered, and later introduced into mammalian cells. An example of a recombinant DNA sequence "derived" from a source, would be a DNA sequence that is identified as a useful fragment within a given organism, and which is then chemically synthesized in essentially pure form. An example of such DNA sequence "isolated" from a source would be a DNA sequence that is excised or removed from said source by chemical means, e.g., by the use of restriction endonucleases, so that it can be further manipulated, e.g., amplified, for use in the invention, by the methodology of genetic engineering.

Therefore, "recombinant DNA sequence" includes completely synthetic DNA, semi-synthetic DNA, DNA isolated from biological sources, and DNA derived from introduced RNA. Generally, the recombinant DNA sequence is not originally resident in the genotype which is the recipient of the DNA sequence, or it is resident in the genotype but is not expressed.

The isolated recombinant DNA sequence used for transformation herein may be circular or linear, double-stranded or single-stranded. Generally, the DNA sequence is chimeric linear DNA, or is a plasmid or viral expression vector, that can also contain coding regions flanked by regulatory sequences which promote the expression of the recombinant DNA present in the resultant cell line. For example, the recombinant DNA sequence may itself comprise or consist of a promoter that is active in mammalian cells, or may utilize a promoter already present in the genotype that is the transformation target. Such promoters include the CMV promoter depicted in FIG. 4, as well as the SV 40 late promoter and retroviral LTRs (long terminal repeat elements).

The general methods for constructing recombinant DNA which can transform target cells are well known to those skilled in the art, and the same compositions and methods of construction may be utilized to produce the DNA useful herein. For example, J. Sambrook et al., Molecular Cloning; A Laboratory Manual, Cold Spring Harbor Laboratory Press (2d ed., 1989), provides suitable methods of construction.

Aside from recombinant DNA sequence that serve as transcription units for PGHS-1, PGHS-2 or other portions thereof, a portion of the recombinant DNA may be untranscribed, serving a regulatory or a structural function.

The recombinant DNA sequence to be introduced into the cells further will generally contain either a selectable marker gene or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in mammalian cells. Useful selectable markers are well known in the art and include, for example, anti-biotic and herbicide resistance genes.

Sources of DNA sequences useful in the present invention include Poly-A RNA from mammalian cells, from which the about 4 kb mRNA encoding PGHS-2 can be derived and used for the synthesis of the corresponding cDNA by methods known to the art. Such sources include the lambda ZAP II (Stratagene) library of size fractionated poly-A RNA isolated from C127 murine fibroblasts treated with serum and cycloheximide as described by O'Banion et al., 1991, J. Biol. Chem., 266:23261–23267. Xie et al. obtained mRNA encoding chicken PGHS-2 as described in 1991, Proc. Nat'l. Acad. Sci. USA, 88:2692–2696. Sources of human mRNA encoding PGHS-2 include RNA from human monocytes treated with interleukin-1 and cycloheximide, in accord with O'Banion et al., 1992, Proc. Nat'l. Acad. Sci. USA, 89:4888–4892. Sources of human mRNA encoding PGHS-1 are also well known to the art.

Selectable marker genes encoding enzymes which impart resistance to biocidal compounds are listed in Table 1, below.

TABLE 1

Selectable Marker Genes

| Resistance Gene or Enzyme | Confers Resistance to: | Reference |
|---|---|---|
| Neomycin phosphotransferase (neo) | G-418, neomycin, kanamycin | Southern et al., 1982, J. Mol. Appl. Gen., 1:327–341 |
| Hygromycin phosphotransferase (hpt or hyg) | Hygromycin B | Shimizu et al., 1986, Mol. Cell Biol., 6:1074–1087 |
| Dihydrofolate reductase (dhfr) | Methotrexate | Kwok et al., 1986, Proc. Nat'l. Acad. Sci. USA, 4552–4555 |
| Phosphinothricin acetyltransferase (bar) | Phosphinothricin | DeBlock et al., 1987, EMBO J., 6:2513–2518 |
| 2,2-Dichloropropionic acid | 2-2,Dichloropropionic acid | Buchanan-Wollaston et al., 1989, J. Cell. |

TABLE 1-continued

Selectable Marker Genes

| Resistance Gene or Enzyme | Confers Resistance to: | Reference |
|---|---|---|
| dehalogenase | (Dalapon) | Biochem., Supp. 13D, 330 |
| Acetohydroxyacid synthase | Sulfonylurea, imidazolinone and triazolopyrimidine herbicides | Anderson et al. (U.S. Pat. No. 4,761,373); G.W. Haughn et al., 1988 Mol. Gen. Genet., 211:266–271 |
| 5-Enolpyruvyl shikimatephosphate synthase (aroA) | Glyphosate | Comai et al., 1985 Nature, 317:741–744 |
| Haloarylnitrilase | Bromoxynil | Stalker et al., published PCT appln. W087/04181 |
| Acetyl-coenzyme A carboxylase | Sethoxydim, haloxyfop | Parker et al., 1990 Plant Physiol., 92:1220 |
| Dihydropteroate synthase (sul I) | Sulfonamide herbicides | Guerineau et al., 1990, Plant Molec. Biol., 15:127–136 |
| 32 kD photosystem II polypeptide (psbA) | Triazine herbicides | Hirschberg et al., 1983, Science, 222: 1346–1349 |
| Anthranilate synthase | 5-Methyltryptophan | Hibberd et al. (U.S. Pat. No. 4,581,847) |
| Dihydrodipicolinic acid synthase (dap A) | Aminoethyl cysteine | Glassman et al., published PCT application No. W089/11789 |

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., enzymatic activity. Preferred genes includes the chloramphenicol acetyl transferase gene (cat) from Tn9 of *E. coli*, the beta-galactosidase gene of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

Other elements such as introns, enhancers, polyadenylation sequences and the like, may also be a part of the recombinant DNA sequence. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA sequence can be readily introduced into the target cells by transfection with an expression vector, such as a viral expression vector, comprising cDNA encoding PGHS-2 or PGHS-1 by the modified calcium phosphate precipitation procedure of Chen et al., 1987, Mol. Cell. Biol., 7:2745–2752. Transfection can also be accomplished by 15 other methods, including lipofection, using commercially available kits, e.g., provided by Life Technologies.

In a preferred embodiment of the invention, the cell lines of the invention are able to express a stable PGHS-2 gene product or analog, homologue, or deletion thereof after several passages through cell culture. While the instability of the PGHS-2 gene product has been hypothesized to be attributable to the 3' non-coding region of the PGHS-2 mRNA, it has been found that even cell lines which do not include this 3' region are often unable to express a stable PGHS-2 gene product for more than approximately five (5) passages in cell culture. The cell lines of the invention, however, are able to continue to produce a stable PGHS-2 gene product even after at least 5, 10, 15, or 20 passages through cell culture. The cell lines of the invention were selected by the single cell cloning of those cells which were able to continue to stably produce PGHS-2 even after the mere five passages through cell culture which defined the expressing limit of the cells of the prior art.

5.2.4. PURIFICATION OF THE PGHS-2 GENE PRODUCT

Once a cell that produces high levels of biologically active PGHS-2 is identified, the cell may be clonally expanded and used to produce large quantities of the enzyme, which may be purified using techniques well-known in the art including, but not limited to, immunoaffinity purification, chromatographic methods including high performance liquid chromatography and the like. Where the enzyme is secreted by the cultured cells, PGHS-2 may be readily recovered from the culture medium.

Where the PGHS-2 coding sequence, or fragment thereof, has been engineered to encode a cleavable fusion protein, the purification of the PGHS-2 gene product, or fragment thereof, may be readily accomplished using affinity purification techniques. For example, an antibody specific for the heterologous peptide or protein can be used to capture the durable fusion protein; for example, on a solid surface, a column etc. The PGHS-2 moiety can be released by treatment with the appropriate enzyme that cleaves the linkage site. cDNA construction using the polymerase chain reaction accompanied by transfection and purification of the expressed protein permits the isolation of sufficient quantities of PGHS-2 for characterization of the enzyme's physical and kinetic properties. Using site-directed mutagenesis or naturally occurring mutant sequences, this system provides a reasonable approach to determine the effects of the altered primary structure on the function of the protein. Fusion constructs of the PGHS-2 protein domain with the marker peptide preceding the amino terminus of PGHS-2 or following the carboxy terminus of PGHS-2 may also be engineered to evaluate which fusion construct will interfere the least, if at all, with the protein's biologic function and the ability to be purified.

Using this aspect of the invention, any cleavage site or enzyme cleavage substrate may be engineered between the PGHS-2 sequence and a second peptide or protein that has a binding partner which could be used for purification, e.g., any antigen for which an immunoaffinity column can be prepared.

5.3. ANTIBODIES TO THE PGHS-2 GENE PRODUCT

For the production of antibodies, various host animals may be immunized by injection with the PGHS-2 gene product, or a portion thereof including, but not limited to, portions of the PGHS-2 gene product in a recombinant protein. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique which provides for the production of antibody molecules by continuous cell lines in culture. These include but are not limited to the hybridoma technique originally described by Kohler and Milstein, 1975, Nature, 256:495–497, the human B-cell hybridoma technique (Kosbor et al., 1983, Immunology Today, 4:72, Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to one of the binding partners.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

5.4. DIAGNOSTICS

The DNA of the invention encoding the PGHS-2 gene or homologues, analogues, or fragments thereof may be used in accordance with the invention to diagnose disease states which are phenotypic of an aberrant PGHS-2 genotype or of aberrant PGHS-2 expression.

For example, but not by way of limitation, in pulmonary fibrosis from radiation or chronic pulmonary disease, and in the skin disorder scleroderma, only a small percentage of those afflicted respond to glucocorticoids, McCune et al., 1994, Curr. Opin. Rheum., 6(3):262–272; Muir and Benhamou, 1994, [French] Annales de Med. Intern., 145 (Suppl):34–36; Labrune and Huchon, 1991, [French] Revue du Praticien, 41(14):1275–1277. These two disorders have been associated, Steen et al., 1994, Arthritis & Rheum., 37(9):1290–1296; Wells et al., 1994, Am. J. Resp. & Crit. Care Med., 149(6) 1583–1590. Therefore, both these disorders may be characterized by a constitute over expression of PGHS-2 or by excessive longevity of the PGHS-2 message which, in either case, is not diminished by glucocorticoid.

By way of another example, but not by way of limitation, many tumors may be characterized by a lack of, or excess of, PGHS-2 activity which may stem from mutations in the PGHS-2 coding or regulatory sequence.

In both of the examples above, afflicted cells, tissue sections, or biopsy specimens may be screened with the PGHS-2 DNA sequences of the invention and isolated PGHS-2 sequenced to determine which mutations in PGHS-2 are associated with the diseases. The DNAs of the invention may also be used to determine whether an individual carries an aberrant PGHS-2 gene.

In a specific embodiment of the invention, the detection of the aberrant PGHS-2 DNA is conducted by PCR amplification from a small tissue sample. Detection may also be via in situ hybridization or immunocytochemistry of pathology or biopsy specimens.

5.5. GENE THERAPIES BASED ON THE PGHS-2 GENE

A variety of gene therapy approaches may be used in accordance with the invention to modulate expression of the PGHS-2 gene in vivo. For example, antisense DNA molecules may be engineered and used to block translation of PGHS-2 mRNA in vivo. Alternatively, ribozyme molecules may be designed to cleave and destroy the PGHS-2 mRNAs in vivo. In another alternative, oligonucleotides designed to hybridize to the 5' region of the PGHS-2 gene (including the region upstream of the coding sequence) and form triple helix structures may be used to block or reduce transcription of the PGHS-2 gene. In yet another alternative, nucleic acid encoding the full length wild-type PGHS-2 message may be introduced in vivo into cells which otherwise would be unable to produce the wild-type PGHS-2 gene product in sufficient quantities or at all.

In a preferred embodiment, the antisense, ribozyme and triple helix nucleotides are designed to inhibit the translation or transcription of PGHS-2 with minimal effects on the expression of PGHS-1. To accomplish this, the oligonucleotides used should be designed on the basis of relevant sequences unique to PGHS-2; i.e., those sequences found in PGHS-2 and not in PGHS-1.

For example, and not by way of limitation, the oligonucleotides should not fall within those region where the nucleotide sequence of PGHS-2 is most homologous to that of PGHS-1 (see FIGS. 10A–10D), or the PGHS-2 sequence which is shown in FIG. 10 to be identically conserved between PGHS-1 and PGHS-2. These sequences include the following regions in the nucleotide sequence of PGHS-2:

427–457
555–601
624–646
822–901
975–997
1116–1154
1251–1282
1596–1634

Instead, it is preferred that the oligonucleotides fall within the following regions of PGHS-2, which are shown in FIGS. 10A–10D to diverge from the sequence of PGHS-1. These sequences include the following regions in the nucleotide sequence of PGHS-2:

171–254
299–340
486–512
602–623
1214–1250
1283–1346
1521–1580
1718–1834

In the case of antisense molecules, it is preferred that the sequence be chosen from the list above. It is also preferred that the sequence be at least 18 nucleotides in length in order to achieve sufficiently strong annealing to the target mRNA sequence to prevent translation of the sequence. Izant and Weintraub, 1984, Cell, 36:1007–1015; Rosenberg et al., 1985, Nature, 313:703–706.

In the case of the "hammerhead" type of ribozymes, it is also preferred that the target sequences of the ribozymes be chosen from the list above. Ribozymes are RNA molecules which possess highly specific endoribonuclease activity. Hammerhead ribozymes comprise a hybridizing region which is complementary in nucleotide sequence to at least part of the target RNA, and a catalytic region which is adapted to cleave the target RNA. The hybridizing region contains nine (9) or more nucleotides. Therefore, the hammerhead ribozymes of the present invention have a hybridizing region which is complementary to the sequences listed above and is at least nine nucleotides in length. The construction and production of such ribozymes is well known in the art and is described more fully in Haseloff and Gerlach, 1988, Nature, 334:585–591.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech endoribonucleases have an eight base pair active site which hybridizes to a target RNA sequence whereafter cleavage of the target RNA takes place. The invention encompasses those Cech-type ribozymes which target eight base-pair active site sequences that are present in PGHS-2 but not PGHS-1.

In the case of oligonucleotides that hybridize to and form triple helix structures at the 5' terminus of the PGHS-2 gene and can be used to block transcription, it is preferred that they be complementary to those sequences in the 5' terminus of PGHS-2 which are not present in PGHS-1 (see FIGS. 11A–11C). Because of the lack of homology between these regions of PGHS-2 and PGHS-1, any sequence sufficiently long to hybridize to the PGHS-2 promoter will not hybridize to the promoter of PGHS-1. However, it is preferred that the sequences not include those regions of the PGHS-2 promoter which are even slightly homologous to that of PGHS-1. These slightly homologous sequences include the following regions in the nucleotide sequence of the PGHS-2 promoter:

382–438
669–696
797–826
856–885
980–1008
1142–1170
1204–1252
1863–1898
2013–2101
2126–2175
2356–2396

The foregoing compounds can be administered by a variety of methods which are known in the art including, but not limited to the use of liposomes as a delivery vehicle. Naked DNA or RNA molecules may also be used where they are in a form which is resistant to degradation such as by modification of the ends, by the formation of circular molecules, or by the use of alternate bonds including phosphothionate and thiophosphoryl modified bonds. In addition, the delivery of nucleic acid may be by facilitated transport where the nucleic acid molecules are conjugated to polylysine or transferrin. Nucleic acid may also be transported into cells by any of the various viral carriers, including but not limited to, retrovirus, vaccinia, AAV, and adenovirus.

Alternatively, a recombinant nucleic acid molecule which encodes, or is, such antisense, ribozyme, triple helix, or PGHS-2 molecule can be constructed. This nucleic acid molecule may be either RNA or DNA. If the nucleic acid encodes an RNA, it is preferred that the sequence be operatively attached to a regulatory element so that sufficient copies of the desired RNA product are produced. The regulatory element may permit either constitutive or regulated transcription of the sequence. In vivo, that is, within the cells or cells of an organism, a transfer vector such as a bacterial plasmid or viral RNA or DNA, encoding one or more of the RNAs, may be transfected into cells e.g. (Llewellyn et al., 1987, J. Mol. Biol., 195:115–123; Hanahan et al. 1983, J. Mol. Biol., 166:557–580). Once inside the cell, the transfer vector may replicate, and be transcribed by cellular polymerases to produce the RNA or it may be integrated into the genome of the host cell. Alternatively, a transfer vector containing sequences encoding one or more of the RNAs may be transfected into cells or introduced into cells by way of micromanipulation techniques such as microinjection, such that the transfer vector or a part thereof becomes integrated into the genome of the host cell.

5.6. DRUG SCREENING ASSAYS

The present invention provides a simple in vitro system for the screening of drug actions on both the constitutive and the inflammatory cyclooxygenase, which will be useful for the development of drugs that selectively inhibit inflammation without producing the side effects due to inhibition of constitutive prostaglandin production. Assays can be performed on living mammalian cells, which more closely approximate the effects of a particular serum level of drug in the body, or on microsomal extracts prepared from the cultured cell lines. Studies using microsomal extracts offer the possibility of a more rigorous determination of direct drug/enzyme interactions.

The PGHS-2-synthesizing cell lines are useful for evaluating the activity of potential bioactive agents on the inflammatory cyclooxygenase, since the elevated levels of prostaglandins that are a primary hallmark of inflammation and account for much of the adverse effects of inflammation, result from increases in the level of PGHS-2, rather than in changes in constitutively expressed cyclooxygenase, PGHS-1.

The present invention also provides a second mammalian cell line which contains a chromosomally integrated, recombinant DNA sequence, wherein said DNA sequence expresses mammalian, preferably human, PGHS-1, and wherein said DNA sequence does not express PGHS-2, and wherein said cell line also preferably does not express autologous PGHS-1 or PGHS-2 activity. This second cell line is also preferably a primate, murine or human cell line.

Thus, the present invention also provides a method to evaluate the relative inhibitory activity of a compound to selectively inhibit PGHS-2 versus PGHS-1, and thus to specifically inhibit the elevated prostaglandin synthesis that occurs in inflamed mammalian tissues, preferably human tissues, or in other physiological or pathological conditions in a mammalian host, preferably a human host, in which the PGHS-2 is elevated and the constitutive PGHS-1 is not. This assay comprises contacting the present PGHS-2-expressing transgenic cell line or a microsomal extract thereof with a preselected amount of the compound in a suitable culture medium or buffer, adding arachidonic acid to the mixture, and measuring the level of synthesis of a PGHS-mediated arachidonic acid metabolite, i.e., thromboxane synthesis, prostaglandin synthesis, e.g., the synthesis of $PGE_2$, or the synthesis of any other metabolite unique to the cyclooxygenase pathway, by said cell line, or said microsomal extract, as compared to a control cell line or portion of microsomal extract in the absence of said compound. The compound can be evaluated for its ability to selectively inhibit PGHS-1 or PGHS-2 by performing a second assay employing the above-described steps, but substituting the PGHS-1-expressing transgenic cell line for the PGHS-2-expressing cell line of the invention.

More specifically, the present-invention provides a method of determining the ability of a compound to inhibit prostaglandin,synthesis catalyzed by PGHS-2 or PGHS-1 in mammalian cells comprising:

(a) adding a first preselected amount of said compound to a first transgenic mammalian cell line in culture medium, which cell line contains a chromosomally integrated, recombinant DNA sequence, wherein said DNA sequence expresses mammalian PGHS-2, and wherein said DNA sequence does not express PGHS-1, and wherein said cell line does not express autologous PGHS-1 or PGHS-2 activity;

(b) adding arachidonic acid to said culture medium;

(c) measuring the level of a PGHS-mediated arachidonic acid metabolite synthesized by said first cell line;

(d) comparing said level with the level of said metabolite synthesized by said first cell line in the absence of said compound;

(e) adding a second preselected amount of said compound to a second transgenic mammalian cell line in culture medium, which cell line contains chromosomally integrated, recombinant DNA sequence, wherein said DNA sequence expresses mammalian PGHS-1, and wherein said DNA sequence does not express PGHS-2, and wherein said cell line does not express autologous PGHS-1 or PGHS-2 activity;

(f) adding arachidonic acid to said culture medium of step (e);

(g) measuring the level of a PGHS-mediated arachidonic acid metabolite synthesized by said second cell line; and (h) comparing said level with the level of said metabolite synthesized by said second cell line in the absence of said compound.

The invention also relates to methods for the identification of genes, termed "pathway genes", which are associated with the PGHS-2 gene product or with the biochemical pathways which extend therefrom. "Pathway gene", as used herein, refers to a gene whose gene product exhibits the ability to interact with the PGHS-2 gene product.

Any method suitable for detecting protein-protein interactions may be employed for identifying pathway gene products by identifying interactions between gene products and the PGHS-2 gene product. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g., Creighton, 1983, Proteins: Structures and Molecular Principles, W. H. Freeman & Co., N.Y., pp.34–49). The amino acid sequence obtained may be used as a guide for the generation of oligonucleotide mixtures that can be used to screen for pathway gene sequences. Screening made be accomplished, for example by standard hybridization or PCR techniques. Techniques for the generation of oligonucleotide mixtures and screening are well-known. (See, e.g., Ausubel et al., eds., 1987–1993, Current Protocols in Molecular Biology, John Wiley & Sons, Inc. New York, and PCR Protocols: A Guide to Methods and Applications, 1990, Innis, M. et al., eds. Academic Press, Inc., New York).

Additionally, methods may be employed which result in the simultaneous identification of pathway genes which encode the protein interacting with the PGHS-2 gene product. These methods include, for example, probing expression libraries with labeled protein known or suggested to be involved in cardiovascular disease, using this protein in a manner similar to the well known technique of antibody probing of λgt11 libraries.

One such method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the activator's binding sites. Either hybrid protein alone cannot activate transcription of the reporter gene: the DNA-binding domain hybrid because it does not provide activation function and the activation domain hybrid because it cannot localize to the activator's binding sites. Interaction of the two proteins reconstitutes the functional activator protein and results in expression of the reporter gene, which is detected by an assay for the reporter gene product.

The two-hybrid system or related methodology may be used to screen activation domain libraries for proteins that interact with the PGHS-2 gene product, herein also called the known "bait" gene protein. Total genomic or cDNA sequences may be fused to the DNA encoding an activation domain. Such a library and a plasmid encoding a hybrid of the bait gene protein fused to the DNA-binding domain may be cotransformed into a yeast reporter strain, and the resulting transformants may be screened for those that express the reporter gene. These colonies may be purified and the library plasmids responsible for reporter gene expression may be isolated. DNA sequencing may then be used to identify the proteins encoded by the library plasmids.

For example, and not by way of limitation, the bait gene may be cloned into a vector such that it is translationally fused to the DNA encoding the DNA-binding domain of the GAL4 protein.

A cDNA library of the cell line from which proteins that interact with bait gene are to be detected can be made using methods routinely practiced in the art. According to the particular system described herein, for example, the cDNA fragments may be inserted into a vector such that they are translationally fused to the activation domain of GAL4. This library may be co-transformed along with the bait gene-GAL4 fusion plasmid into a yeast strain which contains a lacZ gene driven by a promoter which contains the GAL4 activation sequence. A cDNA encoded protein, fused to the GAL4 activation domain, that interacts with bait gene will reconstitute an active GAL4 protein and thereby drive expression of the lacZ gene. Colonies which express lacZ may be detected by their blue color in the presence of X-gal. The cDNA may then be purified from these strains, and used to produce and isolate the bait gene-interacting protein using techniques routinely practiced in the art.

Once a pathway gene has been identified and isolated, it may be further characterized as, for example, discussed herein.

The proteins identified as products of pathway genes may be used to modulate PGHS-2 gene expression, as defined herein, or may themselves be targets for modulation to in turn modulate symptoms associated with PGHS-2 expression.

5.7. COMPOUNDS IDENTIFIED IN THE SCREENS

The compounds identified in the screen will demonstrate the ability to selectively modulate the expression of PGHS-2. These compounds include but are not limited to nucleic acid encoding PGHS-2 and homologues, analogues, and deletions thereof, as well as antisense, ribozyme, triple helix, antibody, and polypeptide molecules and small inorganic molecules.

5.8. PHARMACEUTICAL FORMULATIONS AND ROUTES OF ADMINISTRATION

Any of the identified compounds can be administered to an animal host, including a human patient, by itself, or in pharmaceutical compositions where it is mixed with suitable carriers or excipient(s) at doses therapeutically effective to treat or ameliorate a variety of disorders, including those characterized by insufficient, aberrant, or excessive PGHS-2 activity. A therapeutically effective dose further refers to that amount of the compound sufficient to result in amelioration of symptoms associated with such disorders. Techniques for formulation and administration of the compounds of the instant application may be found in "Remington's Pharmaceutical Sciences," Mack Publishing Co., Easton, Pa., latest edition.

A number of disorders in addition to inflammation have been characterized by insufficient, aberrant, or excessive PGHS-2 activity. In addition, several physiological states which may, from time to time be considered undesired, are also associated with PGHS-2 activity. By way of example, but not by way of limitation, such disorders and physiological states which may be treated with the compounds of the invention include but are not limited to neurologic disorders such as Alzheimer's disease, stroke, and acute head injury; colorectal carcinoma; ovulation; preterm labor; endometriosis; implantation; and pulmonary fibrosis.

Pathological features of Alzheimer's Disease (AD) include neuritic amyloid plaques, neurofibrillary tangles, neuronal cell loss, loss of synapses, and marked gliosis. Because they are unique features of the disease, many investigators have focused on the etiology and effects of amyloid plaques and neurofibrillary tangles. However, the significant gains made in understanding these neuropathologic markers have provided few clues regarding treatment of AD. In contrast, recent findings suggest that the "inflammatory processes" associated with gliosis represent a potential target for therapeutic intervention in the disease. In particular, Joe Rogers and colleagues have presented both retrospective and prospective evidence that non-steroidal anti-inflammatory agents can significantly slow the progress of AD (McGeer and Rogers, 1992, Neurology, 42:447–449; Rogers et al., 1993, Neurology, 43:1609–1611). Indeed, these results have prompted the initiation of anti-inflammatory therapy trials for AD.

Evidence for an "inflammatory component" to gliosis in AD includes increased expression of proinflammatory cytokines such as IL-1β and TNFα (Griffin et al., 1989, Proc. Nat'l. Acad. Sci. USA, 88:7611–7615; Dickson et al., 1993, Glia, 7:75–83; Lapchak and Araujo, 1993, Soc. Neurosci. Abstr., 19:191) and the presence of activated complement components (McGeer et al., 1989, Neurosci. Let., 107: 341–346; Johnson et al., 1992, Neurobiol. Aging, 13:641–648; Walker and McGeer, 1992 Mol. Brain Res., 14:109–116). It should be noted that gliosis and the presence of proinflammatory cytokines with the potential to activate PGHS-2 are not limited to AD. Rather, they are a feature of many insults to and disease of the central nervous system including (but not limited to) acute head injury, stroke, spinal cord injury, multiple sclerosis, HIV infection of the brain and other viral encephalopathies, and most neurodegenerative disorders (e.g. Huntington's disease, Parkinson's disease, and amyotrophic lateral sclerosis).

PGHS-2 is expressed in cultured murine and rat astrocytes, and is strongly up-regulated by treatment with proinflammatory cytokines including IL-1β and TNFα (O'Banion et al., 1994, Soc. Neurosci. Abstr.). The induction of PGHS-2 is rapid with mRNA levels peaking at 2 h. Concomitant increases in prostaglandin production are also observed. The fact that induced cyclooxgenase activity is blocked by NS-398, a specific inhibitor of PGHS-2, confirms that induction of PGHS-2 is responsible for increased prostaglandin production in cytokine-treated astrocytes. As in other cell types, glucocorticoid hormones suppress the induction of PGHS-2 by IL-1β.

Other investigators have confirmed that PGHS-2 is expressed in the brain (Yamagata et al., 1993, Neuron, 11:371–386). In these studies, the brains of rats subjected to electroconvulsive shock showed dramatic increases in the levels of PGHS-2 expression in neurons of the cerebral cortex and hippocampus. The authors further demonstrated that synaptic activation led to induction of PGHS-2 mRNA, suggesting that expression of this molecule plays a significant role (as yet undefined) in neuronal communication and/or function. In preliminary in situ hybridization studies it has been confirmed that PGHS-2 is expressed in human brain neurons (Chang et al., 1995, Soc. Neurosci. Ann. Mtg. San Diego, Submitted).

Similar to their proven therapeutic benefits in peripheral inflammation, it is proposed that the efficacy of nonsteroidal anti-inflammatory therapy in the treatment of AD is due to the inhibition of PGHS-2 activity in "inflamed" brain tissue. This therapeutic approach has the potential to benefit a multitude of neurological diseases and injuries with a prominent degree of glial activation. Development of selective inhibitors of human PGHS-2 which specifically target the central nervous system (i.e. that are designed to easily cross the blood-brain barrier and even accumulate in the brain) may prove much more efficacious than current NSAIDS for the treatment of AD and other neurologic disorders.

Colorectal carcinoma is a leading cause of death in westernized countries. Prostaglandins have been correlated with carcinogenesis in general and more specifically with colorectal cancer, Marnett, 1992, Cancer Research, 52:5575–5589. In several clinical trials, aspirin use was associated with decreased colon tumor growth and death, Thun et al., 1991, N. Engl. J. Med., 325:1593–6; Kune, et al., 1988, Cancer Res., 48:439–404. Sulindac, another cyclooxygenase inhibitor, has been demonstrated to cause colon polyp regression in patients with familial polyposis, Waddell and Loughry, 1983, J. Surg. Oncol., 24:83–87. These NSAIDS are able to inhibit both PGHS-1 and -2. Discovery of the gene for PGHS-2 makes clarification of the relative contribution or role in colon cancer possible. PGHS-2 is an immediate early gene suggesting its likely participation in regulating growth. The decreased tumor growth by aspirin is likely through action on PGHS-2. If PGHS-2 is directly implicated then specific inhibition of this enzyme may result in tumor suppression. Discovery of the PGHS-2 gene allows for further clarification of this contribution. Additionally, if inhibition is therapeutic then specific drugs that inhibit PGHS-2 can be obtained that would be ingested and directly act at the mucosal and have limited systemic absorption. In the case of familial polyposis, gene therapy may play an important therapeutic role.

Ovulation has in a broad sense can be viewed as an inflammatory process initiated by the LH surge during the menstrual cycle, Espey, 1980, Biol. Reprod, 22:73–106. NSAIDs have been shown to inhibit ovulation in a number of model systems, Espey, 1982, Prostaglandin, 23:329–335. By inhibiting prostaglandin formulation and interrupting the inflammatory response ovulation is halted. It has been demonstrated that PGHS-2 is specifically stimulated by LH in granulosa cells at the time of ovulation and likely the target of NSAIDs that results in inhibition of ovulation, Sirois and Richards, 1992, J. Biol. Chem., 267:6382–6388. Knowing the gene sequence and protein product not only provides the ability to further study this process but provides a specific target for contraception. PGHS-2 specific drugs would allow inhibition without effecting the prostaglandin production by PGHS-1 which is protective to GI mucosa as well as involved with kidney function and many other homeostatic mechanisms.

Preterm labor is a significant clinical problem. Current available drugs (tocolytics) are able to postpone labor but often are not able to stop labor definitively. Prostaglandins play an important role in induction of labor although their exact contribution and mechanism are yet to be clearly defined, Kelly, 1994, Endocrine Reviews, 15(5):684–706. With the discovery of PGHS-2 a better understanding of prostaglandin regulation in the fetus and uterus can be understood. Current medications used for preterm labor (tocolytics) work by blocking Ca flux thereby interfering with myometrium contraction. Common tocolytics include magnesium sulfate, β-adrenergic receptor agonists, calcium channel blockers and oxytocin antagonists. Indomethacin has also been used effectively but raises concern with premature closure of the ductus arteriosus of the fetus. Closer examination of PGHS-1 and PGHS-2 in these roles may provide opportunities for specific intervention.

Recognition of preterm labor prior to cervical changes is difficult but also the point at which tocolytic agents are most effective. It is known that prostaglandins are intimately involved in myometrium contraction of normal labor, Williams Obstetrics, Cunningham, MacDonald, Gant, Leveno, and Gilstrap (eds) Williams Obstetrics 19th Ed. Appleton and Lange, Norwalk Conn., 1993. It may be possible to evaluate increased PGHS-2 expression and true labor prior to cervical changes. If safe sampling of the site of expression can be done then PCR methods may be able to provide a timely answer to whether the painful uterine contractions are Braxton-Hicks or true labor.

Dysmenorrhea and endometriosis are common, painful problematic conditions for women. It is well known that NSAIDs are extremely effective at treating dysmenorrhea and endometriosis pain by inhibiting prostaglandin production. It is highly likely that the hormones responsible for the cycle of dysmenorrhea and endometriosis also regulates PGHS-2 expression. Inhibition at the protein or genetic level could enhance specific treatment for dysmenorrhea and endometriosis.

Prostaglandin formation is also part of implantation. Manipulation of PGHS-2 expression may provide a means for induction of abortion.

PGHS-2 may play an important role in the lung pathology of cystic fibrosis. It has been demonstrated that high-dose ibuprofen slows the progression of lung disease in this patient population, Konstan, et al., 1995, N. Engl. J. Med., 332 (13):848–854. Lung disease results more from the inflammatory response than by the colonization of bacteria. Utilization of inhalers can directly deliver medication to the site of inflammation. This may provide a logical disease process to attempt anti-sense, ribozyme or triple helix gene therapy aimed at inhibiting PGHS-2 expression.

Besides attempts to inhibit cell growth by inhibiting PGHS-2 there may be certain circumstances whereby growth stimulation is desired as in tissue repair. Determination of the tissue specific regulation of PGHS-2 (studies which require gene sequence information) may lead to the ability to specifically up regulate PGHS-2 in particular cell types (i.e. fibroblasts, neurons). Additionally genetic constructs which will only be activated in particular cell types because of promoter construction could be developed.

Other options may include direct delivery of enzyme which has been produced and purified by genetic means using the cloned gene. Recombinant protein would also greatly facilitate investigation into the distinctions between the enzymes (PGHS-1 and PGHS-2) and the byproducts they produce.

Other isoforms may exist and may be cloned utilizing PGHS-2 sequence.

The compounds of the invention may be designed or administered for tissue specificity. If the compound comprises a nucleic acid molecule, including those comprising an expression vector, it may be linked to a regulatory sequence which is specific for the target tissue, such as the brain, skin, joints, bladder, kidney, liver, ovary, etc. by methods which are known in the art including those set forth in Hart, 1994, Ann. Oncol., 5 Suppl 4: 59–65; Dahler et al., 1994, Gene, 145: 305–310; DiMaio et al., 1994, Surgery, 116:205–213; Weichselbaum et al., Cancer Res., 54:4266–4269; Harris et al., 1994, Cancer, 74 (Suppl. 3):1021–1025; Rettinger et al., Proc. Nat'l. Acad. Sci. USA, 91:1460–1464; and Xu et al, Exp. Hematol., 22:223–230; Brigham et al., 1994, Prog. Clin. Biol. Res., 388:361–365. The compounds of the invention may be targeted to specific sites of inflammation by direct injection to those sites, such as joints, in the case of arthritis. Compounds designed for use in the central nervous system should be able to cross the blood brain barrier or be suitable for administration by localized injection. Similarly, compounds specific for the bladder can be directly injected therein. Compounds may also be designed for confinement in the gastrointestinal tract for use against disorders such as colorectal carcinoma. In addition, the compounds of the invention which remain within the vascular system may be useful in the treatment of vascular inflammation which might arise as a result of arteriosclerosis, balloon angioplasty, catheterization, myocardial infarction, vascular occlusion, and vascular surgery and which have already been associated with PGHS-2 by Pritchard et al., 1994, J. Biol. Chem., 269, 8504–8509. Such compounds which remain within the bloodstream may be prepared by methods well known in the art including those described more fully in McIntire, 1994, Annals Biomed. Engineering, 22:2–13.

5.8.1. EFFECTIVE DOSAGE

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). Dosage amount and interval may be adjusted individually to provide plasma levels of the active moiety which are sufficient to maintain the desired effects.

In cases of local administration or selective uptake, the effective local concentration of the drug may not be related to plasma concentration.

The amount of composition administered will, of course, be dependent on the subject being treated, on the subject's eight, the severity of the affliction, the manner of administration and the judgment of the prescribing physician.

5.8.2. COMPOSITION AND FORMULATION

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

5.8.3. ROUTES OF ADMINISTRATION

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

5.8.4. PACKAGING

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a disease such as one characterized by insufficient, aberrant, or excessive PGHS-2 activity.

6. EXAMPLE: ISOLATION, CLONING, AND SEQUENCING OF MURINE PGHS-2

The subsections below describe the identification and characterization of the murine PGHS-2 gene and gene product. The data demonstrate that PGHS-2 encodes a functional prostaglandin H synthase which is distinct from the product of the PGHS-1 gene. In addition, it is shown that Dexamethasone specifically down-regulates PGHS-2 expression while having no effect on PGHS-1 expression.

6.1. MATERIALS AND METHODS
6.1.1. CELLS AND CELL CULTURES

C127 mouse fibroblasts were obtained from Peter Howley (NIH) and propagated in high glucose Dulbecco's modified Eagle's medium supplemented with 10% fetal bovine serum (HyClone Laboratories) without antibiotics. See, Lowy et al., 1978, J. Virol., 26:291–298. Cultures were monitored for mycoplasma contamination by Hoechst 33258 staining in accord with the procedure of Chen, 1977, Exp. Cell Res., 104:255–262.

Exponentially growing, subconfluent (60–80%) cell monolayers (35-mm plates) were labeled in Dulbecco's modified Eagle's medium without methionine (Life Technologies) plus 200 $\mu$Ci/ml Tran$^{35}$S-label (>1,000 Ci/mmol; ICN) for 15 or 30 min. In some cases, fresh fetal calf serum (10%) was present during the labeling period. Monolayers were rinsed twice with ice-cold Dulbecco's modified Eagle's medium (DMEM) with methionine prior to lysis in 200 $\mu$l of A8 buffer (9.5M urea, 2% (w/v) Nonidet P-40, 2% (w/v) ampholines (LKB, 1.6% pH range 5–8, 04.% pH range 3.5–10), 5% (w/v) 2-mercaptoethanol). Incorporation of label into proteins was determined by trichloroacetic acid precipitation. Dexamethasone (Sigma) was freshly prepared in phosphate-buffered saline (PBS) (stock concentrations based on molar extinction coefficient of 1.5×10$^4$ liters/mol/cm at 250 nn) and added to 1 $\mu$M. The calcium ionophore A23187 (Calbiochem) was used at a concentration of 5 $\mu$M from a 2.5 mM stock in ethanol. Cycloheximide (Sigma) was used at a concentration of 25 $\mu$M from a 100 X stock in water. This level inhibited protein synthesis by >97% within 15 min. Control cultures received appropriate amounts of solvents.

6.1.2. DETERMINATION OF CYCLOOXYGENASE ACTIVITY

Cyclooxygenase activity was determined in the cultures by addition of media containing exogenous arachidonic acid substrate (30 $\mu$M for 15 min. at 37° C.) followed by conversion of the prostaglandin $E_2$ product to a methyl oximate form. This derivative was then quantitated by radioimmunoassay (kit from Amersham Corp.).

6.1.3. RNA PREPARATION

Total RNA was isolated from 15-cm plates using guanidinium isothiocyanate lysis followed by centrifugation through a cesium chloride cushion, Chirgwin et al., 1979, Biochemistry, 18:5294–5299. Poly(A) RNA was prepared by two passes through oligo(dT)-cellulose columns, as disclosed by Aviv et al., 1972, Proc. Nat'l. Acad. Sci. USA, 69:1408–1412. RNAs were quantitated by absorbance measurements at 260 nm.

6.1.4. cDNA SYNTHESIS

Fifty $\mu$g of poly-A enriched RNA from C127 cells treated for 2.5 hr. with serum and cycloheximide (25 $\mu$m) were fractionated on a 10–30% sucrose gradient in the presence of 10 mM $CH_3HgOH$ as disclosed by J. Sambrook et al., cited above. Every other fraction was assayed for the presence of the 4 kb mRNA (O'Banion, et al., 1991, J. Biol. Chem., 266:23261–23267 by Northern blot analysis using the 1.6 kb 5' end of the ovine PGHS cDNA (obtained from Oxford Biomedical Research, Inc.) labeled by random priming. RNA samples and molecular weight markers (3 gg; Bethesda Research Laboratories RNA ladder) were subjected to formaldehyde-agarose gel electrophoresis (J. Sambrook et al., Molecular Cloning, cited above at pages 7.30–7.32) and then blotted to nylon membranes (Duralon, Stratagene) by overnight capillary transfer in 10 X SSC (1×SSC is 0.15M NaCl, 0.015M sodium citrate).

cDNAs were prepared from fractions enriched in the 4-kb mRNA by oligo(dT) priming (Gubler et al., 1988, Gene (Amst.), 25:263 kit from Stratagene) and ligated into λ-ZAP II (Short et al., 1988, Nucleic Acids Res., 16:7583–7600, Stratagene). Two hundred fifty thousand plaques were screened with the ovine PGHS probe under conditions of reduced stringency (30% formamide, hybridization temperature reduced to 42° C., filters washed in 2 X SSC+0.1% at 55° C.). Double-strand dideoxy termination sequencing of Exo III nested deletion subclones was carried out in both directions using T7 DNA polymerase. See Heinikoff, 1984, Gene, 28:351; Del Sal et al., 1989, Bio-Techniques, 7:514–520.

6.1.5. IN VITRO TRANSCRIPTION, IN VITRO TRANSLATION, IMMUNOPRECIPITATION, AND PRIMER EXTENSION

One $\mu$g of cDNA in a Bluescript vector (Stratagene) was linearized at the 3' end with Xho I and transcribed with T3 RNA polymerase in a reaction containing the capping reagent m$^7$G(5')ppp(5')G (kit from Stratagene). After purification, one-fifth of the transcribed RNA and 2.5 $\mu$g of poly-A RNA purified as described above, from cycloheximide and serum-treated C127 cells were translated in separate in vitro reactions containing $^{35}$S-methionine as described by the manufacturer (Promega) except that the RNAs were preincubated with 3.5 mM CH$_3$HgOH for 10 min at room temperature. Reactions were diluted in a modified RIPA buffer and precipitated with polyclonal anti-PGHS serum (Oxford Biomedical Research, Inc.) or first precleared by incubating for 30 min with 50 µ/lml protein A-Sepharose (Pharmacia LKB Biotechnology Inc.; 50% (v/v)). 0.01 volume of antiserum or normal rabbit serum was added to the lysate and allowed to incubate for 2 hr at 4° C. prior to precipitation with protein A-Sepharose. The pelleted beads were washed four times with immunoprecipitation buffer and then resuspended in Laemmli lysis buffer for 30 min at room temperature. The immunoprecipitated products were resolved by standard 10% SDS-PAGE and visualized by fluorography.

For primer extension analysis two µg of poly-A RNA from C127 cells treated for 2 hr with serum and cycloheximide was reverse-transcribed with M-MuLV reverse transcriptase (Life Technologies) as described by Baker et al., 1987, EMBO J., 6:1027–1035, using a $^{32}$P-end-labeled oligonucleotide complementary to nucleotide (nt) 55–75 of the sequenced 4.1 kb cDNA. Reaction products were electrophoresed on a standard sequencing gel in parallel with an $^{35}$S-labeled dideoxy sequencing reaction of the cDNA in its Bluescript vector using the same primer.

6.1.6. cDNA EXPRESSION AND PGE$_2$ DETERMINATION

In order to determine whether the 4.1 kb mRNA encodes a protein with cyclooxygenase activity, the cDNA was inserted into an SV40 late promoter expression vector (SVL, (Breatnach et al., 1983, Nucleic Acid Res., 11:7119. As reported by DeWitt et al., 1990, J. Biol. Chem., 265:5192–5198, COS cells have little or no autologous cyclooxygenase activity. Therefore, these cells were transfected with 2.5 or 5 µg of either the vector alone or the vector containing the 4.1 kb cDNA.

6.1.7. NORTHERN BLOT ANALYSIS

Poly-A enriched RNAs (2.5 µg) from C127 cells were fractionated by formaldehyde-agarose gel electrophoresis and transferred to a membrane (Duralon, Stratagene). Hybridization was carried out as previously described by O'Banion et al., 1991, J. Virol., 65:3481–3488, using the 5' 1.2 kb EcoR1 fragment of the 4.1 kb cDNA labeled with $^{32}$P by random priming as disclosed by Feinberg et al., 1983, Anal. Biochem., 132:6–13. The membrane was later rehybridized with a similarly labeled portion (1.6 kb 5' end) of the 2.8 kb ovine PGHS cDNA (Oxford Biomedical Research, Inc.), and an end-labeled 40-mer complimentary to β-tubulin (Oncor). RNA molecular weight markers (Life Technologies) were visualized by ethidium bromide staining. A similar analysis was performed on total RNA (5 82 g/lane) isolated from human monocytes by the guanidinium-acid-phenol extraction method of Chomczynski et al., 1987, Anal. Biochem., 162:156–159.

6.1.8. EXPRESSIONS OF PGHS-2 IN HUMAN MONOCYTES

Adherent human monocytes isolated from healthy donors as described by Roberts et al., 1978, J. Immunol, 121:1052–1058, were suspended in M199 medium without serum at 1×10$^6$ cells/ml. One ml aliquots in 5 ml polypropylene tubes were incubated with loosened caps in 5% CO$_2$ at 37° C. with occasional shaking. To derive the autoradiograph shown in FIG. 3A, monocytes were incubated for 4 hr in the presence or absence of dexamethasone (1 µM; Sigma) prior to total RNA isolation by the procedure of P. Chomczynski et al., cited above. Five µg RNA was subjected to Northern blot analysis as described by O'Banion et al., 1991, J. Biol. Chem., 34:23261–23267 with the indicated probes labeled by random priming (kit from Boehringer-Mannheim) to a specific activity >1×10$^9$ cpm/µg. To derive the autoradiograph shown in FIG. 3B, monocytes were treated with dexamethasone (1 µM), IL-1β (10 half-maximal units, Collaborative Research), or both for the indicated times prior to RNA isolation. Cycloheximide (25 µM; Sigma) was added to one set of incubations 15 min prior to the addition of cytokine or hormone.

6.2. RESULTS

6.2.1. IDENTIFICATION AND CHARACTERIZATION OF PGHS-2

A directionally cloned cDNA library was constructed in lambda ZAP II from sucrose gradient fractions enriched in the 4 kb mRNA identified in O'Banion, et al., 1991, J. Biol. Chem., 35:23261–23267 and screened with a radiolabelled portion of the 2.8 kb PGHs cDNA under conditions of lowered stringency. Several positive plaques were isolated and analyzed. One, about 4.1 kb in length, was fully sequenced. This clone encodes a 70 kDa protein specifically precipitated by anticyclooxygenase serum, which migrates identically with the immunoprecipitated protein product from in vitro translated poly A-mRNA. Primer extension analysis, using a 20-mer starting at nt 75 of the sequence, indicated that transcription starts 24 bases upstream of the cDNA clone. Comparison of the 4.1 kb sequence (FIG. 1) with that of the previously cloned 2.8 kb PGHS cDNA from mice (which is very similar to that cloned from sheep and human tissues), revealed a single open reading frame with 64% amino acid identity to the protein encoded by the 2.8 kb PGHS cDNA. The deduced protein sequences are colinear except that the 4.1 kb cDNA has shorter amino-terminus and longer carboxy-terminus. The full sequence has been deposited in GenBank, accession number M88242.

6.2.2. PGHS-2 cDNA EXPRESSION IN COS CELLS PRODUCED A FUNCTIONAL PROSTAGLANDIN H SYNTHASE

Two-dimensional gel electrophoresis of $^{35}$S-labeled proteins from transfected cells showed a protein doublet (72/74 kDa, pI 7.5) in the 4.1 kb cDNA-expressing cells that corresponds exactly to the immunoprecipitated cyclooxygenase protein doublet observed in C127 mouse fibroblasts whose synthesis is increased by growth factors and decreased by glucocorticoid hormones.

Transfected cells were also assayed for cyclooxygenase activity. COS cells expressing the 4.1 kb cDNA produced nearly two orders of magnitude more prostaglandin E$_2$ than control cells (Table 2). Furthermore, prostaglandin production increased with the amount of transfected DNA. These results unequivocally demonstrate that the 4.1 kb mRNA enclodes an active cyclooxygenase which was designated "glucocorticoid-regulated inflammatory PGHS (griPGHS).

TABLE 2

Expression of the 4.1 kb cDNA in COS cells leads to prostaglandin synthesis. Subconfluent COS A.2 cells in duplicate 60 mm plates were transfected with the indicated amounts of expression vector alone (SVL) or the expression vector containing the 4.1 kb cDNA (SVL-4.1) and assayed for PGE$_2$ production 2 days later.

| DNA | Amount | pg PGE$_2$/µg protein |
|---|---|---|
| None | — | 0.56, 0.58, 0.51, 0.50 |
| SVL | 2.5 µg | 0.55, 0.68 |
| SVL | 5.0 µg | 0.63, 0.65 |
| SVL-4.1 | 2.5 µg | 14.8, 24.6 |
| SVL-4.1 | 5.0 µg | 63.8, 42.4 |

6.2.3. DEXAMETHASONE SPECIFICALLY REDUCES EXPRESSION OF PGHS-2 AND NOT PGHS-1 IN HUMAN MONOCYTES

FIGS. 3A–3B depicts Northern blots of total monocyte RNA and demonstrates that a 4.8-kb mRNA species is detected with the mouse griPGHS 4.1-kb probe. When normalized to the hybridization signal for β-tubulin, griPGHS mRNA levels are down-regulated by dexamethasone at 4 hr (5-fold in this example), while the level of the 2.8-kb PGHS mRNA is not affected. In this experiment, the level of accumulated $PGE_2$ in the supernatant after 4 hr of incubation was reduced by dexamethasone from 122.5 to 52.5 pg per $10^4$ monocytes. In another experiment, monocytes treated with IL-1β showed increased levels of griPGHS mRNA at 4 hr (2.5-fold relative to control) and 12 hr (14-fold) (FIGS. 3A–3B). These increases were significantly blunted when dexamethasone was present. Furthermore, the IL-1β induction and dexamethasone repression of griPGHS mRNA abundance occurred in the presence of cycloheximide, where superinduction of the 4.8-kb mRNA was clearly evident (FIGS. 3A–3B). In contrast, levels of the 2.8-kb mRNA were not significantly altered relative to β-tubulin by IL-1β, dexamethasone, or cycloheximide treatment.

7. EXAMPLE: DRUG ASSAYS USING PGHS-2 TRANSFECTANTS

The subsections below describe an assay employing the PGHS-2 transfectants of the previous example to determine a test compound's ability to modulate the effects of PGHS-2. It is shown that transformed cell lines stably produce prostaglandin. In addition, it is shown that several known drugs are potent inhibitors of PGHS-2 activity.

7.1. MATERIALS AND METHODS
7.1.1. EXPRESSION VECTOR CONSTRUCTION

Following the methodology of Short et al., 1988, Nucleic Acids Res., 16:7583–7600, the 4.1 griPGHS cDNA clone was excised in vivo from the lambda ZAP II vector and the resulting griPGHS-Bluescript construct isolated on ampicillin plates. griPGHS was prepared for directional subcloning into the pRC/CMV expression vector (Invitrogen) by digestion with AccI, Klenow fill-in, and digestion with Not I. This fragment, extending from the Not I site 50 bases upstream of the cDNA end to nt 1947 of the cDNA, was isolated by gel electrophoresis and contains the full-coding region truncated immediately before any 5'-AUUUA-3' mRNA destabilizing regions. The pRc/CMV vector DNA was digested with Xba I, filled in with Klenow, then digested with Not I. It was further prepared by calf intestinal alkaline phosphatase treatment. Ligated pRc/CMV-griPGHS recombinants were isolated from ampicillin plates following transformation into competent DH5α cells (Library Efficiency; Life Technologies), and were confirmed by restriction analysis of DNA mini-prepgs. The construct is illustrated in FIG. 4.

7.1.2. TRANSFECTION AND ESTABLISHMENT OF STABLE CELL LINES

Sixty-mm plates of subconfluent COS A2 cells, which contain little or no autologous cyclooxygenase activity, were transfected with 1 or 2.5 μg of purified griPGHS-pRC/CMV, or the vector alone, by lipofection for 23 hr following the manufacturer's directions (Life Technologies). After 2 days of growth in normal media (DMEM+10% fetal bovine serum), transfected cells were switched to media containing 800 μg/ml of Geneticin (G418, active component 657 μg/ml; Life Technologies), a concentration previously found to be toxic for COS cells. The media was changed every 3 days, and after 2 weeks, many individual colonies were observed in the dishes transfected with either recombinant or vector alone, but not in the dishes with no transfected DNA. A total of 36 griPGHS pRc/CMV-transfected and 12 vector-transfected colonies were isolated using cloning cylinders. The majority of these survived continued selection in 800 μg/ml G418 during clonal line expansion. Established cultures are maintained in DMEM+10% fetal bovine serum with 400 μg/ml G418.

7.1.3. DRUG SCREENING STUDIES

Prostaglandin assays were carried out as described above. For drug studies, cells were exposed to various concentrations of drugs for 30 min in serum-free DMEM and arachidonic acid was added directly from a 25x stock in DMEM. Supernatants were harvested 15 min later. Controls consisted of no drugs and wells treated with maximal concentrations of drug vehicles (1% methanol or ethanol). Drugs were obtained from Sigma and prepared as 200 mM stock solutions (acetaminophen and ibuprofen in methanol, indomethacin in ethanol and naproxen in water).

7.2. RESULTS
7.2.1. EXPRESSION VECTORS

The pRC/CMV eukaryotic expression vector (FIG. 4) provides several distinct advantages. In addition to the ease of selection in both bacterial and eukaryotic hosts, expression of the present cloned cDNA is driven by a strong CMV promoter. The vector also provides a poly-A signal that is necessary since the present construct does not contain griPGHS 3' untranslated sequences (it ends 12 base pairs (bp) from the translation termination codon). The removal of these sequences is important since in vivo they provide signals (5'-AUUUA-3') for rapid mRNA degradation. Finally, the vector is well suited for use in COS cells which have little or no autologous cyclooxygenase activity.

7.2.2. CELL LINE CHARACTERIZATION

Of the 36 griPGHS-pRc/CMV- and 12 vector alone-cloned neomycin resistant colonies, 29 and 9, respectively, were tested for $PGE_2$ production. In all cases, vector-alone transfectants produced less than 8 μg of $PGE_2$ per assay (number reflects the amount of $PGE_2$ secreted after 10 or 15 min in 20 μl of collected media), whereas the griPGHS transfected clones showed a wide range of prostaglandin production. Of these, eleven prostaglandin-producing and 2 vector-alone containing clones were further expanded and retested.

The amount of $PGE_2$ secreted by the clones harboring the griPGHS construct varied form 10.6 to 72.2 pg/μg cell protein (Table 3).

TABLE 3

| $PGE_2$ production by various cell lines | |
|---|---|
| Cell Line | pg $PGE_2$/μg cell protein |
| A2 | 4.4 |
| A5 | 1.9 |
| E1 | 16.7 |
| E7 | 23.6 |
| E8 | 46.8 |
| E9 | 30.5 |
| E11 | 34.2 |
| F3 | 40.0 |
| F4 | 10.6 |
| F6 | 12.2 |
| F8 | 72.1 |
| F14 | 3.5** |
| F15 | 16.8 |

The values in column 2 represent the amount of prostaglandin secreted during a 10 min exposure to 30 μM arachidonic acid and are normalized to total recovered cellular protein. Cell lines A2 and A5 contain the vector alone and the remaining cells were transfected with griPGHS-pRc/

CMV. Note that only one (F14, marked by double asterisk, "**") showed no increase PGE$_2$ production over cells harboring the vector alone.

Each of these lines was expanded for cryopreservation and one (E9), chosen for ease of culturing and its significant PGE$_2$ production, was used in further studies. A sample of this cell line has been deposited in the American Type Culture Collection, Rockville, Md., U.S.A. under the provisions of the Budapest Treaty and assigned accession number ATCC 11119.

7.2.3. STABILITY OF PGE$_2$ PRODUCTION

Stable expression of cyclooxygenase activity in the E9 cell line was tested by comparing PGE$_2$ production over at least 5 passages of the cell line. After 6 weeks, these cells were still producing high levels of PGE$_2$. Although the numbers are not directly comparable, since cell numbers were not normalized by protein determination in all cases, the amount of PGE$_2$ secreted by E9 cells in this standard assay ranged form 35 pg to 90 pg (per 20 $\mu$l assayed media). Furthermore, within an experiment, E9 cells showed very consistent levels of PGE$_2$ production from well to well. For example, for 12 tested supernatants, PGE$_2$ levels were 48.4±3.5 pg/20 $\mu$l (mean±SEM).

7.2.4. DRUG SCREENING STUDIES

To illustrate the utility of the above described cell lines in drug testing, duplicate wells of the E9 cells were exposed to a range of doses (0.2 $\mu$M - 2 mM) of four non-steroidal anti-inflammatory drugs: acetaminophen, ibuprofen, naproxen, and indomethacin. Cells were placed in serum-free medium with the drugs for 30 min prior to a 15 min exposure to arachidonic acid (added directly to the media). Synthesized PGE$_2$ was then quantitated from the supernatants by a standard radio immunoassay. Results, shown in FIG. 5, reveal specific dose-response curves for each drug with indomethacin showing the most and acetaminophen the least potency against griPGHS activity. The maximal inhibition in each case (except for acetaminophen where 2 mM was apparently not sufficient for full inhibition) was similar to that seen for COS cells harboring the vector alone (3–8 pg). Low doses of each drug gave levels corresponding to the untreated control values which averaged at 48.4 pg. Note that controls run both with and without 1% drug vehicle (ethanol or ethanol; comparable to exposure in the 2 mM drug conditions) showed no differences in PGE$_2$ production.

8. EXAMPLE: PREPARATION OF MICROSOMAL EXTRACTS AND IN VITRO TESTING OF CYCLOOXYGENASE ACTIVITY

The paragraphs below describe a method for determining cellular cyclooxygenase activity by preparing microsomal extracts of the cells to be tested and then testing the extracts for cyclooxygenase activity. In addition, it is shown that the effects of a test compound on cyclooxygenase activity can also be determined.

Microsomal extracts and measurements of cellular cyclooxygenase activity are performed essentially as described by Raz et al., 1988, J. Biol. Chem., 263:3022–3025; and Raz, et al., 1989, Proc. Nat'l. Acad. Sci. USA, 86:1657–1661. Cells are rinsed once with ice-cold PBS (pH=7.4), scraped from dishes with a plastic disposable scraper (Life Technologies), transferred to 1.5 ml microfuge tubes with ice-cold PBS, and pelleted by centrifugation (8 minutes at 800×g). The supernatants are removed and the cell pellets rinsed with additional PBS. Cell pellets can be stored at −70° C. at this point.

To prepare extracts, the pellets are resuspended in solubilization buffer (50 mM Tris, 1 mM diethyldithiocarbamic acid (sodium salt), 10 mM EDTA, 1% (v/v) Tween-20 and 0.2 mg/ml $\alpha_2$-macroglobulin, pH-8.0), followed by sonication (5×10 sec bursts, low power setting). Extracts are clarified by centrifugation at 4° C. (20 minutes at 16,000×g). Aliquots are taken for protein determination, and 50 $\mu$l aliquots are diluted to 500 $\mu$l with a solution containing 100 mM NaCl, 20 mM sodium borate, 1.5 mM EDTA, 1.5 mM EGTA, 0.3 mM PMSF, 10 mM NEM, 0.5% BSA, 0.5% Triton X-100, 1 mM epinephrine and 1 mM phenol (pH=9.0).

Reactions are initiated by the addition of arachidonic acid in the above buffer to 100 $\mu$M of microsomal extract and incubated for 30 minutes at 37° C. The PGE$_2$ formed is measured by RIA after quantitative conversion to the methyl oximated form as described by the RIA kit manufacturer (Amersham). To test the effects of non-steroidal anti-inflammatory compounds, different dosages of drugs are added 5 min prior to initiating the reaction with arachidonic acid.

9. EXAMPLE: ISOLATION, CLONING AND SEQUENCING OF HUMAN PGHS-2

The subsections below describe the identification and sequence of human PGHS-2. In addition, it is shown that transformed cell lines stably express PGHS-1 and PGHS-2.

9.1. MATERIALS AND METHODS 9.1.1. GENERATION OF HUMAN PGHS-1 AND HUMAN PGHS-2 cDNA CLONES

RNA was isolated from a human fibroblast cell line (W138) treated with serum and cycloheximide for 4 hr. Total RNA isolation was done by guanidinium lysis followed by CsCl cushion centrifugation (Chirgwin et al., 1979. Biochem., 18:5294–5299. Polymerase chain reaction (PCR) primers specific for the human PGHS-1 and PGHS-2 sequences were engineered to amplify the coding regions of either one transcript or the other (Table 4). The 5' end primers contained a Hind III restriction site and the 3' end primers contained a Not I restriction site for subsequent cloning. Reverse transcriptase polymerase chain reactions (RT-PCR) carried out as described by Kawasaski, 1990, PCR Protocols: A Guide to Methods and Applications, M. A. Innis et al., eds., Academic Press, NY, using the specific primers generated PCR products about 2 kb in size.

TABLE 4

| PCR Primers |
|---|
| A. Human PGHS-1 PCR Primers |
|   NotI |
| 5'-CTTACCCGAAGCTTGCGCCATGAGCCGG-3' (SEQ ID NO:10) |
|    3'-CGAGACTCCCCGTCGCCGGCGATTGCTT-5' (SEQ ID NO:11) |
|       HindIII |
| B. Human PGHS-2 PCR Primers |
|   NotI |
| 5'-TCATTCTAAGCTTCCGCTGCGATGCTCGC-3' (SEQ ID NO:12) |
|    3'-GACATCTTCAGATTACGCCGGCGTACTAG-5' (SEQ ID NO:13) |
|       HindIII |

9.1.2. GENERATION OF PLASMID CONSTRUCTS FOR TRANSFECTION AND SEQUENCING

Following purification and digestion with HindIII and NotI, the two PCR products were each ligated into pRC/CMV vectors (Invitrogen) (see FIG. 4). Ligated pRC/CMV-PGHS recombinant plasmids were isolated from ampicillin plates following transformation into competent DH5a cells (Life Technologies). Clones were screened for the presence of PGHS inserts by restriction mapping. Three PGHS-2 clones were sequenced in both directions on an Applied Biosystems automated sequencer Model #373A.

9.1.3. GENERATION OF STABLY TRANSFECTED MAMMALIAN CELL LINES

Sixty-mm plates of 50% confluent COS-A2 (monkey-kidney) cells, which contain little or no cyclooxygenase activity were transfected with 1–2.5 µg of purified pRC/CMV;hPGHS-2 plasmid, pRC/CMV;hPGHS-1 plasmid or the PRC/CMV vector alone by a calcium phosphate precipitation method (Chen et al., 1987, Mol. Cell. Biol., 7:2745–2752. Plates were incubated at 35° C., 3% $CO_2$ for 24 hr in normal media (Dulbecco's modified Eagle Media (DMEM)+10% fetal bovine serum). After two rinses with warm DMEM, plates were transferred to 37° C., 5% $CO_2$ for an additional 24 hr. Selection was then started with normal media containing 800 µg/ml of Geneticin (active component G418, 657 µg/ml, Life Technologies), a concentration which is toxic for COS cells. The media was changed every 3 days and after 2 weeks, many individual colonies were observed in the dishes transfected with either recombinant PGHS vector or vector alone, but not in the dishes with no transfected DNA. Twelve to twenty-four colonies from each transfection were isolated using cloning cylinders. The majority of these survived continued G418 selection during clonal cell-line expansion. Established cultures are maintained in DMEM+10% fetal bovine serum with 400 µg/ml G418.

9.1.4. TESTING THE G418 RESISTANT CELL LINES AND CONFIRMING THE STABLE EXPRESSION OF PGHS-2 AND PGHS-1 ACTIVITY

Transfected COS cells plated in 12-well plates were grown to near confluence, rinsed twice with warm serum-free media and then covered with 300 µl of media containing 30 µM arachidonic acid (sodium salt; Sigma). After 15 min, supernatants were placed in Eppendorf tubes on ice, clarified by centrifugation at 15,000×g for 2 min, and assayed for PGE production by immunoassay alter conversion to the methyl oximated form (kit from Amersham).

Cell monolayers were solubilized in 0.5M NaOH and neutralized with 1M HCl for protein concentration determinations using reagents from BioRad (modified Bradford Assay). Cell lines expressing PGHS activity were further expanded and then frozen down in media with 10% DMSO.

9.2. RESULTS 9.2.1. SEQUENCE OF HUMAN PGHS-2

The clone comprising the PGHS-2 gene sequence depicted in FIGS. 6A–6B was selected for transfection. This sequence differs from the human PGHS-2 sequence disclosed by Hla and Neilson, 1992, Proc. Nat'l. Acad. Sci. USA, 89:7384–7388, due to a glutamic acid (E) rather than a glycine (w) at amino acid position 165 of the PGHS-2 gene product (FIG. 7). The sequence for the PGHS-2 gene was confirmed by establishing the identity of the sequences of two other hPGHS-2 clones obtained from separate PCR runs, which demonstrates that the difference observed is not a PCR artifact. Furthermore, as shown in FIG. 1, mouse PGHS-2 also has a glutamic acid at this position. PGHS-1 clones were similarly screened and the sequences of the PGHS-1 gene and enzyme confirmed to be identical to that shown in FIG. 2 (SEQ ID NO:6) in Yokahama and Tanabe, 1984 Biochem. Biophys. Res. Commun., 165:888–894; see also, Hla, 1986, Prostaglandins, 32:829–845.

9.2.2. TRANSFORMED CELL LINES STABLY EXPRESSED PGHS-1 AND PGHS-2

Cell line 4B4 expressing PGHS-2 and cell line H17A5 expressing PGHS-1 were deposited on Mar. 5, 1993 in the American Type Culture Collection, Rockville, Md., USA (cell line 4B4 was assigned ATCC accession number CRL 11284; cell line H17A5 was assigned ATCC CRL 11283).

Levels of PGHS expression in the stably transformed cell lines varied and were much higher for PGHS-1 cell lines in comparison to PGHS-2 cell lines, as shown by the data in Table 5.

TABLE 5

$PGE_2$ Production in Stably Transformed COS Cell Lines

| Human PGHS-1 Cell Lines (pRC/CMV;hPGHS-1) | | Human PGHS-2 Cell Lines (pRC/CMV;hPGHS-1) | |
|---|---|---|---|
| Line | Level[a] | Line | Level[a] |
| H17A1 | 0.4 | 2A2 | 5.5 |
| H17A3 | 2500 | 2B1 | 4.0 |
| H17A5* | 2500+ | 2B2 | 37.5 |
| H17A6 | 73.5 | 2B3 | 31.6 |
| H17B3 | 145 | 2B6 | 29.0 |
| H22A2 | 2036 | 4A1 | 36.2 |
| H22A5 | 40.3 | 4A2 | 0.4 |
| H22B2 | 73.5 | 4A3 | 0.6 |
| H22B3 | 568 | 4A4 | 8.2 |
| H22B4 | 9.2 | 4A5 | 9.8 |
| | | 4A6 | 7.2 |
| | | 4B1 | 24.6 |
| | | 4B2 | 4.8 |
| | | 4B3 | 13.1 |
| | | 4B4* | 58.0 |
| | | 4B5 | 10.6 |

*Pg $PGE_2$/15 min/µg cellular protein; COS-A2 = 0.4; COS-A2 + pRC/CMV vector = 0.4

The cell lines have maintained high levels of PGHS expression even after many months of culturing. For example, the cell line 4B4 has been tested 6 times over 5 months and expression has ranged from 50–60 pg $PGE_2$/µg cellular protein. The exclusive presence of either PGHS-1 or PGHS-2 in the cell lines was confirmed by Northern analyses using hybridization probes that are specific for either PGHS-1 or PGHS-2.

10. EXAMPLE: NONSTEROIDAL ANTI-INFLAMMATORY DRUG (NSAID) STUDIES ON STABLE HUMAN PGHS-1 AND PGHS-2 CELL LINES

The text below describes the effects of various concentrations of NSAID on the ability of PGHS-1 and PGHS-2 cell lines to produce prostaglandin.

PGHS-1 and PGHS-2 cell lines (including 4B4 and H17A5) were exposed to various concentrations of NSAID for 30 min in serum-free DMEM. Arachidonic acid was added directly from a 25x stock in DMEM and supernatants were harvested 15 min later. Controls consisted of no drug treatment and cells treated with the maximal concentrations of drug vehicles (1% methanol or ethanol). Drugs were obtained from Sigma Chem. Co. and prepared as 200 mM stock solutions (aspirin and ibuprofen in methanol, indomethacin in ethanol, and naproxen in water). Cyclooxygenase activity was determined as described herein above. Distinctly different dose-response curves that were characteristic for either the PGHS-1 or PGHS-2 cell lines were observed. Particularly as shown in FIGS. 8A–8D and 9A–9D for indomethacin and aspirin, the levels of drug required for inhibition were different for the cells expressing PGHS-1 versus those expressing PGHS-2 (FIGS. 8A–8D and 9A–9D).

All publications, patents and patent applications are herein incorporated by reference to the same extent as if each individual publication or patent application was specifically and individually indicated to be incorporated by reference.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

11. DEPOSIT OF MICROORGANISMS

The following microorganisms have been deposited with the American Type Culture Collection, (ATCC), Rockville, Maryland and have been assigned the following accession numbers:

| Microorganism Strain Designation | Date of Deposit | Accession No. |
| --- | --- | --- |
| A1.2 p5 2/20/95 | June 7, 1995 | CRL 11924 |
| hPGHS-2 A2.7 p6 11/3/93 | June 7, 1995 | CRL 11923 |

What is claimed is:

1. A method for identifying a compound that inhibits prostaglandin synthesis catalyzed by mammalian prostaglandin H synthase-2 (PGHS-2) comprising:

(a) contacting a genetically engineered host cell that contains a sequence encoding mammalian PGHS-2 operatively associated with a regulatory sequence that controls gene expression, so that a PGHS-2 gene product is stably expressed by the host cell, with the compound in the presence of a pre-determined amount of arachidonic acid;

(b) measuring the conversion of the arachidonic acid to its prostaglandin metabolite; and (c) comparing the amount of arachidonic acid converted by the cells exposed to the test compound to the amount of arachidonic acid converted by control cells that were not exposed to the test compound.

2. The method of claim 1 in which the genetically engineered cell contains a sequence encoding mammalian PGHS-2 operatively associated with a regulatory sequence that controls gene expression, so that the mammalian PGHS-2 gene product is stably expressed by the host cell, wherein said sequence does not express PGHS-1.

3. The method of claim 1 in which the genetically engineered cell contains a sequence encoding a mammalian PGHS-2 operatively associated with a regulatory sequence that controls gene expression, so that a PGHS-2 gene product is stably expressed by the host cell, and in which the host cell is a mammalian cell that does not express autologous PGHS-2.

4. The method of claim 1 in which the genetically engineered host cell is designated hPGHS-2 A2.7 p6 Nov. 7, 1993 as deposited with the ATCC having accession no. CRL11923, or progeny thereof expressing PGHS-2.

5. A method for identifying a compound that inhibits prostaglandin synthesis catalyzed by mammalian PGHS-2, but does not inhibit the activity of PGHS-1, comprising:

(a) contacting a genetically engineered cell that expresses mammalian PGHS-2, and not mammalian PGHS-1, with the compound in the presence of a pre-determined amount of arachidonic acid;

(b) contacting a genetically engineered cell that expresses mammalian PGHS-1, and not mammalian PGHS-2, with the compound in the presence of a predetermined amount of arachidonic acid;

(c) measuring the conversion of arachidonic acid to its prostaglandin metabolite; and (d) comparing the amount of arachidonic acid converted by each cell exposed to the test compound to the amount of arachidonic acid converted by control cells that were not exposed to the test compound, so that compounds that inhibit PGHS-2 and not PGHS-1 activity are identified.

6. The method of claim 5 in which the PGHS-2 expressing cell line is designated hPGHS-2 A2.7 p6 Nov. 7, 1993 as deposited with the ATCC having accession no. CRL11923, or progeny thereof expressing PGHS-2.

7. The method of claim 5 in which the PGHS-1 expressing cell line is designated A1.2 p5 Feb. 20, 1995 as deposited with the ATCC having accession no. CRL11924, or progeny thereof expressing PGHS-1.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 1920 base pairs
( B ) TYPE: nucleic acid
( C ) STRANDEDNESS: single
( D ) TOPOLOGY: unknown ( i i ) MOLECULE TYPE: cDNA ( i x ) FEATURE:
( A ) NAME/KEY: CDS
( B ) LOCATION: 101..1912

( x i ) SEQUENCE DESCRIPTION: SEQ ID NO:1:

```
CTTCAGGAGT  CAGTCAGGAC  TCTGCTCACG  AAGGAACTCA  GCACTGCATC  CTGCCAGCTC                60

CACCGCCACC  ACTACTGCCA  CCTCCGCTGC  CACCTCTGCG  ATG  CTC  TTC  CGA  GCT              115
                                                  Met  Leu  Phe  Arg  Ala
                                                   1                    5

GTG  CTG  CTC  TGC  GCT  GCC  CTG  GGG  CTC  AGC  CAG  GCA  GCA  AAT  CCT  TGC       163
Val  Leu  Leu  Cys  Ala  Ala  Leu  Gly  Leu  Ser  Gln  Ala  Ala  Asn  Pro  Cys
                         10                        15                        20

TGT  TCC  AAT  CCA  TGT  CAA  AAC  CGT  GGG  GAA  TGT  ATG  AGC  ACA  GGA  TTT       211
Cys  Ser  Asn  Pro  Cys  Gln  Asn  Arg  Gly  Glu  Cys  Met  Ser  Thr  Gly  Phe
                25                        30                        35

GAC  CAG  TAT  AAG  TGT  GAC  TGT  ACC  CGG  ACT  GGA  TTC  TAT  GGT  GAA  AAC       259
Asp  Gln  Tyr  Lys  Cys  Asp  Cys  Thr  Arg  Thr  Gly  Phe  Tyr  Gly  Glu  Asn
           40                        45                        50

TGT  ACT  ACA  CCT  GAA  TTT  CTG  ACA  AGA  ATC  AAA  TTA  CTG  CTG  AAG  CCC       307
Cys  Thr  Thr  Pro  Glu  Phe  Leu  Thr  Arg  Ile  Lys  Leu  Leu  Leu  Lys  Pro
      55                        60                        65

ACC  CCA  AAC  ACA  GTG  CAC  TAC  ATC  CTG  ACC  CAC  TTC  AAG  GGA  GTC  TGG       355
Thr  Pro  Asn  Thr  Val  His  Tyr  Ile  Leu  Thr  His  Phe  Lys  Gly  Val  Trp
 70                        75                        80                        85

AAC  ATT  GTG  AAC  AAC  ATC  CCC  TTC  CTG  CGA  AGT  TTA  ATC  ATG  AAA  TAT       403
Asn  Ile  Val  Asn  Asn  Ile  Pro  Phe  Leu  Arg  Ser  Leu  Ile  Met  Lys  Tyr
                         90                        95                       100

GTG  CTG  ACA  TCC  AGA  TCA  TAT  TTG  ATT  GAC  AGT  CCA  CCT  ACT  TAC  AAT       451
Val  Leu  Thr  Ser  Arg  Ser  Tyr  Leu  Ile  Asp  Ser  Pro  Pro  Thr  Tyr  Asn
                   105                       110                       115

GTG  CAC  TAT  GGT  TAC  AAA  AGC  TGG  GAA  GCC  TTC  TCC  AAC  CTC  TCC  TAC       499
Val  His  Tyr  Gly  Tyr  Lys  Ser  Trp  Glu  Ala  Phe  Ser  Asn  Leu  Ser  Tyr
              120                       125                       130

TAC  ACC  AGG  GCC  CTT  CCT  CCC  GTA  GCA  GAT  GAC  TGC  CCA  ACT  CCC  ATG       547
```

```
Tyr Thr Arg Ala Leu Pro Pro Val Ala Asp Asp Cys Pro Thr Pro Met
    135             140                 145

GGT GTG AAG GGA AAT AAG GAG CTT CCT GAT TCA AAA GAA GTG CTG GAA         595
Gly Val Lys Gly Asn Lys Glu Leu Pro Asp Ser Lys Glu Val Leu Glu
150             155                 160                 165

AAG GTT CTT CTA CGG AGA GAG TTC ATC CCT GAC CCC CAA GGC TCA AAT         643
Lys Val Leu Leu Arg Arg Glu Phe Ile Pro Asp Pro Gln Gly Ser Asn
                170                 175                 180

ATG ATG TTT GCA TTC TTT GCC CAG CAC TTC ACC CAT CAG TTT TTC AAG         691
Met Met Phe Ala Phe Phe Ala Gln His Phe Thr His Gln Phe Phe Lys
                185                 190                 195

ACA GAT CAT AAG CGA GGA CCT GGG TTC ACC CGA GGA CTG GGC CAT GGA         739
Thr Asp His Lys Arg Gly Pro Gly Phe Thr Arg Gly Leu Gly His Gly
            200                 205                 210

GTG GAC TTA AAT CAC ATT TAT GGT GAA ACT CTG GAC AGA CAA CAT AAA         787
Val Asp Leu Asn His Ile Tyr Gly Glu Thr Leu Asp Arg Gln His Lys
        215                 220                 225

CTG CGC CTT TTC AAG GAT GGA AAA TTG AAA TAT CAG GTC ATT GGT GGA         835
Leu Arg Leu Phe Lys Asp Gly Lys Leu Lys Tyr Gln Val Ile Gly Gly
230             235                 240                 245

GAG GTG TAT CCC CCC ACA GTC AAA GAC ACT CAG GTA GAG ATG ATC TAC         883
Glu Val Tyr Pro Pro Thr Val Lys Asp Thr Gln Val Glu Met Ile Tyr
                250                 255                 260

CCT CCT CAC ATC CCT GAG AAC CTG CAG TTT GCT GTG GGG CAG GAA GTC         931
Pro Pro His Ile Pro Glu Asn Leu Gln Phe Ala Val Gly Gln Glu Val
                265                 270                 275

TTT GGT CTG GTG CCT GGT CTG ATG ATG TAT GCC ACC ATC TGG CTT CGG         979
Phe Gly Leu Val Pro Gly Leu Met Met Tyr Ala Thr Ile Trp Leu Arg
            280                 285                 290

GAG CAC AAC AGA GTG TGC GAC ATA CTC AAG CAG GAG CAT CCT GAG TGG        1027
Glu His Asn Arg Val Cys Asp Ile Leu Lys Gln Glu His Pro Glu Trp
        295                 300                 305

GGT GAT GAG CAA CTA TTC CAA ACC AGC AGA CTC ATA CTC ATA GGA GAG        1075
Gly Asp Glu Gln Leu Phe Gln Thr Ser Arg Leu Ile Leu Ile Gly Glu
310             315                 320                 325

ACT ATC AAG ATA GTG ATC GAA GAC TAC GTG CAA CAC CTG AGC GGT TAC        1123
Thr Ile Lys Ile Val Ile Glu Asp Tyr Val Gln His Leu Ser Gly Tyr
                330                 335                 340

CAC TTC AAA CTC AAG TTT GAC CCA GAG CTC CTT TTC AAC CAG CAG TTC        1171
His Phe Lys Leu Lys Phe Asp Pro Glu Leu Leu Phe Asn Gln Gln Phe
                345                 350                 355

CAG TAT CAG AAC CGC ATT GCC TCT GAA TTC AAC ACA CTC TAT CAC TGG        1219
Gln Tyr Gln Asn Arg Ile Ala Ser Glu Phe Asn Thr Leu Tyr His Trp
            360                 365                 370

CAC CCC CTG CTG CCC GAC ACC TTC AAC ATT GAA GAC CAG GAG TAC AGC        1267
His Pro Leu Leu Pro Asp Thr Phe Asn Ile Glu Asp Gln Glu Tyr Ser
375                 380                 385

TTT AAA CAG TTT CTC TAC AAC AAC TCC ATC CTC CTG GAA CAT GGA CTC        1315
Phe Lys Gln Phe Leu Tyr Asn Asn Ser Ile Leu Leu Glu His Gly Leu
390                 395                 400                 405

ACT CAG TTT GTT GAG TCA TTC ACC AGA CAG ATT GCT GGC CGG GTT GCT        1363
Thr Gln Phe Val Glu Ser Phe Thr Arg Gln Ile Ala Gly Arg Val Ala
                410                 415                 420

GGG GGA AGA AAT GTG CCA ATT GCT GTA CAA GCA GTG GCA AAG GCC TCC        1411
Gly Gly Arg Asn Val Pro Ile Ala Val Gln Ala Val Ala Lys Ala Ser
                425                 430                 435

ATT GAC CAG AGC AGA GAG ATG AAA TAC CAG TCT CTC AAT GAG TAC CGG        1459
Ile Asp Gln Ser Arg Glu Met Lys Tyr Gln Ser Leu Asn Glu Tyr Arg
                440                 445                 450

AAA CGC TTC TCC CTG AAG CCG TAC ACA TCA TTT GAA GAA CTT ACA GGA        1507
```

| | | | | | | | | | | | | | | | |
|---|---|---|---|---|---|---|---|---|---|---|---|---|---|---|---|
| Lys | Arg | Phe | Ser | Leu | Lys | Pro | Tyr | Thr | Ser | Phe | Glu | Glu | Leu | Thr | Gly |
| | 455 | | | | 460 | | | | | 465 | | | | | |

| GAG | AAG | GAA | ATG | GCT | GCA | GAA | TTG | AAA | GCC | CTC | TAC | AGT | GAC | ATC | GAT | 1555 |
|---|---|---|---|---|---|---|---|---|---|---|---|---|---|---|---|---|
| Glu | Lys | Glu | Met | Ala | Ala | Glu | Leu | Lys | Ala | Leu | Tyr | Ser | Asp | Ile | Asp | |
| 470 | | | | | 475 | | | | | 480 | | | | | 485 | |

| GTC | ATG | GAA | CTG | TAC | CCT | GCC | CTG | CTG | GTG | GAA | AAA | CCT | CGT | CCA | GAT | 1603 |
|---|---|---|---|---|---|---|---|---|---|---|---|---|---|---|---|---|
| Val | Met | Glu | Leu | Tyr | Pro | Ala | Leu | Leu | Val | Glu | Lys | Pro | Arg | Pro | Asp | |
| | | | | 490 | | | | | 495 | | | | | 500 | | |

| GCT | ATC | TTT | GGG | GAG | ACC | ATG | GTA | GAG | CTT | GGA | GCA | CCA | TTC | TCC | TTG | 1651 |
|---|---|---|---|---|---|---|---|---|---|---|---|---|---|---|---|---|
| Ala | Ile | Phe | Gly | Glu | Thr | Met | Val | Glu | Leu | Gly | Ala | Pro | Phe | Ser | Leu | |
| | | | 505 | | | | | 510 | | | | | 515 | | | |

| AAA | GGA | CTT | ATG | GGA | AAT | CCC | ATC | TGT | TCT | CCT | CAA | TAC | TGG | AAG | CCG | 1699 |
|---|---|---|---|---|---|---|---|---|---|---|---|---|---|---|---|---|
| Lys | Gly | Leu | Met | Gly | Asn | Pro | Ile | Cys | Ser | Pro | Gln | Tyr | Trp | Lys | Pro | |
| | | | 520 | | | | 525 | | | | | 530 | | | | |

| AGC | ACC | TTT | GGA | GGC | GAA | GTG | GGT | TTT | AAG | ATC | ATC | AAT | ACT | GCC | TCA | 1747 |
|---|---|---|---|---|---|---|---|---|---|---|---|---|---|---|---|---|
| Ser | Thr | Phe | Gly | Gly | Glu | Val | Gly | Phe | Lys | Ile | Ile | Asn | Thr | Ala | Ser | |
| | 535 | | | | | 540 | | | | | 545 | | | | | |

| ATT | CAG | TCT | CTC | ATC | TGC | AAT | AAT | GTG | AAG | GGG | TGT | CCC | TTC | ACT | TCT | 1795 |
|---|---|---|---|---|---|---|---|---|---|---|---|---|---|---|---|---|
| Ile | Gln | Ser | Leu | Ile | Cys | Asn | Asn | Val | Lys | Gly | Cys | Pro | Phe | Thr | Ser | |
| 550 | | | | | 555 | | | | | 560 | | | | | 565 | |

| TTC | AAT | GTG | CAA | GAT | CCA | CAG | CCT | ACC | AAA | ACA | GCC | ACC | ATC | AAT | GCA | 1843 |
|---|---|---|---|---|---|---|---|---|---|---|---|---|---|---|---|---|
| Phe | Asn | Val | Gln | Asp | Pro | Gln | Pro | Thr | Lys | Thr | Ala | Thr | Ile | Asn | Ala | |
| | | | | 570 | | | | | 575 | | | | | 580 | | |

| AGT | GCC | TCC | CAC | TCC | AGA | CTA | GAT | GAC | ATT | AAC | CCT | ACA | GTA | CTA | ATC | 1891 |
|---|---|---|---|---|---|---|---|---|---|---|---|---|---|---|---|---|
| Ser | Ala | Ser | His | Ser | Arg | Leu | Asp | Asp | Ile | Asn | Pro | Thr | Val | Leu | Ile | |
| | | | 585 | | | | | 590 | | | | | 595 | | | |

| AAA | AGG | CGT | TCA | ACT | GAG | CTG | TAAAAGTC | | | | | | | | | 1920 |
|---|---|---|---|---|---|---|---|---|---|---|---|---|---|---|---|---|
| Lys | Arg | Arg | Ser | Thr | Glu | Leu | | | | | | | | | | |
| | | 600 | | | | | | | | | | | | | | |

( 2 ) INFORMATION FOR SEQ ID NO:2:

( i ) SEQUENCE CHARACTERISTICS:
        ( A ) LENGTH: 604 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

| Met | Leu | Phe | Arg | Ala | Val | Leu | Leu | Cys | Ala | Ala | Leu | Gly | Leu | Ser | Gln |
|---|---|---|---|---|---|---|---|---|---|---|---|---|---|---|---|
| 1 | | | | 5 | | | | 10 | | | | | | 15 | |

| Ala | Ala | Asn | Pro | Cys | Cys | Ser | Asn | Pro | Cys | Gln | Asn | Arg | Gly | Glu | Cys |
|---|---|---|---|---|---|---|---|---|---|---|---|---|---|---|---|
| | | | 20 | | | | | 25 | | | | | 30 | | |

| Met | Ser | Thr | Gly | Phe | Asp | Gln | Tyr | Lys | Cys | Asp | Cys | Thr | Arg | Thr | Gly |
|---|---|---|---|---|---|---|---|---|---|---|---|---|---|---|---|
| | | 35 | | | | | 40 | | | | | 45 | | | |

| Phe | Tyr | Gly | Glu | Asn | Cys | Thr | Thr | Pro | Glu | Phe | Leu | Thr | Arg | Ile | Lys |
|---|---|---|---|---|---|---|---|---|---|---|---|---|---|---|---|
| | 50 | | | | | 55 | | | | | 60 | | | | |

| Leu | Leu | Leu | Lys | Pro | Thr | Pro | Asn | Thr | Val | His | Tyr | Ile | Leu | Thr | His |
|---|---|---|---|---|---|---|---|---|---|---|---|---|---|---|---|
| 65 | | | | | 70 | | | | | 75 | | | | | 80 |

| Phe | Lys | Gly | Val | Trp | Asn | Ile | Val | Asn | Asn | Ile | Pro | Phe | Leu | Arg | Ser |
|---|---|---|---|---|---|---|---|---|---|---|---|---|---|---|---|
| | | | | 85 | | | | | 90 | | | | | 95 | |

| Leu | Ile | Met | Lys | Tyr | Val | Leu | Thr | Ser | Arg | Ser | Tyr | Leu | Ile | Asp | Ser |
|---|---|---|---|---|---|---|---|---|---|---|---|---|---|---|---|
| | | | 100 | | | | | 105 | | | | | 110 | | |

| Pro | Pro | Thr | Tyr | Asn | Val | His | Tyr | Gly | Tyr | Lys | Ser | Trp | Glu | Ala | Phe |
|---|---|---|---|---|---|---|---|---|---|---|---|---|---|---|---|
| | | | 115 | | | | | 120 | | | | | 125 | | |

| Ser | Asn | Leu | Ser | Tyr | Tyr | Thr | Arg | Ala | Leu | Pro | Pro | Val | Ala | Asp | Asp |
|---|---|---|---|---|---|---|---|---|---|---|---|---|---|---|---|
| | | 130 | | | | | 135 | | | | | 140 | | | |

| Cys | Pro | Thr | Pro | Met | Gly | Val | Lys | Gly | Asn | Lys | Glu | Leu | Pro | Asp | Ser |
|---|---|---|---|---|---|---|---|---|---|---|---|---|---|---|---|
| 145 | | | | | 150 | | | | | 155 | | | | | 160 |

-continued

| Lys | Glu | Val | Leu | Glu | Lys | Val | Leu | Leu | Arg | Arg | Glu | Phe | Ile | Pro | Asp |
|---|---|---|---|---|---|---|---|---|---|---|---|---|---|---|---|
|   |   |   |   | 165 |   |   |   |   | 170 |   |   |   |   | 175 |   |

| Pro | Gln | Gly | Ser | Asn | Met | Met | Phe | Ala | Phe | Phe | Ala | Gln | His | Phe | Thr |
|---|---|---|---|---|---|---|---|---|---|---|---|---|---|---|---|
|   |   |   | 180 |   |   |   |   | 185 |   |   |   |   | 190 |   |   |

| His | Gln | Phe | Phe | Lys | Thr | Asp | His | Lys | Arg | Gly | Pro | Gly | Phe | Thr | Arg |
|---|---|---|---|---|---|---|---|---|---|---|---|---|---|---|---|
|   |   | 195 |   |   |   |   | 200 |   |   |   |   | 205 |   |   |   |

| Gly | Leu | Gly | His | Gly | Val | Asp | Leu | Asn | His | Ile | Tyr | Gly | Glu | Thr | Leu |
|---|---|---|---|---|---|---|---|---|---|---|---|---|---|---|---|
|   | 210 |   |   |   |   | 215 |   |   |   |   | 220 |   |   |   |   |

| Asp | Arg | Gln | His | Lys | Leu | Arg | Leu | Phe | Lys | Asp | Gly | Lys | Leu | Lys | Tyr |
|---|---|---|---|---|---|---|---|---|---|---|---|---|---|---|---|
| 225 |   |   |   |   | 230 |   |   |   |   | 235 |   |   |   |   | 240 |

| Gln | Val | Ile | Gly | Gly | Glu | Val | Tyr | Pro | Pro | Thr | Val | Lys | Asp | Thr | Gln |
|---|---|---|---|---|---|---|---|---|---|---|---|---|---|---|---|
|   |   |   |   | 245 |   |   |   |   | 250 |   |   |   |   | 255 |   |

| Val | Glu | Met | Ile | Tyr | Pro | Pro | His | Ile | Pro | Glu | Asn | Leu | Gln | Phe | Ala |
|---|---|---|---|---|---|---|---|---|---|---|---|---|---|---|---|
|   |   |   | 260 |   |   |   |   | 265 |   |   |   |   | 270 |   |   |

| Val | Gly | Gln | Glu | Val | Phe | Gly | Leu | Val | Pro | Gly | Leu | Met | Met | Tyr | Ala |
|---|---|---|---|---|---|---|---|---|---|---|---|---|---|---|---|
|   |   |   | 275 |   |   |   |   | 280 |   |   |   |   | 285 |   |   |

| Thr | Ile | Trp | Leu | Arg | Glu | His | Asn | Arg | Val | Cys | Asp | Ile | Leu | Lys | Gln |
|---|---|---|---|---|---|---|---|---|---|---|---|---|---|---|---|
|   |   |   | 290 |   |   |   |   | 295 |   |   |   |   | 300 |   |   |

| Glu | His | Pro | Glu | Trp | Gly | Asp | Glu | Gln | Leu | Phe | Gln | Thr | Ser | Arg | Leu |
|---|---|---|---|---|---|---|---|---|---|---|---|---|---|---|---|
| 305 |   |   |   |   | 310 |   |   |   |   | 315 |   |   |   |   | 320 |

| Ile | Leu | Ile | Gly | Glu | Thr | Ile | Lys | Ile | Val | Ile | Glu | Asp | Tyr | Val | Gln |
|---|---|---|---|---|---|---|---|---|---|---|---|---|---|---|---|
|   |   |   |   | 325 |   |   |   |   | 330 |   |   |   |   | 335 |   |

| His | Leu | Ser | Gly | Tyr | His | Phe | Lys | Leu | Lys | Phe | Asp | Pro | Glu | Leu | Leu |
|---|---|---|---|---|---|---|---|---|---|---|---|---|---|---|---|
|   |   |   | 340 |   |   |   |   | 345 |   |   |   |   | 350 |   |   |

| Phe | Asn | Gln | Gln | Phe | Gln | Tyr | Gln | Asn | Arg | Ile | Ala | Ser | Glu | Phe | Asn |
|---|---|---|---|---|---|---|---|---|---|---|---|---|---|---|---|
|   |   |   | 355 |   |   |   |   | 360 |   |   |   |   | 365 |   |   |

| Thr | Leu | Tyr | His | Trp | His | Pro | Leu | Leu | Pro | Asp | Thr | Phe | Asn | Ile | Glu |
|---|---|---|---|---|---|---|---|---|---|---|---|---|---|---|---|
|   | 370 |   |   |   |   | 375 |   |   |   |   | 380 |   |   |   |   |

| Asp | Gln | Glu | Tyr | Ser | Phe | Lys | Gln | Phe | Leu | Tyr | Asn | Asn | Ser | Ile | Leu |
|---|---|---|---|---|---|---|---|---|---|---|---|---|---|---|---|
| 385 |   |   |   |   | 390 |   |   |   |   | 395 |   |   |   |   | 400 |

| Leu | Glu | His | Gly | Leu | Thr | Gln | Phe | Val | Glu | Ser | Phe | Thr | Arg | Gln | Ile |
|---|---|---|---|---|---|---|---|---|---|---|---|---|---|---|---|
|   |   |   |   | 405 |   |   |   |   | 410 |   |   |   |   | 415 |   |

| Ala | Gly | Arg | Val | Ala | Gly | Gly | Arg | Asn | Val | Pro | Ile | Ala | Val | Gln | Ala |
|---|---|---|---|---|---|---|---|---|---|---|---|---|---|---|---|
|   |   |   | 420 |   |   |   |   | 425 |   |   |   |   | 430 |   |   |

| Val | Ala | Lys | Ala | Ser | Ile | Asp | Gln | Ser | Arg | Glu | Met | Lys | Tyr | Gln | Ser |
|---|---|---|---|---|---|---|---|---|---|---|---|---|---|---|---|
|   |   |   | 435 |   |   |   |   | 440 |   |   |   |   | 445 |   |   |

| Leu | Asn | Glu | Tyr | Arg | Lys | Arg | Phe | Ser | Leu | Lys | Pro | Tyr | Thr | Ser | Phe |
|---|---|---|---|---|---|---|---|---|---|---|---|---|---|---|---|
|   |   | 450 |   |   |   |   | 455 |   |   |   |   | 460 |   |   |   |

| Glu | Glu | Leu | Thr | Gly | Glu | Lys | Glu | Met | Ala | Ala | Glu | Leu | Lys | Ala | Leu |
|---|---|---|---|---|---|---|---|---|---|---|---|---|---|---|---|
| 465 |   |   |   |   | 470 |   |   |   |   | 475 |   |   |   |   | 480 |

| Tyr | Ser | Asp | Ile | Asp | Val | Met | Glu | Leu | Tyr | Pro | Ala | Leu | Leu | Val | Glu |
|---|---|---|---|---|---|---|---|---|---|---|---|---|---|---|---|
|   |   |   |   | 485 |   |   |   |   | 490 |   |   |   |   | 495 |   |

| Lys | Pro | Arg | Pro | Asp | Ala | Ile | Phe | Gly | Glu | Thr | Met | Val | Glu | Leu | Gly |
|---|---|---|---|---|---|---|---|---|---|---|---|---|---|---|---|
|   |   |   | 500 |   |   |   |   | 505 |   |   |   |   | 510 |   |   |

| Ala | Pro | Phe | Ser | Leu | Lys | Gly | Leu | Met | Gly | Asn | Pro | Ile | Cys | Ser | Pro |
|---|---|---|---|---|---|---|---|---|---|---|---|---|---|---|---|
|   |   |   | 515 |   |   |   |   | 520 |   |   |   |   | 525 |   |   |

| Gln | Tyr | Trp | Lys | Pro | Ser | Thr | Phe | Gly | Gly | Glu | Val | Gly | Phe | Lys | Ile |
|---|---|---|---|---|---|---|---|---|---|---|---|---|---|---|---|
|   |   |   | 530 |   |   |   |   | 535 |   |   |   |   | 540 |   |   |

| Ile | Asn | Thr | Ala | Ser | Ile | Gln | Ser | Leu | Ile | Cys | Asn | Asn | Val | Lys | Gly |
|---|---|---|---|---|---|---|---|---|---|---|---|---|---|---|---|
| 545 |   |   |   |   | 550 |   |   |   |   | 555 |   |   |   |   | 560 |

| Cys | Pro | Phe | Thr | Ser | Phe | Asn | Val | Gln | Asp | Pro | Gln | Pro | Thr | Lys | Thr |
|---|---|---|---|---|---|---|---|---|---|---|---|---|---|---|---|
|   |   |   |   | 565 |   |   |   |   | 570 |   |   |   |   | 575 |   |

| Ala | Thr | Ile | Asn | Ala | Ser | Ala | Ser | His | Ser | Arg | Leu | Asp | Asp | Ile | Asn |

|  |  | 580 |  |  | 585 |  |  | 590 |  |
| --- | --- | --- | --- | --- | --- | --- | --- | --- | --- |
| Pro | Thr | Val | Leu | Ile | Lys | Arg | Arg | Ser | Thr | Glu | Leu |
|  |  | 595 |  |  |  | 600 |  |  |  |

(2) INFORMATION FOR SEQ ID NO:3:

(i) SEQUENCE CHARACTERISTICS:
        (A) LENGTH: 1834 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:3:

| | | | | | |
|---|---|---|---|---|---|
| CCGCTGCGAT | GCTCGCCCGC | GCCCTGCTGC | TGTGCGCGGT | CCTGGCGCTC | AGCCATACAG | 60 |
| CAAATCCTTG | CTGTTCCCAC | CCATGTCAAA | ACCCAGGTGT | ATGTATGAGT | GTGGGATTTG | 120 |
| ACCAGTATAA | GTGCGATTGT | ACCCGGACAG | GATTCTATGG | AGAAAACTGC | TCAACACCGG | 180 |
| AATTTTTGAC | AAGAATAAAA | TTATTTCTGA | AACCCACTCC | AAACACAGTG | CACTACATAC | 240 |
| TTACCCACTT | CAAGGGATTT | TGGAACGTTG | TGAATAACAT | TCCCTTCCTT | CGAAATGCAA | 300 |
| TTATGAGTTA | TGTGTTGACA | TCCAGATCAC | ATTTGATTGA | CAGTCCACCA | ACTTACAATG | 360 |
| CTGACTATGG | CTACAAAAGC | TGGGAAGCCT | TCTCCAACCT | CTCCTATTAT | ACTAGAGCCC | 420 |
| TTCCTCCTGT | GCCTGATGAT | TGCCCGACTC | CCTTGGGTGT | CAAAGGTAAA | AAGCAGCTTC | 480 |
| CTGATTCAAA | TGAGATTGTG | GAAAAATTGC | TTCTAAGAAG | AAAGTTCATC | CCTGATCCCC | 540 |
| AGGGCTCAAA | CATGATGTTT | GCATTCTTTG | CCCAGCACTT | CACGCATCAG | TTTTCAAGA | 600 |
| CAGATCATAA | GCGAGGGCCA | GCTTTCACCA | ACGGGCTGGG | CCATGGGGTG | GACTTAAATC | 660 |
| ATATTTACGG | TGAAACTCTG | GCTAGACAGC | GTAAACTGCG | CCTTTTCAAG | GATGGAAAAA | 720 |
| TGAAATATCA | GATAATTGAT | GGAGAGATGT | ATCCTCCCAC | AGTCAAAGAT | ACTCAGGCAG | 780 |
| AGATGATCTA | CCCTCCTCAA | GTCCCTGAGC | ATCTACGGTT | TGCTGTGGGG | CAGGAGGTCT | 840 |
| TTGGTCTGGT | GCCTGGTCTG | ATGATGTATG | CCACAATCTG | GCTGCGGGAA | CACAACAGAG | 900 |
| TATGCGATGT | GCTTAAACAG | GAGCATCCTG | AATGGGGTGA | TGAGCAGTTG | TTCCAGACAA | 960 |
| GCAGGCTAAT | ACTGATAGGA | GAGACTATTA | AGATTGTGAT | TGAAGATTAT | GTGCAACACT | 1020 |
| TGAGTGGCTA | TCACTTCAAA | CTGAAGTTTG | ACCCAGAACT | ACTTTTCAAC | AAACAGTTCC | 1080 |
| AGTACCAAAA | TCGTATTGCT | GCTGAATTTA | ACACCCTCTA | TCACTGGCAT | CCCCTTCTGC | 1140 |
| CTGACACCTT | TCAAATTCAT | GACCAGAAAT | ACAACTATCA | ACAGTTTATC | TACAACAACT | 1200 |
| CTATATTGCT | GGAACATGGA | ATTACCCAGT | TTGTTGAATC | ATTCACCAGG | CAGATTGCTG | 1260 |
| GCAGGGTTGC | TGGTGGTAGG | AATGTTCCAC | CCGCAGTACA | GAAAGTATCA | CAGGCTTCCA | 1320 |
| TTGACCAGAG | CAGGCAGATG | AAATACCAGT | CTTTTAATGA | GTACCGCAAA | CGCTTTATGC | 1380 |
| TGAAGCCCTA | TGAATCATTT | GAAGAACTTA | CAGGAGAAAA | GGAAATGTCT | GCAGAGTTGG | 1440 |
| AAGCACTCTA | TGGTGACATC | GATGCTGTGG | AGCTGTATCC | TGCCCTTCTG | GTAGAAAAGC | 1500 |
| CTCGGCCAGA | TGCCATCTTT | CCTCAAACCA | TCCTACAACT | TGGAGCACCA | TTCTCCTTGA | 1560 |
| AACCACTTAT | GGGTAATGTT | ATATGTTCTC | CTGCCTACTG | GAAGCCAAGC | ACTTTTGGTG | 1620 |
| GAGAAGTGGG | TTTTCAAATC | ATCAACACTG | CCTCAATTCA | GTCTCTCATC | TGCAATAACG | 1680 |
| TGAAGGGCTG | TCCCTTTACT | TCATTCAGTG | TTCCAGATCC | AGAGCTCATT | AAAACAGTCA | 1740 |
| CCATCAATGC | AAGTTCTTCC | CGCTCCGGAC | TAGATGATAT | CAATCCCACA | CTACTACTAA | 1800 |
| AAGAACGTTC | GACTGAACTG | TAGAAGTCTA | ATAC | | | 1834 |

( 2 ) INFORMATION FOR SEQ ID NO:4:

( i ) SEQUENCE CHARACTERISTICS:
        ( A ) LENGTH: 604 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:4:

```
Met Leu Ala Arg Ala Leu Leu Leu Cys Ala Val Leu Ala Leu Ser His
  1               5                  10                  15
Thr Ala Asn Pro Cys Cys Ser His Pro Cys Gln Asn Arg Gly Val Cys
                 20                  25                  30
Met Ser Val Gly Phe Asp Gln Tyr Lys Cys Asp Cys Thr Arg Thr Gly
             35                  40                  45
Phe Tyr Gly Glu Asn Cys Ser Thr Pro Glu Phe Leu Thr Arg Ile Lys
         50                  55                  60
Leu Phe Leu Lys Pro Thr Pro Asn Thr Val His Tyr Ile Leu Thr His
 65                  70                  75                  80
Phe Lys Gly Phe Trp Asn Val Val Asn Asn Ile Pro Phe Leu Arg Asn
                 85                  90                  95
Ala Ile Met Ser Tyr Val Leu Thr Ser Arg Ser His Leu Ile Asp Ser
            100                 105                 110
Pro Pro Thr Tyr Asn Ala Asp Tyr Gly Tyr Lys Ser Trp Glu Ala Phe
            115                 120                 125
Ser Asn Leu Ser Tyr Tyr Thr Arg Ala Leu Pro Pro Val Pro Asp Asp
        130                 135                 140
Cys Pro Thr Pro Leu Gly Val Lys Gly Lys Lys Gln Leu Pro Asp Ser
145                 150                 155                 160
Asn Glu Ile Val Glu Lys Leu Leu Leu Arg Arg Lys Phe Ile Pro Asp
                165                 170                 175
Pro Gln Gly Ser Asn Met Met Phe Ala Phe Phe Ala Gln His Phe Thr
            180                 185                 190
His Gln Phe Phe Lys Thr Asp His Lys Arg Gly Pro Ala Phe Thr Asn
        195                 200                 205
Gly Leu Gly His Gly Val Asp Leu Asn His Ile Tyr Gly Glu Thr Leu
    210                 215                 220
Ala Arg Gln Arg Lys Leu Arg Leu Phe Lys Asp Gly Lys Met Lys Tyr
225                 230                 235                 240
Gln Ile Ile Asp Gly Glu Met Tyr Pro Pro Thr Val Lys Asp Thr Gln
                245                 250                 255
Ala Glu Met Ile Tyr Pro Pro Gln Val Pro Glu His Leu Arg Phe Ala
            260                 265                 270
Val Gly Gln Glu Val Phe Gly Leu Val Pro Gly Leu Met Met Tyr Ala
        275                 280                 285
Thr Ile Trp Leu Arg Glu His Asn Arg Val Cys Asp Val Leu Lys Gln
    290                 295                 300
Glu His Pro Glu Trp Gly Asp Glu Gln Leu Phe Gln Thr Ser Arg Leu
305                 310                 315                 320
Ile Leu Ile Gly Glu Thr Ile Lys Ile Val Ile Glu Asp Tyr Val Gln
                325                 330                 335
His Leu Ser Gly Tyr His Phe Lys Leu Lys Phe Asp Pro Glu Leu Leu
            340                 345                 350
Phe Asn Lys Gln Phe Gln Tyr Gln Asn Arg Ile Ala Ala Glu Phe Asn
```

|     |     |     |     | 355 |     |     |     | 360 |     |     |     | 365 |     |     |
| --- | --- | --- | --- | --- | --- | --- | --- | --- | --- | --- | --- | --- | --- | --- |
| Thr | Leu | Tyr | His | Trp | His | Pro | Leu | Leu | Pro | Asp | Thr | Phe | Gln | Ile | His |
|     | 370 |     |     |     |     | 375 |     |     |     |     | 380 |     |     |     |
| Asp | Gln | Lys | Tyr | Asn | Tyr | Gln | Gln | Phe | Ile | Tyr | Asn | Asn | Ser | Ile | Leu |
| 385 |     |     |     |     | 390 |     |     |     |     | 395 |     |     |     |     | 400 |
| Leu | Glu | His | Gly | Ile | Thr | Gln | Phe | Val | Glu | Ser | Phe | Thr | Arg | Gln | Ile |
|     |     |     |     | 405 |     |     |     |     | 410 |     |     |     |     | 415 |     |
| Ala | Gly | Arg | Val | Ala | Gly | Gly | Arg | Asn | Val | Pro | Pro | Ala | Val | Gln | Lys |
|     |     |     | 420 |     |     |     |     | 425 |     |     |     |     | 430 |     |     |
| Val | Ser | Gln | Ala | Ser | Ile | Asp | Gln | Ser | Arg | Gln | Met | Lys | Tyr | Gln | Ser |
|     |     | 435 |     |     |     |     | 440 |     |     |     |     | 445 |     |     |     |
| Phe | Asn | Glu | Tyr | Arg | Lys | Arg | Phe | Met | Leu | Lys | Pro | Tyr | Glu | Ser | Phe |
|     | 450 |     |     |     |     | 455 |     |     |     |     | 460 |     |     |     |     |
| Glu | Glu | Leu | Thr | Gly | Glu | Lys | Glu | Met | Ser | Ala | Glu | Leu | Glu | Ala | Leu |
| 465 |     |     |     |     | 470 |     |     |     |     | 475 |     |     |     |     | 480 |
| Tyr | Gly | Asp | Ile | Asp | Ala | Val | Glu | Leu | Tyr | Pro | Ala | Leu | Leu | Val | Glu |
|     |     |     |     | 485 |     |     |     |     | 490 |     |     |     |     | 495 |     |
| Lys | Pro | Arg | Pro | Asp | Ala | Ile | Phe | Gly | Glu | Thr | Met | Val | Glu | Val | Gly |
|     |     |     | 500 |     |     |     |     | 505 |     |     |     |     | 510 |     |     |
| Ala | Pro | Phe | Ser | Leu | Lys | Gly | Leu | Met | Gly | Asn | Val | Ile | Cys | Ser | Pro |
|     |     | 515 |     |     |     |     | 520 |     |     |     |     | 525 |     |     |     |
| Ala | Tyr | Trp | Lys | Pro | Ser | Thr | Phe | Gly | Gly | Glu | Val | Gly | Phe | Gln | Ile |
|     | 530 |     |     |     |     | 535 |     |     |     |     | 540 |     |     |     |     |
| Ile | Asn | Thr | Ala | Ser | Ile | Gln | Ser | Leu | Ile | Cys | Asn | Asn | Val | Lys | Gly |
| 545 |     |     |     |     | 550 |     |     |     |     | 555 |     |     |     |     | 560 |
| Cys | Pro | Phe | Thr | Ser | Phe | Ser | Val | Pro | Asp | Pro | Glu | Leu | Ile | Lys | Thr |
|     |     |     |     | 565 |     |     |     |     | 570 |     |     |     |     | 575 |     |
| Val | Thr | Ile | Asn | Ala | Ser | Ser | Ser | Arg | Ser | Gly | Leu | Asp | Asp | Ile | Asn |
|     |     |     | 580 |     |     |     |     | 585 |     |     |     |     | 590 |     |     |
| Pro | Thr | Val | Leu | Leu | Lys | Glu | Arg | Ser | Thr | Glu | Leu |     |     |     |     |
|     |     | 595 |     |     |     |     | 600 |     |     |     |     |     |     |     |     |

( 2 ) INFORMATION FOR SEQ ID NO:5:

( i ) SEQUENCE CHARACTERISTICS:
        ( A ) LENGTH: 604 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:5:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Leu | Ala | Arg | Ala | Leu | Leu | Leu | Cys | Ala | Val | Leu | Ala | Leu | Ser | His |
| 1   |     |     |     | 5   |     |     |     |     | 10  |     |     |     |     | 15  |     |
| Thr | Ala | Asn | Pro | Cys | Cys | Ser | His | Pro | Cys | Gln | Asn | Arg | Gly | Val | Cys |
|     |     |     | 20  |     |     |     |     | 25  |     |     |     |     | 30  |     |     |
| Met | Ser | Val | Gly | Phe | Asp | Gln | Tyr | Lys | Cys | Asp | Cys | Thr | Arg | Thr | Gly |
|     |     |     | 35  |     |     |     |     | 40  |     |     |     |     | 45  |     |     |
| Phe | Tyr | Gly | Glu | Asn | Cys | Ser | Thr | Pro | Glu | Phe | Leu | Thr | Arg | Ile | Lys |
|     |     | 50  |     |     |     |     | 55  |     |     |     |     | 60  |     |     |     |
| Leu | Phe | Leu | Lys | Pro | Thr | Pro | Asn | Thr | Val | His | Tyr | Ile | Leu | Thr | His |
| 65  |     |     |     |     | 70  |     |     |     |     | 75  |     |     |     |     | 80  |
| Phe | Lys | Gly | Phe | Trp | Asn | Val | Val | Asn | Asn | Ile | Pro | Phe | Leu | Arg | Asn |
|     |     |     |     | 85  |     |     |     |     | 90  |     |     |     |     | 95  |     |
| Ala | Ile | Met | Ser | Tyr | Val | Leu | Thr | Ser | Arg | Ser | His | Leu | Ile | Asp | Ser |
|     |     |     | 100 |     |     |     |     | 105 |     |     |     |     | 110 |     |     |

|  |  |  |  |  |  |  |  |  |  |  |  |  |
|---|---|---|---|---|---|---|---|---|---|---|---|---|
| Pro | Pro | Thr<br>115 | Tyr | Asn | Ala | Asp<br>120 | Tyr | Gly | Tyr | Lys | Ser<br>125 | Trp | Glu | Ala | Phe |

Pro Pro Thr Tyr Asn Ala Asp Tyr Gly Tyr Lys Ser Trp Glu Ala Phe
        115             120                 125

Ser Asn Leu Ser Tyr Tyr Thr Arg Ala Leu Pro Pro Val Pro Asp Asp
        130             135                 140

Cys Pro Thr Pro Leu Gly Val Lys Gly Lys Lys Gln Leu Pro Asp Ser
145             150                 155                     160

Asn Glu Ile Val Gly Lys Leu Leu Leu Arg Arg Lys Phe Ile Pro Asp
                165                 170                 175

Pro Gln Gly Ser Asn Met Met Phe Ala Phe Ala Gln His Phe Thr
                180             185                 190

His Gln Phe Phe Lys Thr Asp His Lys Arg Gly Pro Ala Phe Thr Asn
        195             200                 205

Gly Leu Gly His Gly Val Asp Leu Asn His Ile Tyr Gly Glu Thr Leu
        210             215                 220

Ala Arg Gln Arg Lys Leu Arg Leu Phe Lys Asp Gly Lys Met Lys Tyr
225             230                 235                     240

Gln Ile Ile Asp Gly Glu Met Tyr Pro Pro Thr Val Lys Asp Thr Gln
                245             250                 255

Ala Glu Met Ile Tyr Pro Pro Gln Val Pro Glu His Leu Arg Phe Ala
                260             265                 270

Val Gly Gln Glu Val Phe Gly Leu Val Pro Gly Leu Met Met Tyr Ala
            275             280                 285

Thr Ile Trp Leu Arg Glu His Asn Arg Val Cys Asp Val Leu Lys Gln
        290             295                 300

Glu His Pro Glu Trp Gly Asp Glu Gln Leu Phe Gln Thr Ser Arg Leu
305             310                 315                     320

Ile Leu Ile Gly Glu Thr Ile Lys Ile Val Ile Glu Asp Tyr Val Gln
                325             330                 335

His Leu Ser Gly Tyr His Phe Lys Leu Lys Phe Asp Pro Glu Leu Leu
            340             345                 350

Phe Asn Lys Gln Phe Gln Tyr Gln Asn Arg Ile Ala Ala Glu Phe Asn
        355             360                 365

Thr Leu Tyr His Trp His Pro Leu Leu Pro Asp Thr Phe Gln Ile His
370             375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
            405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435             440                 445

Phe Asn Glu Tyr Arg Lys Arg Phe Met Leu Lys Pro Tyr Glu Ser Phe
        450             455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
            485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515             520                 525

Ala Tyr Trp Lys Pro Ser Thr Phe Gly Gly Glu Val Gly Phe Gln Ile

|     |     | 530 |     |     |     |     | 535 |     |     |     |     | 540 |     |     |
| --- | --- | --- | --- | --- | --- | --- | --- | --- | --- | --- | --- | --- | --- | --- |
| Ile | Asn | Thr | Ala | Ser | Ile | Gln | Ser | Leu | Ile | Cys | Asn | Asn | Val | Lys | Gly |
| 545 |     |     |     |     | 550 |     |     |     |     | 555 |     |     |     |     | 560 |
| Cys | Pro | Phe | Thr | Ser | Phe | Ser | Val | Pro | Asp | Pro | Glu | Leu | Ile | Lys | Thr |
|     |     |     |     | 565 |     |     |     |     | 570 |     |     |     |     | 575 |     |
| Val | Thr | Ile | Asn | Ala | Ser | Ser | Ser | Arg | Ser | Gly | Leu | Asp | Asp | Ile | Asn |
|     |     |     | 580 |     |     |     |     | 585 |     |     |     |     | 590 |     |     |
| Pro | Thr | Val | Leu | Leu | Lys | Glu | Arg | Ser | Thr | Glu | Leu |     |     |     |     |
|     |     | 595 |     |     |     |     | 600 |     |     |     |     |     |     |     |     |

( 2 ) INFORMATION FOR SEQ ID NO:6:

( i ) SEQUENCE CHARACTERISTICS:
      ( A ) LENGTH: 1819 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:6:

```
CCGCGCCATG AGCCGGAGTC TCTTGCTCCG GTTCTTGCTG TTGCTGCTCC TGCTCCCGCC      60
GCTCCCCGTC CTGCTCGCGG ACCCAGGGGC GCCCACGCCA GTGAATCCCT GTTGTTACTA     120
TCCATGCCAG CACCAGGGCA TCTGTGTCCG CTTCGGCCTT GACCGCTACC AGTGTGACTG     180
CACCCGCACG GGCTATTCCG GCCCCAACTG CACCATCCCT GGCCTGTGGA CCTGGCTCCG     240
GAATTCACTG CGGCCCAGCC CCTCTTTCAC CCACTTCCTG CTCACTCACG GCGCTGGTT     300
CTGGGAGTTT GTCAATGCCA CCTTCATCCG AGAGATGCTC ATGCTCCTGG TACTCACAGT     360
GCGCTCCAAC CTTATCCCCA GTCCCCCCAC CTACAACTCT GCACATGACT ACATCAGCTG     420
GGAGTCTTTC TCCAACGTGA GCTATTACAC TCGTATTCTG CCCTCTGTGC CTAAAGATTG     480
CCCCACACCC ATGGGAACCA AAGGGAAGAA GCAGTTGCCA GATGCCCAGC TCCTGGCCCG     540
CCGCTTCCTG CTCAGGAGGA AGTTCATACC TGACCCCCAA GGCACCAACC TCATGTTTGC     600
CTTCTTTGCA CAACACTTCA CCCACCAGTT CTTCAAAACT TCTGGCAAGA TGGGTCCTGG     660
CTTCACCAAG GCCTTGGGCC ATGGGGTAGA CCTCGGCCAC ATTTATGGAG ACAATCTGGA     720
GCGTCAGTAT CAACTGCGGC TCTTTAAGGA TGGGAAACTC AAGTACCAGG TGCTGGATGG     780
AGAAATGTAC CCGCCCTCGG TAGAAGAGGC GCCTGTGTTG ATGCACTACC CCGAGGCAT     840
CCCGCCCCAG AGCCAGATGG CTGTGGGCCA GGAGGTGTTT GGGCTGCTTC CTGGGCTCAT     900
GCTGTATGCC ACGCTCTGGC TACGTGAGCA CAACCGTGTG TGTGACCTGC TGAAGGCTGA     960
GCACCCCACC TGGGGCGATG AGCAGCTTTT CCAGACGACC CGCCTCATCC TCATAGGGGA    1020
GACCATCAAG ATTGTCATCG AGGAGTACGT GCAGCAGCTG AGTGGCTATT CCTGCAGCT    1080
GAAATTTGAC CCAGAGCTGC TGTTCGGTGT CCAGTTCCAA TACCGCAACC GCATTGCCAC    1140
GGAGTTCAAC CATCTCTACC ACTGGCACCC CCTCATGCCT GACTCCTTCA AGGTGGGCTC    1200
CCAGGAGTAC AGCTACGAGC AGTTCTTGTT CAACACCTCC ATGTTGGTGG ACTATGGGGT    1260
TGAGGCCCTG GTGGATGCCT TCTCTCGCCA GATTGCTGGC CGGATCGGTG GGGCAGGAA    1320
CATGGACCAC CACATCCTGC ATGTGGCTGT GGATGTCATC AGGGAGTCTC GGGAGATGCG    1380
GCTGCAGCCC TTCAATGAGT ACCGCAAGAG GTTTGGCATG AAACCCTACA CCTCCTTCCA    1440
GGAGCTCGTA GGAGAGAAGG AGATGGCAGC AGAGTTGGAG GAATTGTATG AGACATTGA    1500
TGCGTTGGAG TTCTACCCTG GACTGCTTCT TGAAAAGTGC CATCCAAACT CTATCTTTGG    1560
GGAGAGTATG ATAGAGATTG GGCTCCCTT TTCCCTCAAG GGTCTCCTAG GAATCCCAT    1620
```

CTGTTCTCCG GAGTACTGGA AGCCGAGCAC ATTTGGCGGC GAGGTGGGCT TTAACATTGT   1680

CAAGACGGCC ACACTGAAGA AGCTGGTCTG CCTCAACACC AAGACCTGTC CCTACGTTTC   1740

CTTCCGTGTG CCGGATGCCA GTCAGGATGA TGGGCCTGCT GTGGAGCGAC CATCCACAGA   1800

GCTCTGAGGG GCAGGAAAG   1819

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:7:

Thr Ile Trp Leu Arg Glu His Asn Arg Val
1               5                   10

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:8:

Lys Ala Leu Gly His
1               5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:9:

Arg Gly Leu Gly His
1               5

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTTACCCGAA GCTTGCGCCA TGAGCCGG   28

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TTCGTTAGCG GCCGCTGCCC CTCAGAGC 28

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TCATTCTAAG CTTCCGCTGC GATGCTCGC 29

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GATCATGCGG CCGCATTAGA CTTCTACAG 29

( 2 ) INFORMATION FOR SEQ ID NO:14:

( i ) SEQUENCE CHARACTERISTICS:
        ( A ) LENGTH: 1834 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:14:

```
CCGCTGCGAT GCTCGCCCGC GCCCTGCTGC TGTGCGCGGT CCTGGCGCTC AGCCATACAG      60
CAAATCCTTG CTGTTCCCAC CCATGTCAAA ACCCAGGTGT ATGTATGAGT GTGGGATTTG     120
ACCAGTATAA GTGCGATTGT ACCCGGACAG GATTCTATGG AGAAAACTGC TCAACACCGG     180
AATTTTTGAC AAGAATAAAA TTATTTCTGA AACCCACTCC AAACACAGTG CACTACATAC     240
TTACCCACTT CAAGGGATTT TGGAACGTTG TGAATAACAT TCCCTTCCTT CGAAATGCAA     300
TTATGAGTTA TGTGTTGACA TCCAGATCAC ATTTGATTGA CAGTCCACCA ACTTACAATG     360
CTGACTATGG CTACAAAAGC TGGGAAGCCT TCTCCAACCT CTCCTATTAT ACTAGAGCCC     420
TTCCTCCTGT GCCTGATGAT TGCCCGACTC CCTTGGGTGT CAAAGGTAAA AAGCAGCTTC     480
CTGATTCAAA TGAGATTGTG GAAAAATTGC TTCTAAGAAG AAAGTTCATC CCTGATCCCC     540
AGGGCTCAAA CATGATGTTT GCATTCTTTG CCCAGCACTT CACGCATCAG TTTTTCAAGA     600
CAGATCATAA GCGAGGGCCA GCTTTCACCA ACGGGCTGGG CCATGGGGTG GACTTAAATC     660
ATATTTACGG TGAAACTCTG GCTAGACAGC GTAAACTGCG CCTTTTCAAG GATGGAAAAA     720
TGAAATATCA GATAATTGAT GGAGAGATGT ATCCTCCCAC AGTCAAAGAT ACTCAGGCAG     780
AGATGATCTA CCCTCCTCAA GTCCCTGAGC ATCTACGGTT TGCTGTGGGG CAGGAGGTCT     840
TTGGTCTGGT GCCTGGTCTG ATGATGTATG CCACAATCTG GCTGCGGGAA CACAACAGAG     900
```

| | | | | | |
|---|---|---|---|---|---|
| TATGCGATGT | GCTTAAACAG | GAGCATCCTG | AATGGGGTGA | TGAGCAGTTG | TTCCAGACAA 960 |
| GCAGGCTAAT | ACTGATAGGA | GAGACTATTA | AGATTGTGAT | TGAAGATTAT | GTGCAACACT 1020 |
| TGAGTGGCTA | TCACTTCAAA | CTGAAGTTTG | ACCCAGAACT | ACTTTTCAAC | AAACAGTTCC 1080 |
| AGTACCAAAA | TCGTATTGCT | GCTGAATTTA | ACACCCTCTA | TCACTGGCAT | CCCCTTCTGC 1140 |
| CTGACACCTT | TCAAATTCAT | GACCAGAAAT | ACAACTATCA | ACAGTTTATC | TACAACAACT 1200 |
| CTATATTGCT | GGAACATGGA | ATTACCCAGT | TTGTTGAATC | ATTCACCAGG | CAGATTGCTG 1260 |
| GCAGGGTTGC | TGGTGGTAGG | AATGTTCCAC | CCGCAGTACA | GAAAGTATCA | CAGGCTTCCA 1320 |
| TTGACCAGAG | CAGGCAGATG | AAATACCAGT | CTTTTAATGA | GTACCGCAAA | CGCTTTATGC 1380 |
| TGAAGCCCTA | TGAATCATTT | GAAGAACTTA | CAGGAGAAAA | GGAAATGTCT | GCAGAGTTGG 1440 |
| AAGCACTCTA | TGGTGACATC | GATGCTGTGG | AGCTGTATCC | TGCCCTTCTG | GTAGAAAAGC 1500 |
| CTCGGCCAGA | TGCCATCTTT | CCTCAAACCA | TCCTACAACT | TGGAGCACCA | TTCTCCTTGA 1560 |
| AACCACTTAT | GGGTAATGTT | ATATGTTCTC | CTGCCTACTG | GAAGCCAAGC | ACTTTTGGTG 1620 |
| GAGAAGTGGG | TTTTCAAATC | ATCAACACTG | CCTCAATTCA | GTCTCTCATC | TGCAATAACG 1680 |
| TGAAGGGCTG | TCCCTTTACT | TCATTCAGTG | TTCCAGATCC | AGAGCTCATT | AAAACAGTCA 1740 |
| CCATCAATGC | AAGTTCTTCC | CGCTCCGGAC | TAGATGATAT | CAATCCCACA | CTACTACTAA 1800 |
| AAGAACGTTC | GACTGAACTG | TAGAAGTCTA | ATAC | | 1834 |

( 2 ) INFORMATION FOR SEQ ID NO:15:

( i ) SEQUENCE CHARACTERISTICS:
        ( A ) LENGTH: 2400 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:15:

| | | | | | |
|---|---|---|---|---|---|
| CTCGATCAAA | CCTTTTTTTT | ATGGTACACA | ATAGTCACAG | TACTTTTCCA | TATAAAACAG 60 |
| GTTTAGTGGT | CTTAATTTAG | TTTGGCACAT | TTAATACACT | CCCATGACCA | GCATCCCAAA 120 |
| TGTACCTATC | CGTTTTATTT | TATTGTCTCA | GAATTGTCAG | TTATTTAATA | AATTATGTAA 180 |
| CTTTTTTCCT | TATGCTCAGA | TTTGCACTTC | TTTCTAAAAC | TCTGCCCATC | CTTAAAGTCC 240 |
| CAGATTCTCC | TTGAACTTTT | TTTTTTGACT | TTCCAAGTAC | ATGGAACTCT | TCACTCTATC 300 |
| CTGCTATATA | AGGTGACAGA | ATTTCCACTA | TGGGATAGAT | GGAGTTCAAT | TCCTTTGAGT 360 |
| TTAAAATAAT | CTAAATATAA | TTATTCCTTA | TGCCCTGTTT | TTCCCTCACT | TTTGTATCCA 420 |
| AATCTCTTTT | CAGACAACAG | AACAATTAAT | GTCTGATAAG | GAAGACAATG | ATGATGATCA 480 |
| CTTCAAAATG | AATTCAGGAT | TGTAATGTAA | AATTTTAGTA | CTCTCTCACA | GTATGGATTC 540 |
| TAACATGGCT | TCTAACCCAA | ACTAACATTA | GTAGCTCTAA | CTATAAACTT | CAAATTTCAG 600 |
| TAGATGCAAC | CTACTCCTTT | AAAATGAAAC | AGAAGATTGA | AATTATTAAA | TTATCAAAAA 660 |
| GAAAATGATC | CACGCTCTTA | GTTGAAATTT | CATGTAAGAT | TCCATGCAAT | AAATAGGAGT 720 |
| GCCATAAATG | GAATGATGAA | ATATGACTAG | AGGAGGAGAA | AGGCTCCTAG | ATGAGATGGG 780 |
| ATTTTAGGCA | TCCGTGTCTC | ATGAGGAATC | AGTTGTGTCA | CTAGGCAAAA | CAGTAAAAAA 840 |
| AAAAACCTCC | AAGTGAGTCT | CTTATTTATT | TTTTCTTAT | AAGACTTCTA | CAAATTGAGG 900 |
| TACCTGGTGT | AGTTTTATTT | CAGGTTTTAT | GCTGTCATTT | TCCTGTAATG | CTAAGGACTT 960 |
| AGGACATAAC | TGAATTTTCT | ATTTTCCACT | TCTTTTCTGG | TGTGTGTGTA | TATATATATG 1020 |
| TATATATACA | CACACACATA | TACATATATA | TATTTTTTAG | TATCTCACCC | TCACATGCTC 1080 |

| | | | | | | |
|---|---|---|---|---|---|---|
|CTCCCTGAGC|ACTACCCATG|ATAGATGTTA|AACAAAAGCA|AAGATGAAAT|TCCAACTGTC|1140|
|AAAATCCCCC|CTCCATCTAA|TTAATCCCTC|ACCCAACTAT|GTTCCAAAAC|GAGAATAGAA|1200|
|AATTAGCCCC|AATAAGCCCA|GGCAACTGAA|AAGTAAATGC|TATGTTGTAC|TTTGATCCAT|1260|
|GGTCACAACT|CATAATCTTG|GAAAAGTGGA|CAGAAAAGAC|AAAAGAGTGA|ACTTTAAAAC|1320|
|TCGAATTTAT|TTTACCAGTA|TCTCCTATGA|AGGGCTAGTA|ACCAAAATAA|TCCACGCATC|1380|
|AGGGAGAGAA|ATGCCTTAAG|GCATACGTTT|TGGACATTTA|GCGTCCCTGC|AAATTCTGGC|1440|
|CATCGCCGCT|TCCTTTGTCC|ATCAGAAGGC|AGGAAACTTT|ATATTGGTGA|CCCGTGGAGC|1500|
|TCACATTAAC|TATTTACAGG|GTAACTGCTT|AGGACCAGTA|TTATGAGGAG|AATTTACCTT|1560|
|TCCCGCCTCT|CTTTCCAAGA|AACAAGGAGG|GGGTGAAGGT|ACGGAGAACA|GTATTTCTTC|1620|
|TGTTGAAAGC|AACTTAGCTA|CAAAGATAAA|TTACAGCTAT|GTACACTGAA|GGTAGCTATT|1680|
|TCATTCCACA|AAATAAGAGT|TTTTTAAAAA|GCTATGTATG|TATGTGCTGC|ATATAGAGCA|1740|
|GATATACAGC|CTATTAAGCG|TCGTCACTAA|AACATAAAAC|ATGTCAGCCT|TTCTTAACCT|1800|
|TACTCGCCCC|AGTCTGTCCC|GACGTGACTT|CCTCGACCCT|CTAAAGACGT|ACAGACCAGA|1860|
|CACGGCGGCG|GCGGCGGGAG|AGGGGATTCC|CTGCGGCCCC|GGACCTCAGG|GCCGCTCAGA|1920|
|TTCCTGGAGA|GGAAGCCAAG|TGTCCTTCTG|CCCTCCCCCG|GTATCCATC|CAAGGCGATC|1980|
|AGTCCACAAC|TGGCTCTCGG|AAGCACTCGG|GCAAAGACTG|CGAAGAAGAA|AAGACATCTG|2040|
|GCGGAAACCT|GTGCGCCTGG|GGCGGTGGAA|CTCGGGGAGG|AGAGGGAGGG|ATCAGACAGG|2100|
|AGAGTGGGGA|CTACCCCCTC|TGCTCCCAAA|TTGGGGCAGC|TTCCTGGGTT|TCCGATTTTC|2160|
|TCATTTCCGT|GGGTAAAAAA|CCCTGCCCCC|ACCGGCTTAC|GCAATTTTTT|TAAGGGGAGA|2220|
|GGAGGGAAAA|ATTTGTGGGG|GGTACGAAAA|GGCGGAAAGA|AACAGTCATT|TCGTCACATG|2280|
|GGCTTGGTTT|TCAGTCTTAT|AAAAAGGAAG|GTTCTCTCGG|TTAGCGACCA|ATTGTCATAC|2340|
|GACTTGCAGT|GAGCGTCAGG|AGCACGTCCA|GGAACTCCTC|AGCAGCGCCT|CCTTCAGCTC|2400|

( 2 ) INFORMATION FOR SEQ ID NO:16:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:16:

TCCACCCGCA GTACAGAAAG TATCACAGGC T        31

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:17:

GTGTTCCAGA TCCAGAGCTC ATTAAAACAG T        31

( 2 ) INFORMATION FOR SEQ ID NO:18:

( i ) SEQUENCE CHARACTERISTICS:
        ( A ) LENGTH: 5 amino acids

```
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:18:

Arg  Xaa  Xaa  Xaa  His
    1                       5
```